United States Patent
Cheng et al.

(10) Patent No.: US 10,519,426 B2
(45) Date of Patent: Dec. 31, 2019

(54) COMPOSITIONS FEATURING AN ATTENUATED NEWCASTLE DISEASE VIRUS AND METHODS OF USE FOR TREATING NEOPLASIA

(71) Applicant: MEDIMMUNE LIMITED, Cambridge (GB)

(72) Inventors: Xing Cheng, Gaithersburg, MD (US); Danielle Carroll, Cambridge (GB); Matthew McCourt, Cambridgeshire (GB); Mark Galinski, Gaithersburg, MD (US); Hong Jin, Gaithersburg, MD (US)

(73) Assignee: MEDIMMUNE LIMITED, Cambridgeshire (GB)

( * ) Notice: Subject to any disclaimer, the term of this patent is extended or adjusted under 35 U.S.C. 154(b) by 647 days.

(21) Appl. No.: 14/916,102

(22) PCT Filed: Sep. 2, 2014

(86) PCT No.: PCT/EP2014/068619
§ 371 (c)(1),
(2) Date: Mar. 2, 2016

(87) PCT Pub. No.: WO2015/032755
PCT Pub. Date: Mar. 12, 2015

(65) Prior Publication Data
US 2016/0208222 A1    Jul. 21, 2016

Related U.S. Application Data

(60) Provisional application No. 61/873,039, filed on Sep. 3, 2013.

(51) Int. Cl.
| | |
|---|---|
| *C12N 7/00* | (2006.01) |
| *C12N 7/04* | (2006.01) |
| *A61K 35/768* | (2015.01) |
| *C12N 15/86* | (2006.01) |
| *C07K 14/005* | (2006.01) |
| *C07K 14/535* | (2006.01) |

(52) U.S. Cl.
CPC .............. *C12N 7/00* (2013.01); *A61K 35/768* (2013.01); *C07K 14/005* (2013.01); *C07K 14/535* (2013.01); *C12N 7/04* (2013.01); *C12N 15/86* (2013.01); *C12N 2710/16122* (2013.01); *C12N 2710/16143* (2013.01); *C12N 2760/18122* (2013.01); *C12N 2760/18132* (2013.01); *C12N 2760/18133* (2013.01); *C12N 2760/18143* (2013.01)

(58) Field of Classification Search
CPC . C12N 7/00; C12N 7/04; C12N 15/86; C12N 2760/18122; C12N 2760/18132; C12N 2760/18143; C12N 2710/16122; C12N 2710/16143; C12N 2760/18133; A61K 35/768; C07K 14/005

USPC ................ 424/199.1, 93.6; 435/320.1
See application file for complete search history.

(56) References Cited

U.S. PATENT DOCUMENTS

| | | | | |
|---|---|---|---|---|
| 7,724,558 | B1 * | 5/2010 | Ishizaka | B82Y 25/00 257/664 |
| 2010/0183664 | A1 * | 7/2010 | Cho | A61K 39/17 424/199.1 |
| 2014/0271677 | A1 * | 9/2014 | Palese | A61K 35/768 424/172.1 |

FOREIGN PATENT DOCUMENTS

| | | | |
|---|---|---|---|
| WO | WO 01/20989 | * | 3/2001 |
| WO | WO 01/20989 A1 | | 3/2001 |
| WO | WO 2009/095167 A1 | | 8/2009 |
| WO | WO 2009/101149 A2 | | 8/2009 |
| WO | WO 2010/091262 | * | 8/2010 |
| WO | WO 2010/091262 A1 | | 8/2010 |

OTHER PUBLICATIONS

Lam et al. (2011) J. Biomed. Biotech., Article ID 718710, pp. 1-13.*
Janke M, et al., "Recombinant Newcastle Disease Virus (NDV) with Inserted Gene Coding for GM-CSF as a New Vector for Cancer Immunogene Therapy", Gene Therapy, vol. 14, No. 23, 2007, pp. 1639-1649.
Dortmans, et al., "Virulence of Newcastle Disease Virus: What is Known so Far?" Veterinary Research, vol. 42, No. 1, 2011, pp. 122-132.
Dortmans, et al., "Passaging of a Newcastle Disease Virus Pigeon Variant in Chickens Results in Selection of Viruses with Mutations in the Polymerase Complex Enhancing Virus Replication and Virulence", Journal of General Virology, vol. 92, No. 2, 2011, pp. 336-345.
Fournier, et al., "Oncolytic Newcastle Disease Virus as Cutting Edge between Tumor and Host", Biology, vol. 2, No. 3, 2013, pp. 936-975.

(Continued)

*Primary Examiner* — Anne Marie S Wehbe

(57) ABSTRACT

The present invention provides methods for inducing regression of tumors in human subjects, the methods utilize a modified mesogenic strain of Newcastle disease virus (NDV) with modified F protein cleavage site, which is non-pathogenic to poultry (lentogenic), but exhibits oncolytic properties. The disclosed methods provide safe, effective and reliable means to induce regression of a tumor in an individual in need thereof. These methods overcome the drawbacks of using pathogenic strains of viruses for human therapy.

20 Claims, 36 Drawing Sheets

Specification includes a Sequence Listing.

(56) References Cited

OTHER PUBLICATIONS

Samal et al., "A Single Amino Acid Change, Q114R, in the Cleavage-Site Sequence of Newcastle Disease VirusFusion Protein Attenuates Viral Replication and Pathogenicity", Journal of General Virology, vol. 92, No. 10, 2011, pp. 2333-2338.
International Search Report and Written Opinion for PCT/EP2014/068619, pp. 1-16, dated Dec. 11, 2014.
International Preliminary Report on Patentability for PCT/EP2014/068619, pp. 1-8, dated Mar. 8, 2016.

* cited by examiner

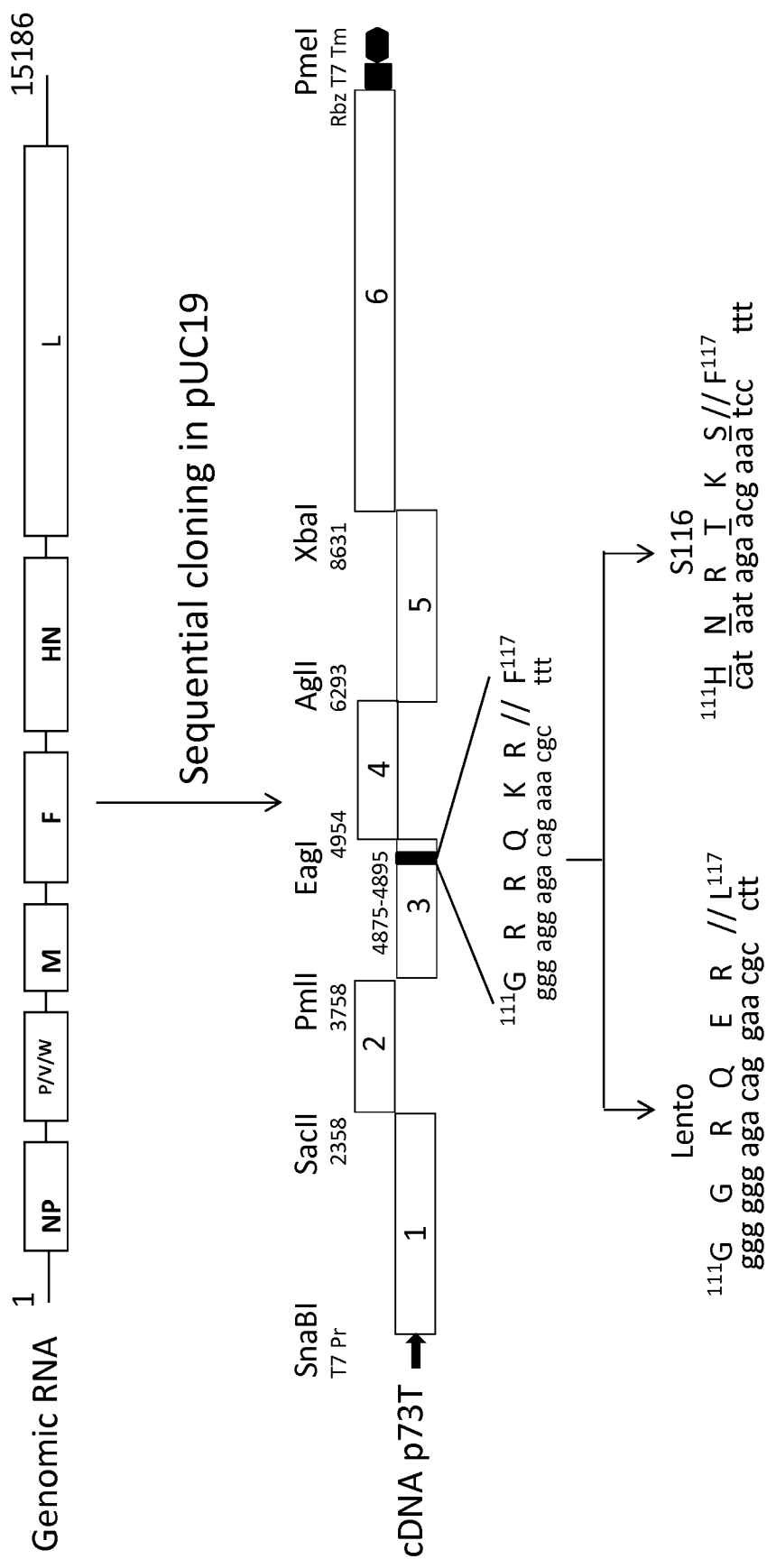
Figure 1. Construction of NDV 73T antigenomic cDNA

Figure 2. Insertion of transgene cassette(s) into NDV 73T genome
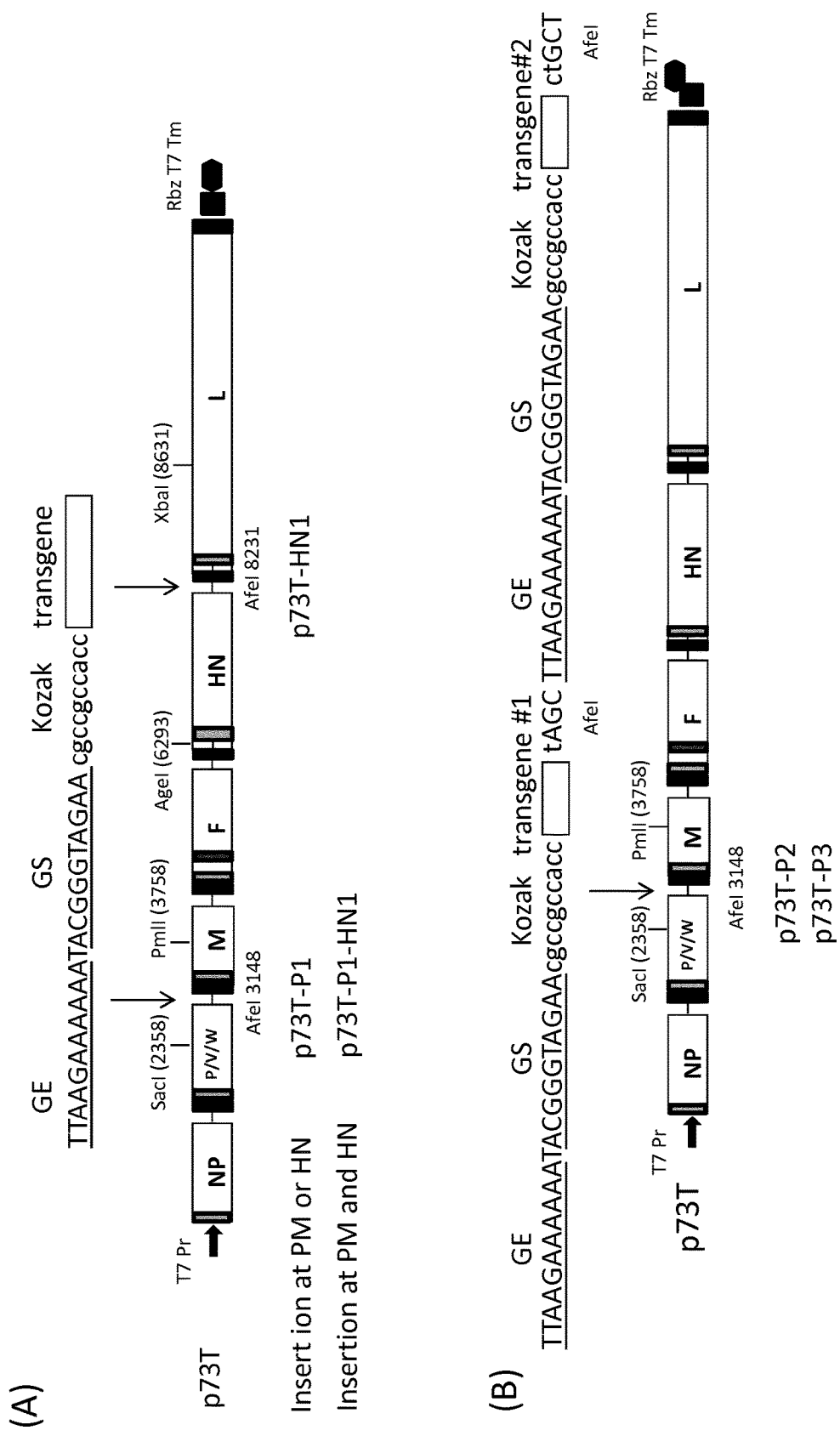

Figure 3A. Method for recovering infectious recombinant NDV strain 73T (r73T) with modified FPCS

- Transfect into T7 RNA polymerase expressing cells
- Transfect the plasmids with a plasmid encoding the T7 RNA polymerase into Vero cells by electroporation Recover r73T r73T-Lento → R113K
r73T-S116 → Q114M, R113K,Q114M, S116R Sequence changes in FPCS acquired upon virus passaging in HT1080 and Vero cells

S116-KM

Mutations in FPCS: R113K  Q114M  R113K,Q114M  S116R

Figures 3B and C. Evaluation of F protein cleavage and fusion activity in vitro
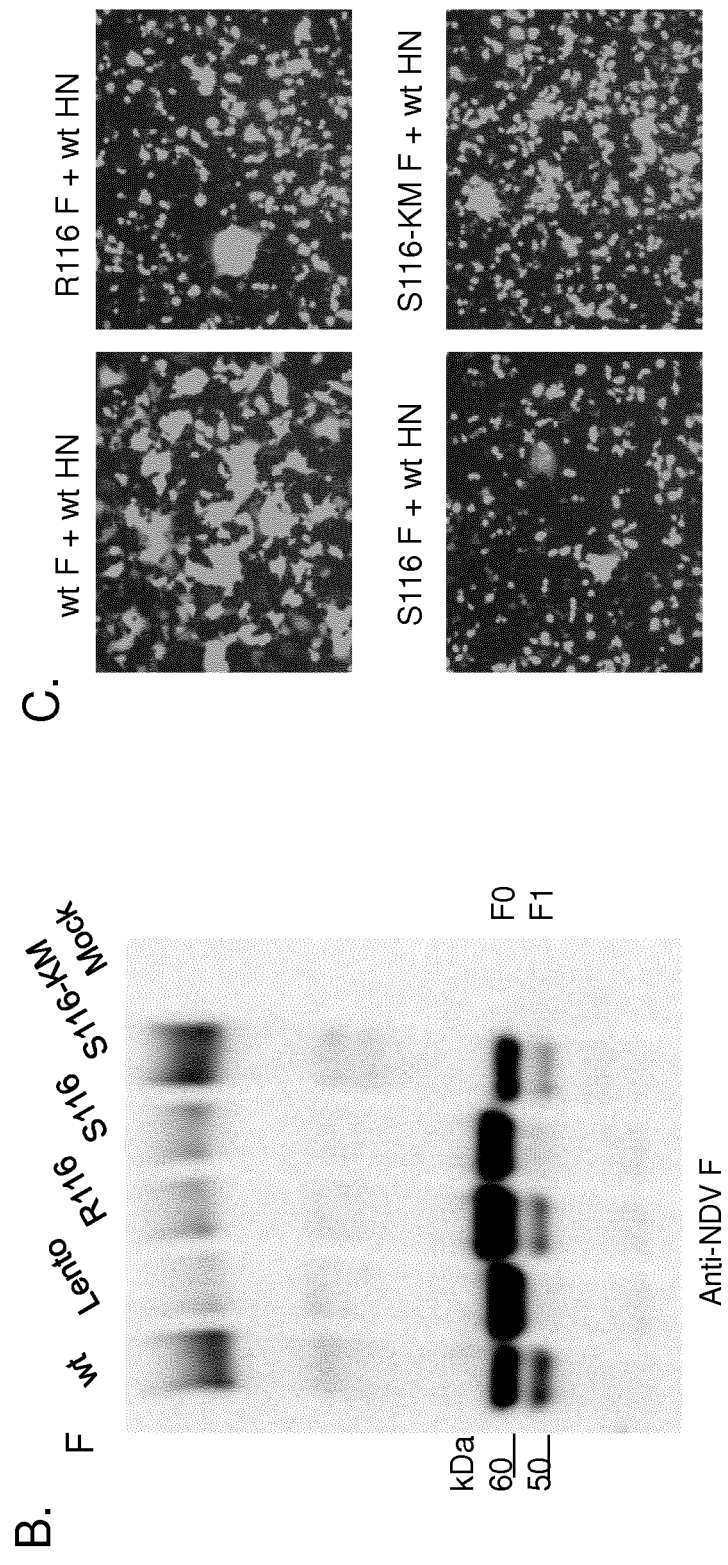

Figure 4. Summary of characteristics of r73T-lento and r73T-S116 derivatives

| Virus name (73T)[a] | FPCS sequence[b] | Plaque formation[c] | MDT (hrs)[d] | ICPI[e] | Relative HT1080 cell killing[e] | Vero (pfu/ml)[g] | Eggs (pfu/ml)[h] |
|---|---|---|---|---|---|---|---|
| -lento | [111]G-G-R-Q-E-R/L-I[118] | | > 156 | 0.00 | 13 | 7.5E+03 | 5.7E+08 |
| -S116 | [111]H-N-R-T-K-S/F-I[118] | | > 156 | 0.00 | 31 | 4.4E+06 | 4.6E+08 |
| -S116K113 | [111]H-N-K-T-K-S/F-I[118] | | > 156 | ND | 29 | 3.4E+06 | 3.8E+08 |
| -S116M114 | [111]H-N-R-M-K-S/F-I[118] | | > 156 | ND | 31 | 3.6E+06 | 3.4E+08 |
| -S116K113M114 (S116-KM) | [111]H-N-K-M-K-S/F-I[118] | | > 156 | 0.00 | 48 | 2.4E+06 | 4.2E+08 |
| -R116 | [111]H-N-R-T-K-R/F-I[118] | | 66 | 0.65 | 80 | 6.2E+06 | 1.7E+08 |

Figure 5. Strategies to attenuate r73T-R116 virus virulence in chicken (A)

1. Transgene cassette

2. Transgene cassette

3. Sequences from paramyxoviruses or random sequences

ACGGGTAGGAC [ORF] CGAAAATCACATATTAATAGGCTCTCTTTTCTGGCCAATTGTATCCTTGGTGATTAATTATACTATGTTAGAAAAAA

GS  ORF  GE

Figure 5. continued

(B) Non-coding sequences inserted at HN-L junction

APMV-1 N 318 nt
aatccttaaagaatcacagtacacaatcaaagagatgtggggacaaccacagctgtcactcttatgtggagagatactgtatgccaagcacacag
attactcacatgcagctgaagtaggaatgcagtacgtgagcacactggagagcagagcgtacaacagcagtaaagaactcaggtagtgaggtcaggcagtattgaccaagacatact
ctcttgggagggcaaaaacagcaaagggagggagttgcaatgttagcatacatgggggttgaaagaag RSV-NP 198 nt
actttctgtcatccagcaaatacgccatccaacggagcacagagagtattgatctcctaattatgatgtgcagaaacacatcaataagttatgtggcatgttattaatcacagaagatgctaat
cataaattcactgggttaatggtatgttatatgcgatgtctaggttaggaagagaagacaccataaaaat Random sequence 198 nt
gctgtgaaagcaaaaacatcgtctcttccgttggccaatactcatgatccgccaatgatataaaaaccgcggcaacgaaacgcctccttagaaggggatacaatgaccggctgagg
acatggc Figure 6A. Summary of characteristics of r73T-R116 derivatives.

| Virus Name (r73T-R116i-)[a] | Insertion at HN-L[b] | Plaque formation[c] | MDT (hrs)[d] | ICPI[e] | Relative cell killing[f] | Vero (pfu/ml)[g] | Eggs (pfu/ml)[h] |
|---|---|---|---|---|---|---|---|
| R116i | none | | 62 | 0.65 | 80 | 6.3E+06 | 2.0E+08 |
| 318 APMV | APMV-N 318nt | | >156 | 0.27 | 80 | 9.9E+06 | 5.0E+07 |
| 198 RSV | RSV-NP 198 nt | | >156 | 0.0375 | 86 | 6.4E+06 | 6.0E+07 |
| 198 | Random 198 nt | | >156 | 0 | 85 | 7.7E+06 | 5.0E+07 |
| 144 | Random 144 nt | | 79 | 0.74 | 82 | 7.3E+06 | 2.4E+08 |
| 102 | Random 102 nt | | 64 | 0.51 | 83 | 6.4E+06 | 1.1E+08 |
| 60 | Random 60 nt | | 64 | 0.78 | 75 | 6.5E+06 | 1.3E+08 |
| GFP | EGFP gene cassette | | 86 | 0.82 | 87 | 5.7E+06 | 1.5E+08 |

Figures 6B-E. r73T-R116i virus exhibits slower growth kinetics in DF-1 cells compared to Vero cells

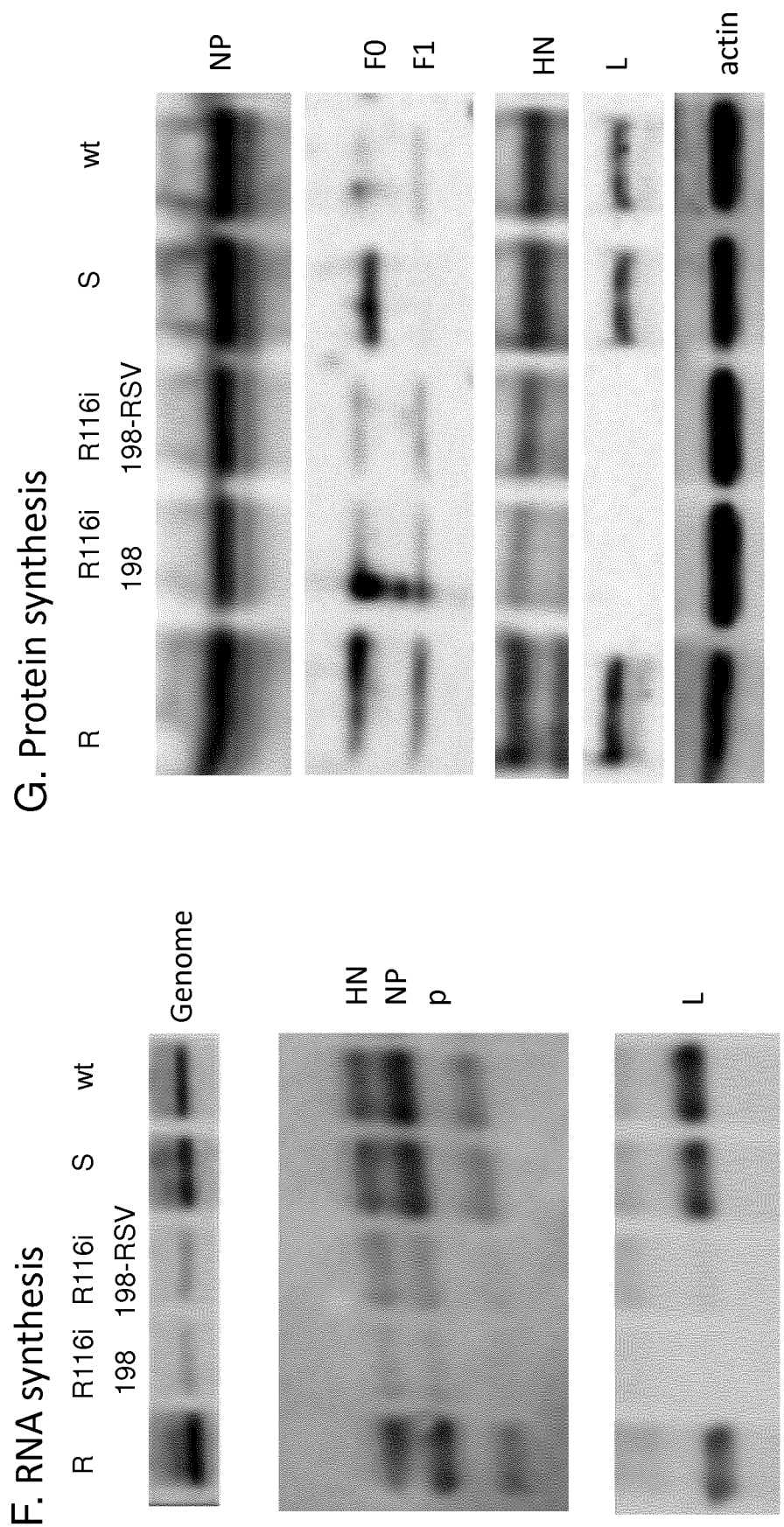
Figures 6F and G. Gene expression of r73T-R116i is reduced in DF-1 chicken fibroblast cells Figures 6H and I. Gene expression in the upstream of HN-L insertion is up-regulated whereas gene expression in the downstream is down-regulated in Vero cells infected by r73T-R116i virus H. RNA synthesis I. Protein synthesis

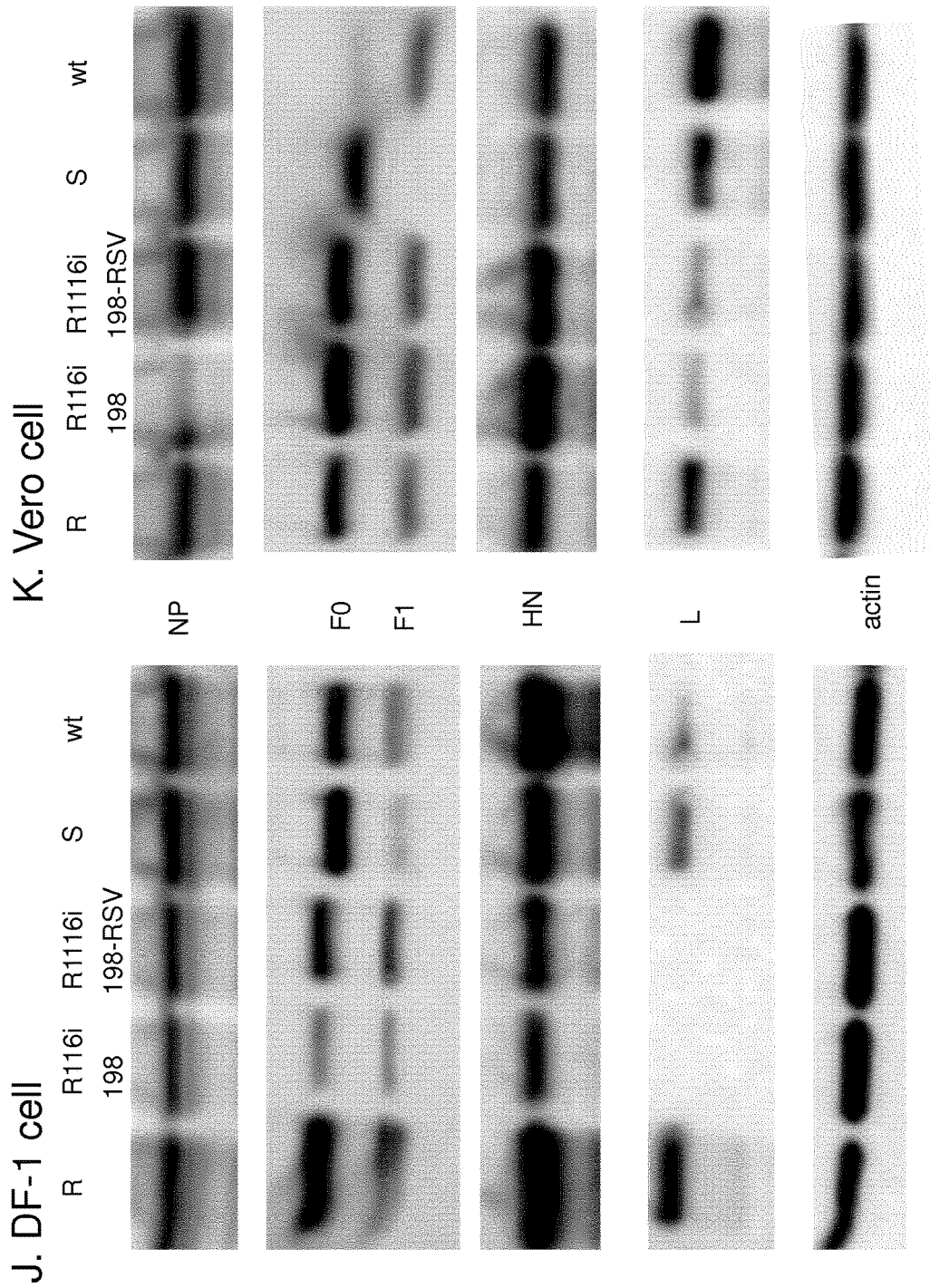
Figures 6J and K. Gene expression in DF-1 and Vero cells is affected by insertion at HN-L junction

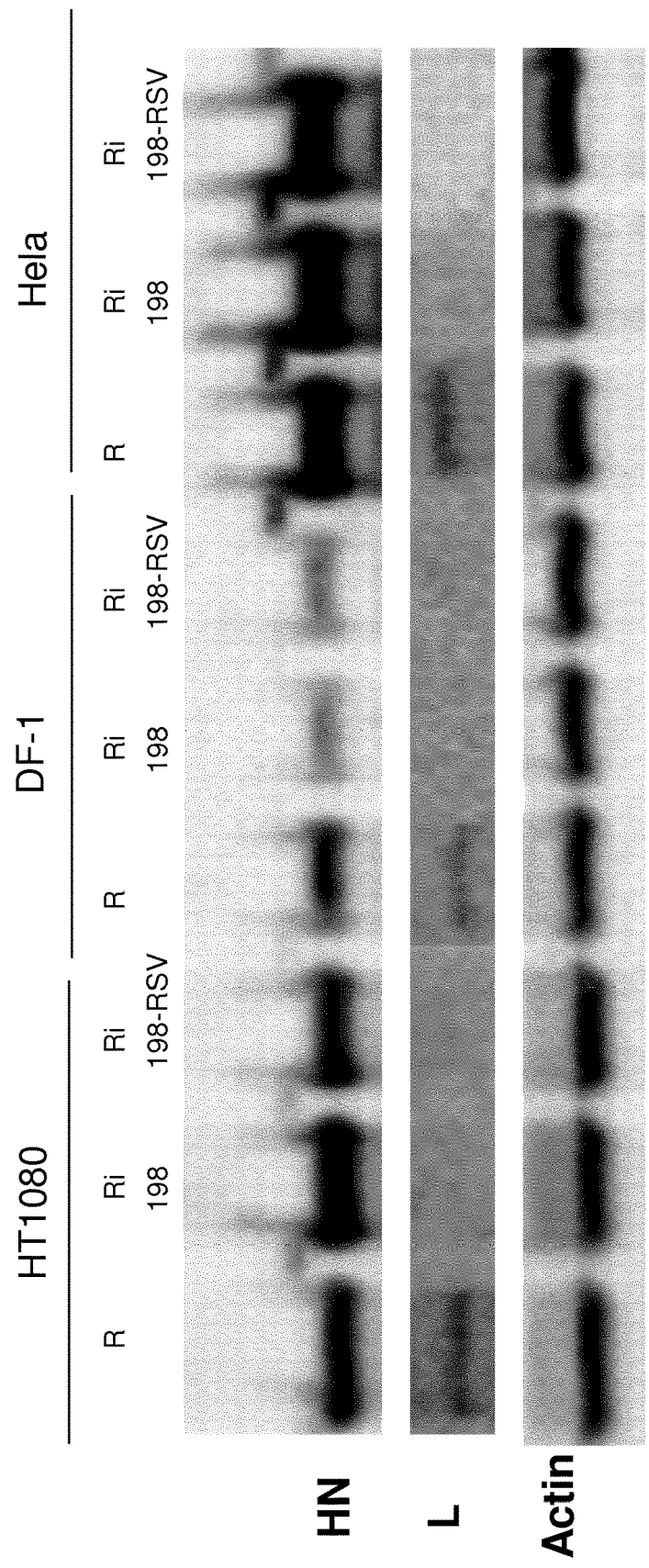
Figure 6L Expression of the upstream genes is up-regulated in r73T-R116i infected human cells Figure 7. Growth kinetics of r73T viruses in embryonated chicken eggs Figure 8. Growth kinetics of r73T viruses in Vero cells

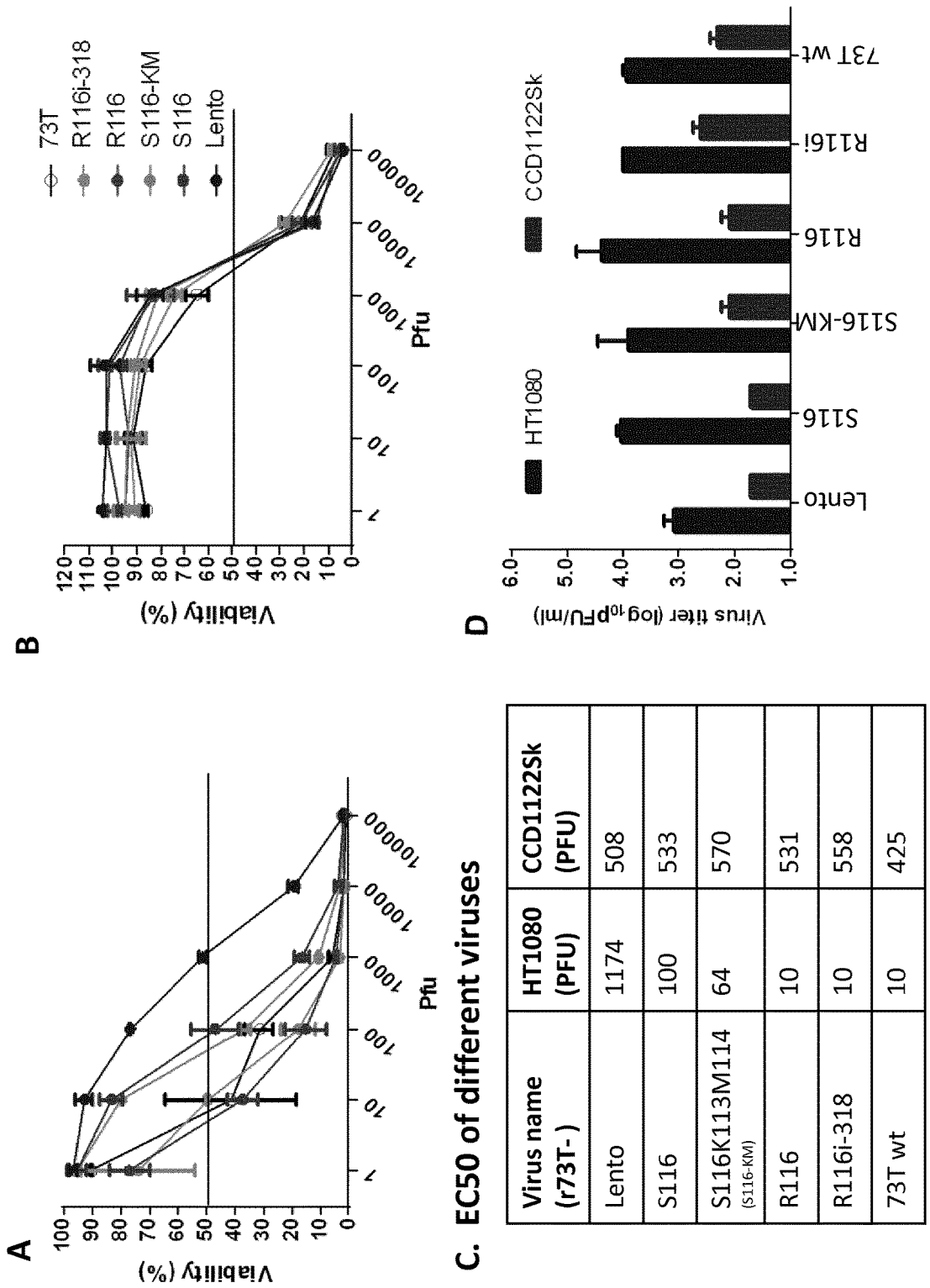
Figure 9. Selective replication and cytotoxicity of r73T virus in tumor cells

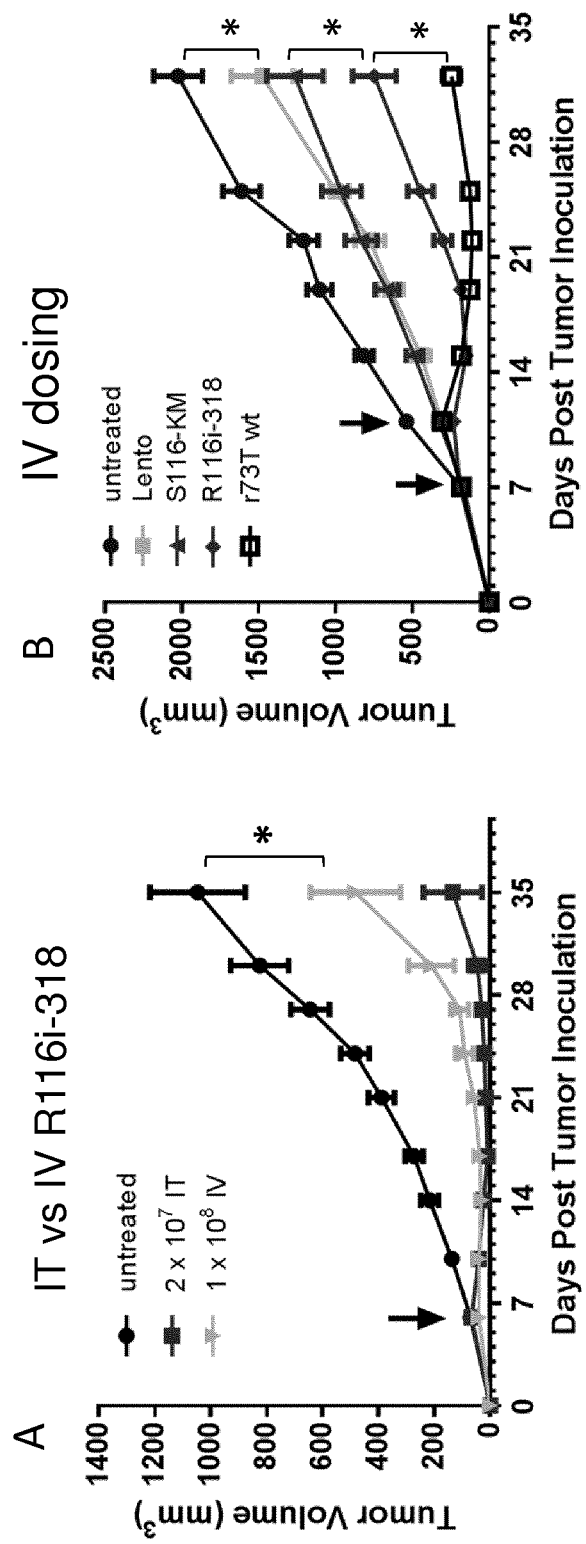
Figure 10. r73T derivatives are effective in tumor regression upon local and systemic administration

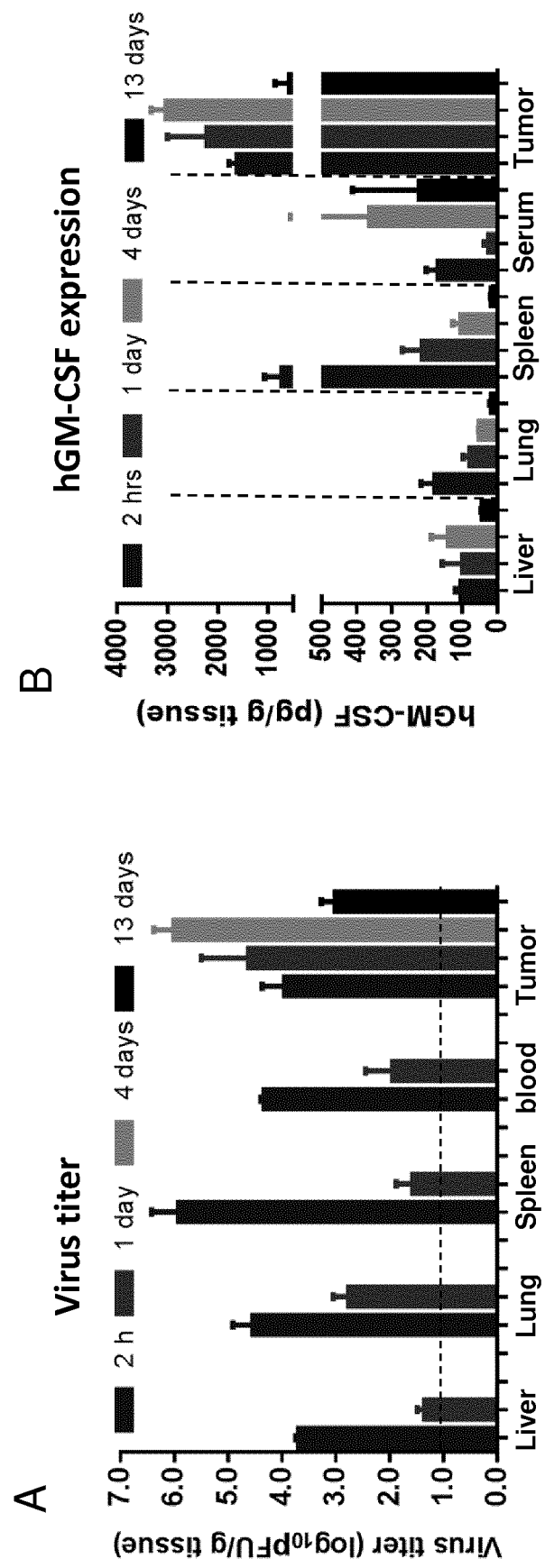
Figures 11A and B. r73T-R116i-hGM-CSF selectively replicates in Tumors following a single IV administration

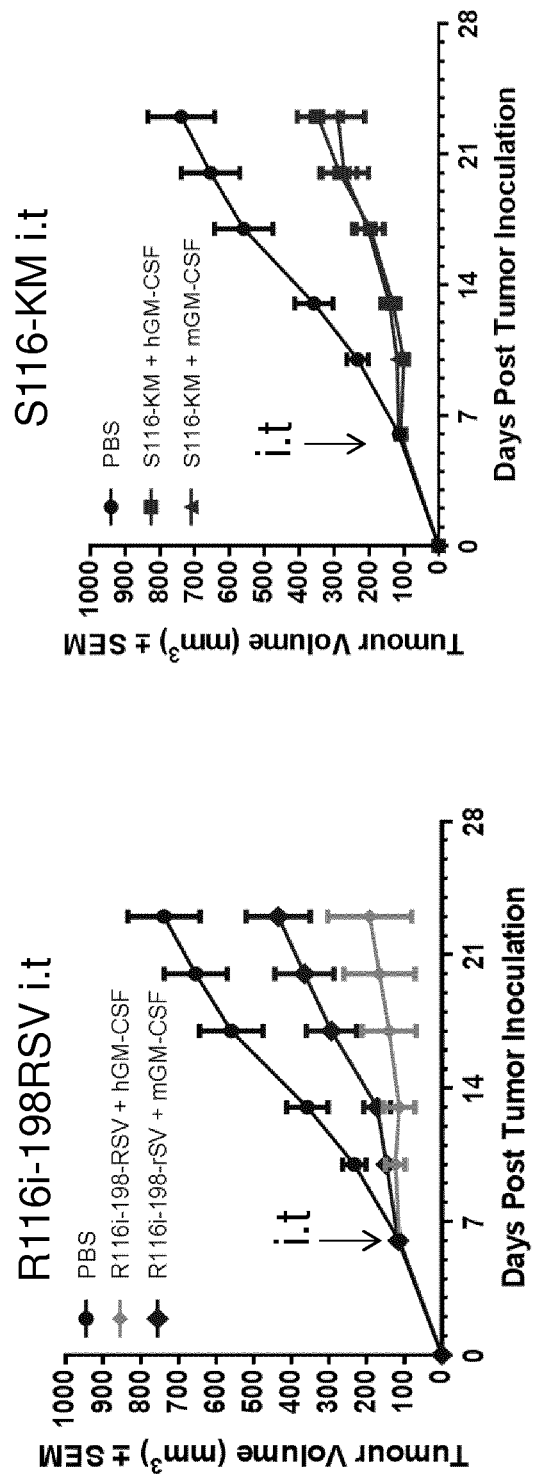
Figure 11C. Effect of mouse GM-CSF on tumor growth inhibition by IV and IT in HT1080 model Figure 11D. Expression of mouse GM-CSF accelerated virus clearance from tumors
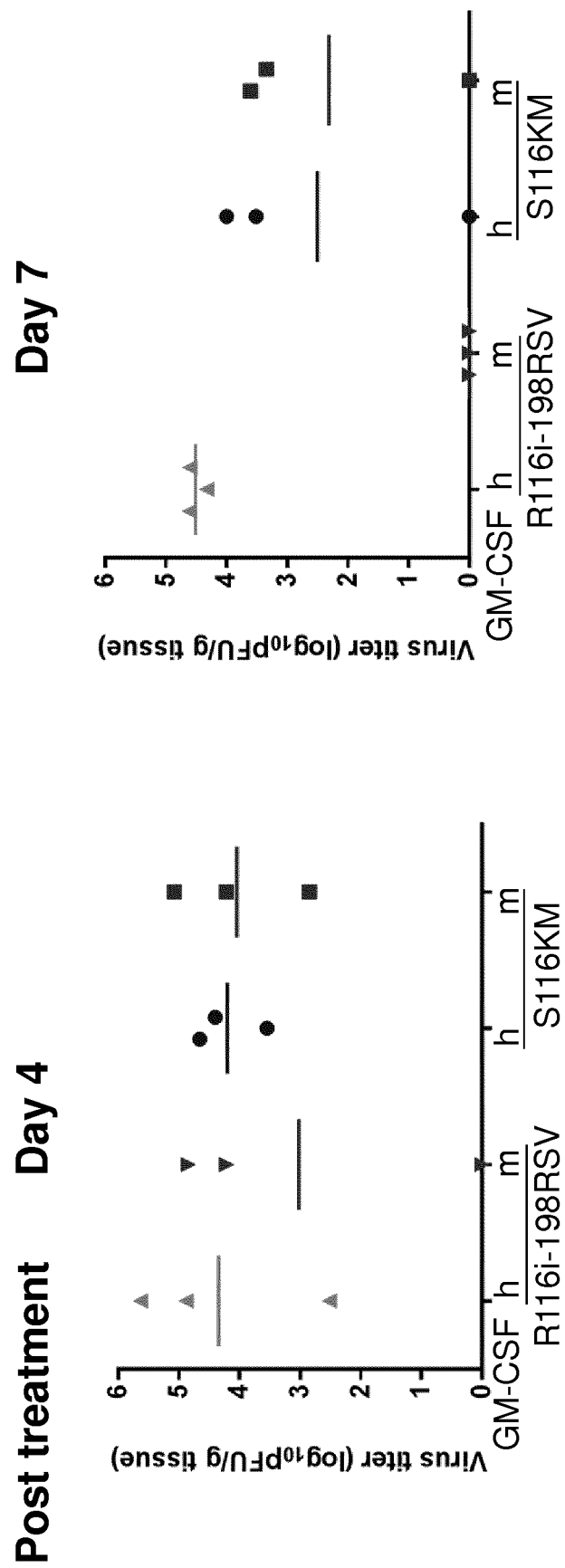

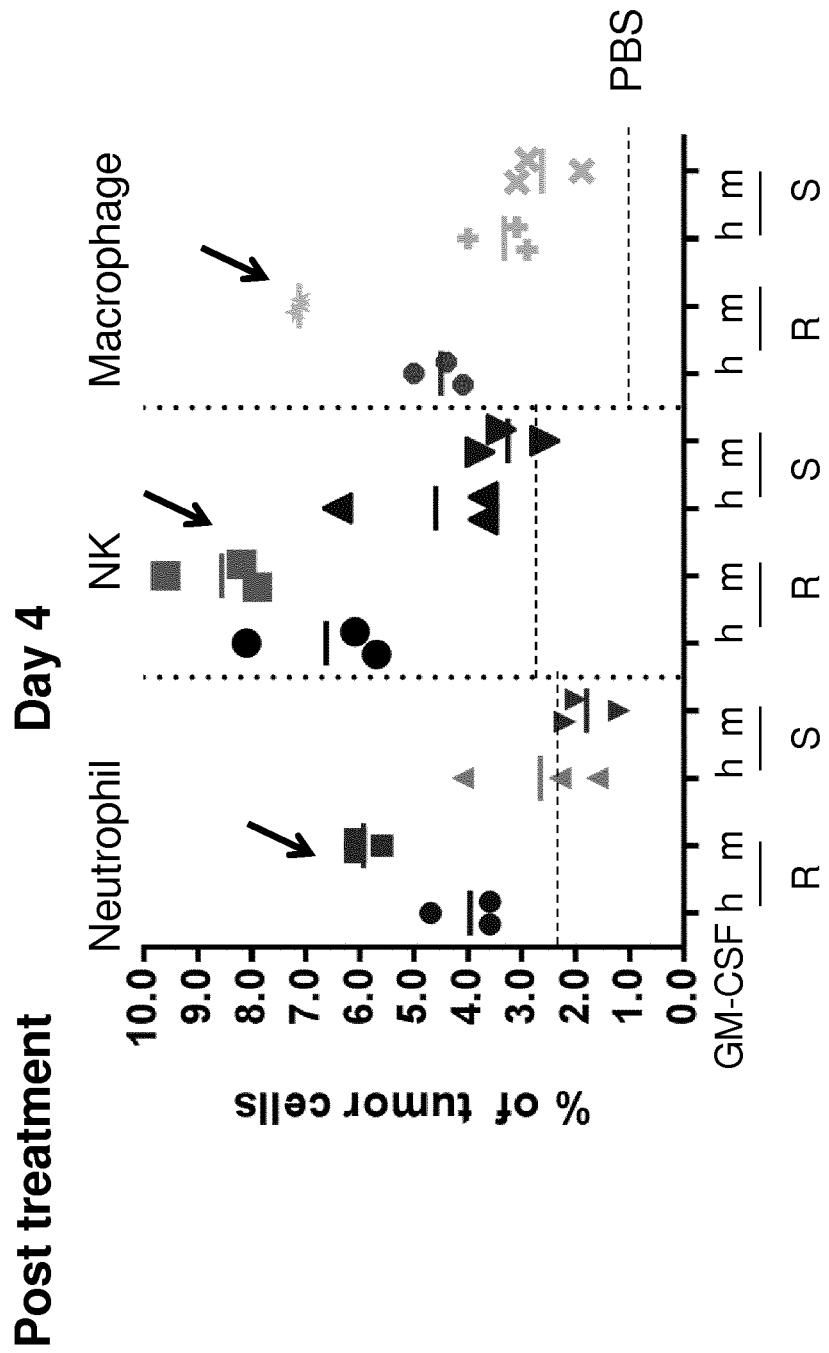
Figure 11E. Mouse GM-CSF expression induces more immune cells infiltration into tumors Figure 11F. rNDV treatment elicits up-regulation of cytokines and chemokines in tumor tissues

| Cytokine/chemokine on day 4 post treatment | Fold of change relative to PBS group | | | |
|---|---|---|---|---|
| | R | | S | |
| | hGM-CSF | mGM-CSF | hGM-CSF | mGM-CSF |
| mGM-CSF | 1.3 | 106.7 | 2.4 | 9.9 |
| MIG (CXCL9) | 3.9 | 3.1 | 5.3 | 4.9 |
| IFN-β | 51 | 28 | 8 | 12 |
| IFN-γ | 6.9 | 2.7 | 6 | 2.4 |
| IL-6 | 13.2 | 5.5 | 6.6 | 2.7 |
| IL-10 | 5.7 | 2.8 | 0.5 | 2 |
| MIP-1a (CCL3) | 37.9 | 13.4 | 15.6 | 4.4 |
| IL-12 | 2.9 | 2.5 | 2.4 | 2.3 |
| MCP-1(CCL2) | 8.4 | 9.5 | 8.9 | 5 |
| TNF-α | 5.2 | 4.7 | 3.6 | 3.7 |
| IP-10 (CXCL10) | 8.5 | 6.6 | 12.5 | 6.5 |
| RANTES (CCL5) | 24.5 | 21.2 | 35.9 | 10.1 |

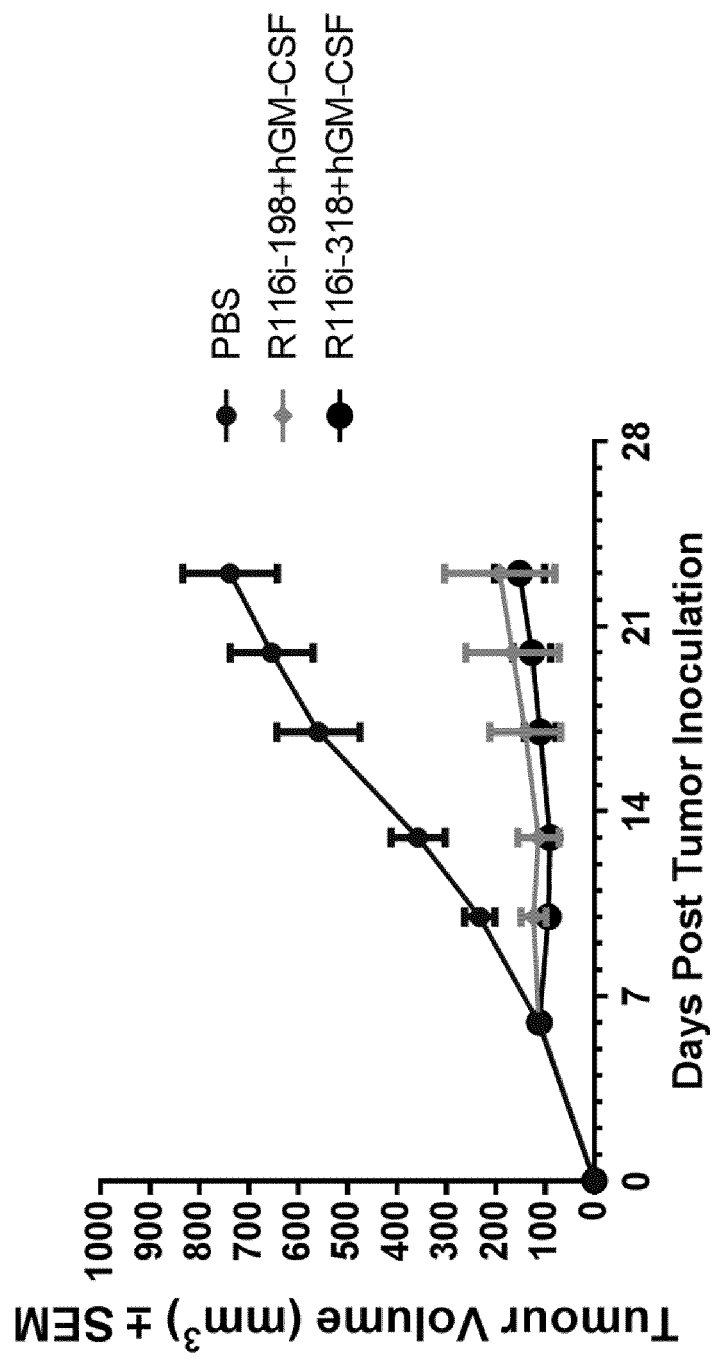
Figure 11G. R116i-318 and -198 is comparable in tumor growth inhibition Figure 12A. Construction of antigenome cDNA of 73T containing chimeric F and/or HN gene

| | Plaque formation | Relative HT1080 cell killing | MDT |
|---|---|---|---|
| PPMV-1 F-HN FPCS (1-502, 503-553, $^{111}$G R R Q K R F$^{117}$, 46-577, 1-45) | | 71 | 79 |
| PPMV-1 F (1-502, 503-553, $^{111}$G R R Q K R F$^{117}$) | | 61 | 84 |
| PIV5 F-HN FPCS (1-486, 503-553, $^{111}$T R R R R R F$^{117}$, 36-565, 1-45) | | 29 | NA |
| PIV5 Bio | | 8 | NA |

Figure 12B.

| Vero w/o trypsin | Spreading in cells | F gene | HN gene | Grow in eggs (pfu/ml) | Grown in Vero w/o trypsin (pfu/ml) |
|---|---|---|---|---|---|
|  | +++ | PIV5 NDV | PIV5 NDV | No | 6.0 x 10⁶ |
|  | ++++ | PPMV-1 NDV | NDV | 2.4 x 10⁸ | 2.1 x 10⁶ |
|  | +++ | PPMV-1 NDV | PPMV NDV | 2.7 x 10⁸ | 2.5 x 10⁶ |

Figure 12C. Compare function of RNA polymerase complex by mini-genome assay

Figures 13A and B. Cancer cell line sensitivity to rNDV variants
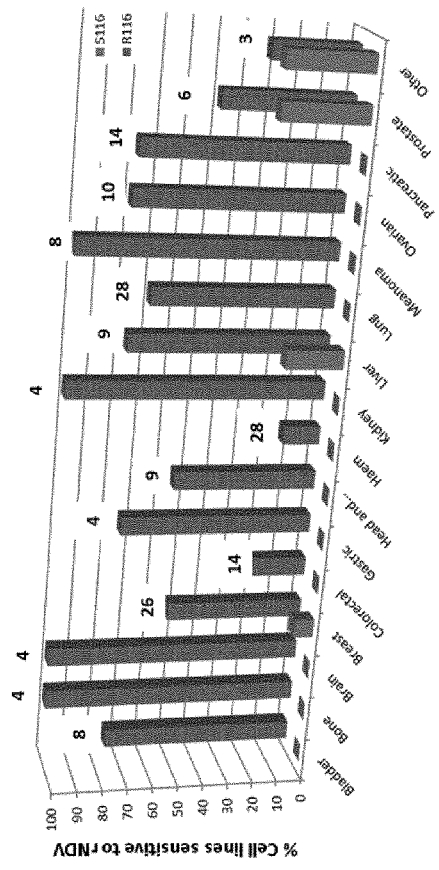
A.
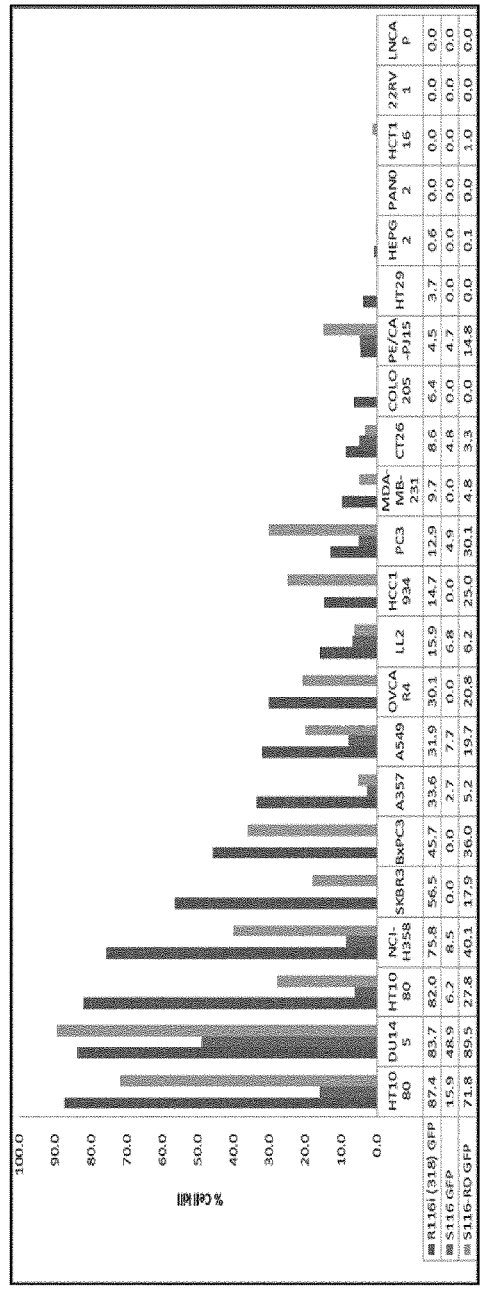
B.

Figure 14. Permissivity of the cancer cell lines to recNDV$^{GM-CSF}$
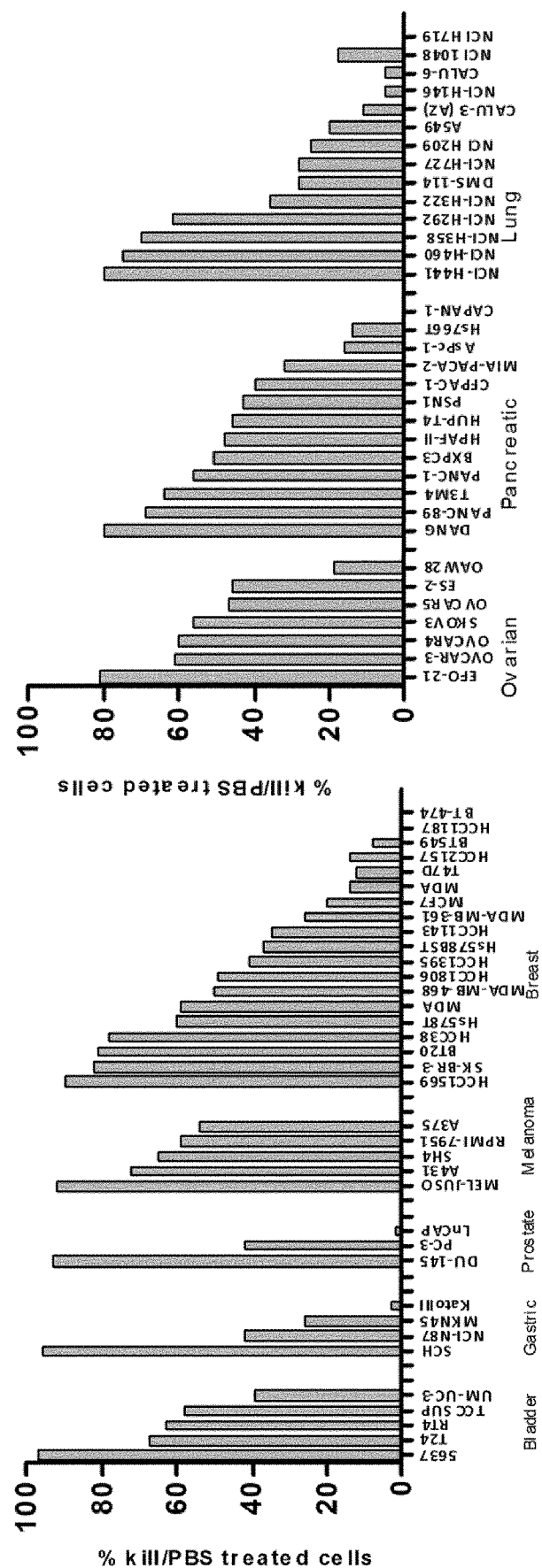
Fig legend: Cytopathic effect of rNDV variants R116i (expressing GM-CSF). Maximum % kill was determine 3 days following infection of tumour cell lines relative to non-infected control.

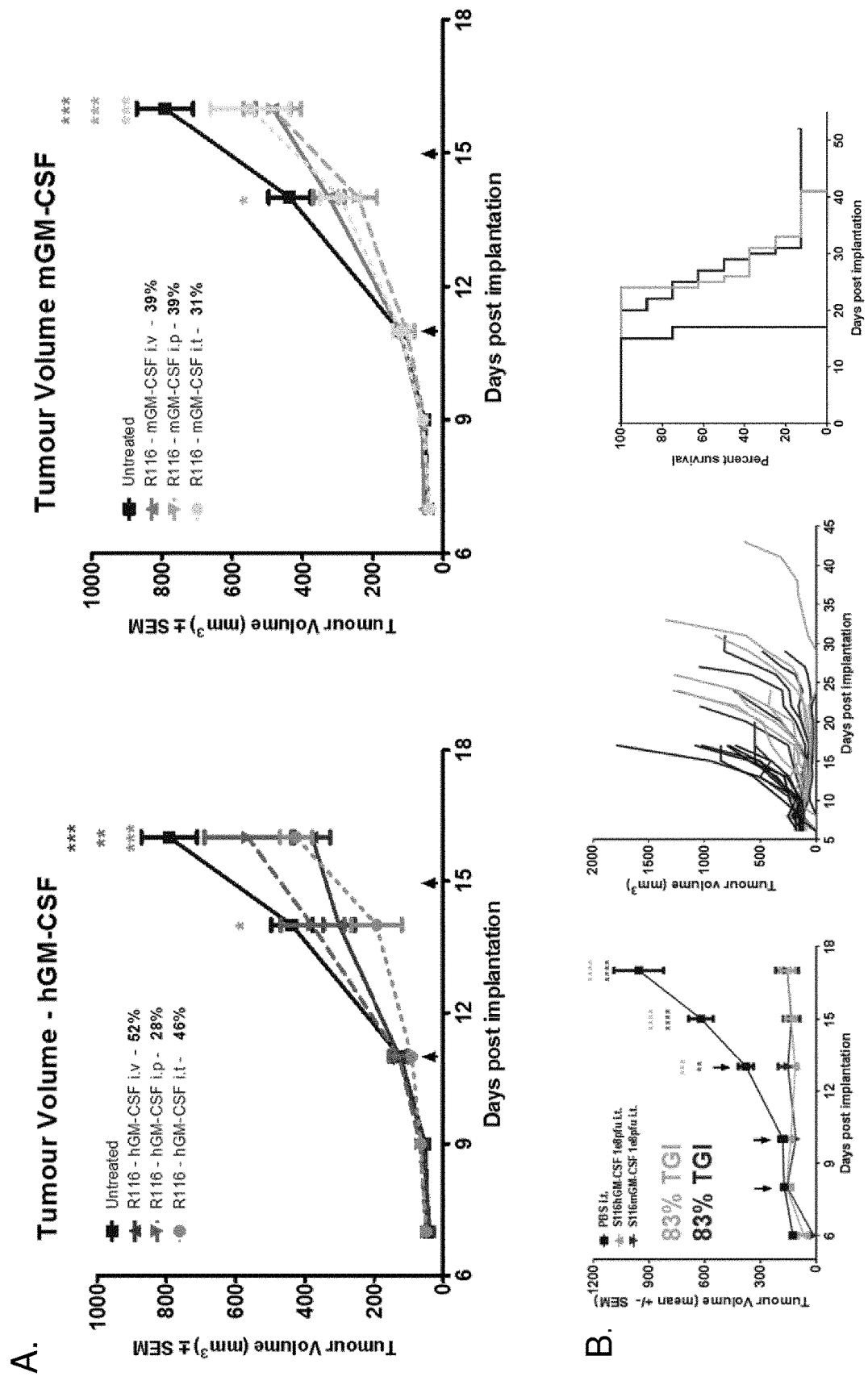
Figures 15A and B. Tumour growth inhibition in syngeneic mouse melanoma model (B16F10 AP3) by recNDV$^{GM\text{-}CSF}$ Figure 15C: NDV has potent anti-tumour activity in immune-competent mouse CT26 colorectal tumour model
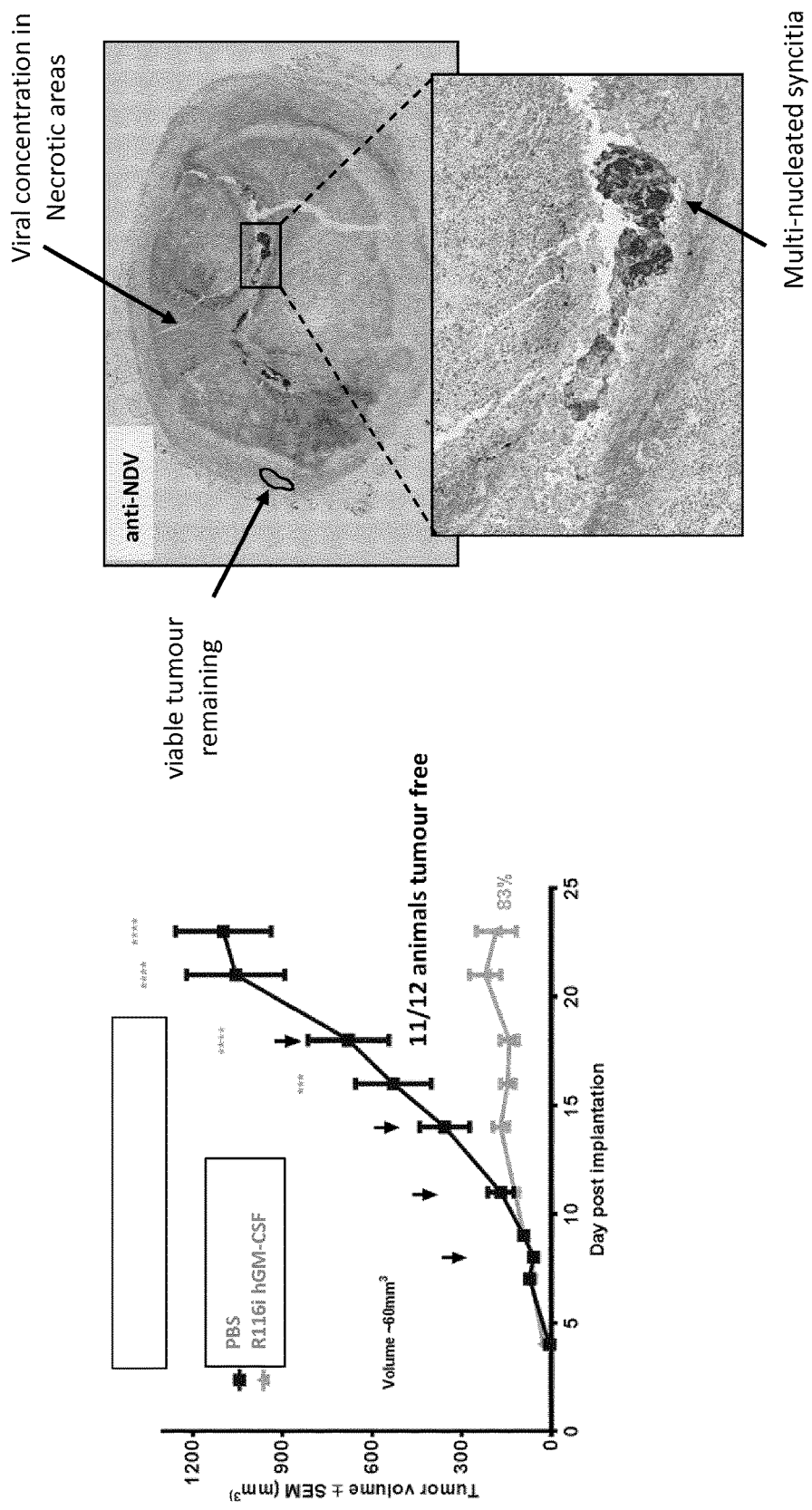

Figures 15D-F Multiple dosing with rNDV R116i causes Tumour growth inhibition and drives immune cell recruitment into ovarian cancer (OVCAR4) xenograft model
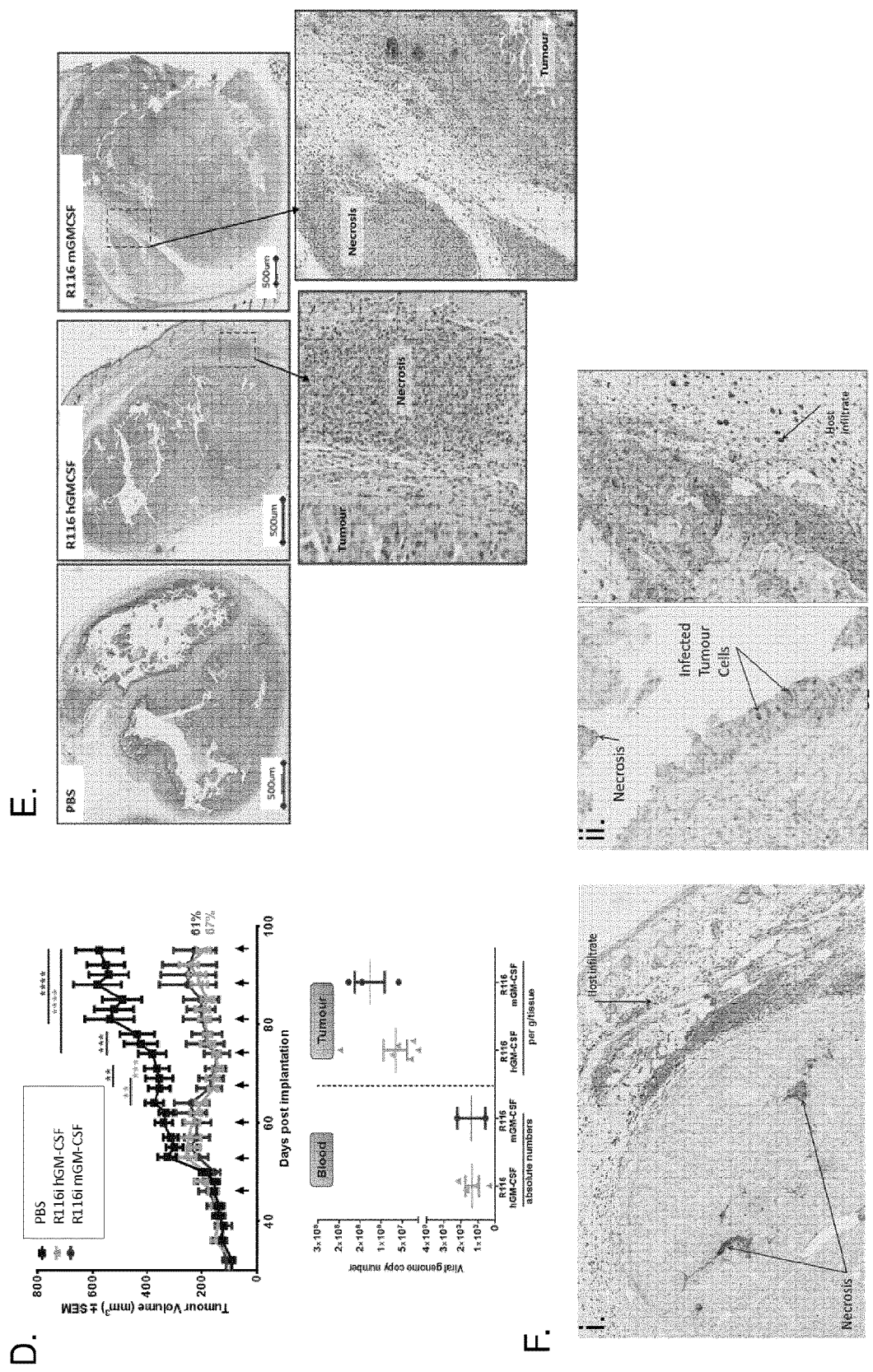

Figure 16. Summary of NDV Constructs

| FPCS (R-R-Q-K-$R^{116}$/F) | Plaques in Vero (no trypsin) | Transgene | HT1080 killing (%) at 72h | ICPI | comments |
|---|---|---|---|---|---|
| Lento (G-R-Q-E-R/L) |  | hGM-CSF | 20 | 0.0 | Replication depends on trypsin |
| S116 (N-R-T-K-S/F) | 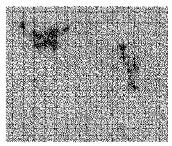  | none | 60 | 0.0 | Do not need trypsin for intro replications |
| | | hGM-CSF | 40 | 0.075 | Larger plaques |
| R116 (N-R-T-K-R/F) | 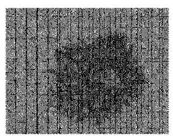  | none | 80 | tbd | Big plaques, more efficient cell killing |
| | | hGM-CSF | 80 | 0.65 | |
| S116K113M114 (N-K-M-K-S/F) | 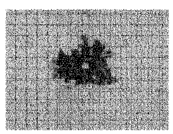  | hGM-CSF | 48 | 0.00 | Big plaques, intermediate efficient cell killing |
| R116-HN/L(318nt) (N-R-T-K-R/F) |  | hGM-CSF | 80 | 0.05 - 0.27 | 2 loci control virus *att* |
| R116-HN/L(198nt) (N-R-T-K-R/F) |  | hGM-CSF | 86 | 0.0375 | F cleavage and intergenic stretch |

All strains have titers of 8-9 $log_{10}$PFU/ml in eggs and ~7.0 $log_{10}$PFU/ml in Vero cells, lento cleavage site: 3 $log_{10}$PFU/ml in Vero.

Figure 17. NDV produced from Hela cells is less sensitive to C' mediated inactivation

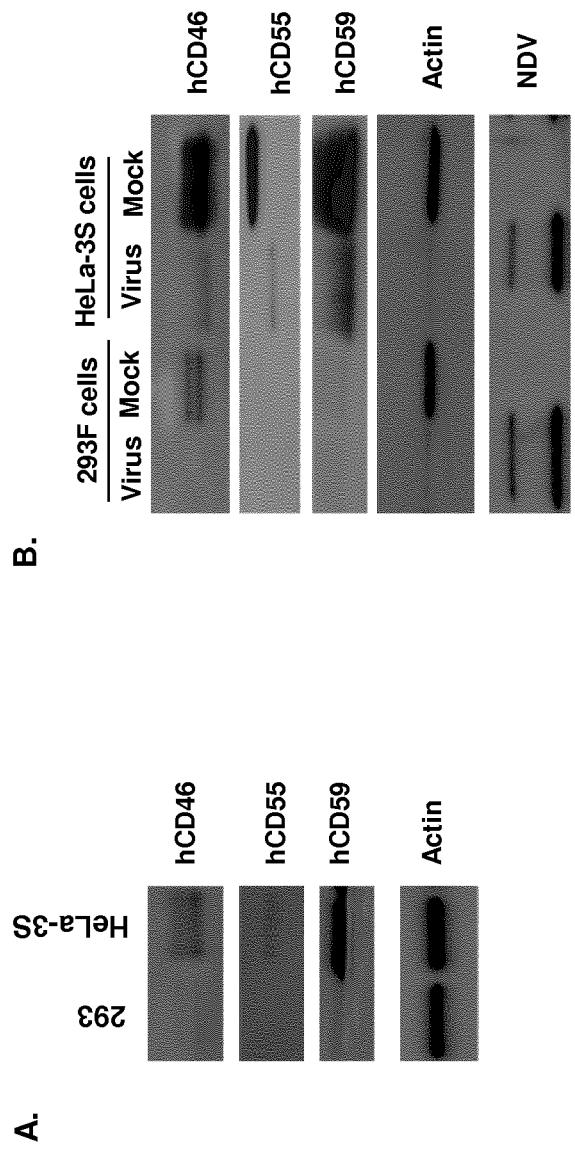
Figure 18. HeLa-3S cells express higher levels of RCA proteins than 293 cells

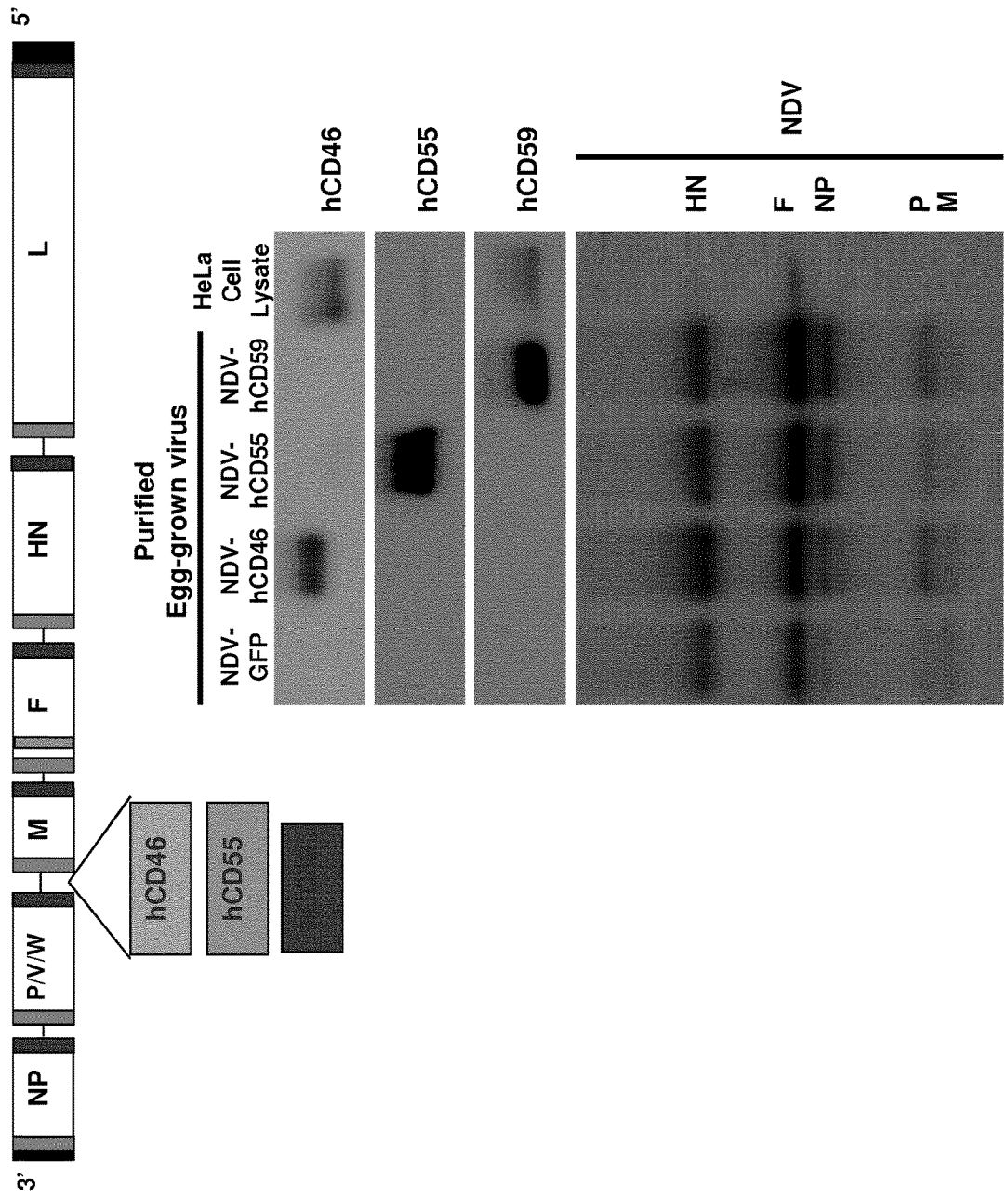
Figure 19. Expression of RCA protein by NDV

Figure 20. CD55 is a critical RCA protein for preventing C' inactivation of NDV

COMPOSITIONS FEATURING AN ATTENUATED NEWCASTLE DISEASE VIRUS AND METHODS OF USE FOR TREATING NEOPLASIA

CROSS REFERENCE TO RELATED APPLICATIONS

This application is a U.S. National Stage application of International Application No. PCT/EP2014/068619, filed on Sep. 2, 2014, said International Application No. PCT/EP2014/068619 claims benefit under 35 U.S.C. § 119(e) of U.S. Provisional Application Ser. No. 61/873,039, filed on Sep. 3, 2013, the contents of which are incorporated herein by reference.

REFERENCE TO THE SEQUENCE LISTING

This application incorporates by reference a Sequence Listing submitted with this application as a text file entitled NDV-100WO1_Sequence_Listing.TXT, created on Feb. 18, 2016, and having a size of 63.2 kilobytes.

BACKGROUND OF THE INVENTION

Newcastle disease virus (NDV) is an avian virus causing a contagious bird disease affecting many domestic and wild avian species. Exposure of humans to infected birds (e.g., in poultry processing plants) can cause mild conjunctivitis and influenza-like symptoms, but NDV otherwise poses no hazard to human health and most people are seronegative for NDV. Based on viral pathogenicity in chickens, NDV pathogenicity is classified as high (velogenic), medium (mesogenic) or low (lentogenic) as determined by the intracerebral pathogenicity index (ICPI). Due to agricultural concerns, the mesogenic and velogenic NDV having chicken virulence (ICPI>0.7) have been classified by the USDA as "select agents" since 2008. The Select Agents and Toxin List includes biological agents having the potential to pose a severe threat to human and animal health, to plant health, or to animal and plant products Naturally occurring forms of NDV have been used in clinical studies as an immunotherapeutic and virotherapeutic biologic. NDV shows promise as an anticancer agent because of the virus' ability to selectively kill human tumor cells with limited toxicity to normal cells. However, due to the reclassification of NDV as a select agent, the development of NDV as an anti-cancer agent has failed to progress. Other oncolytic viruses have shown considerable promise in clinical trials. To facilitate the development of NDV as a cancer therapy, new forms of the virus are required. Ideally, such new forms would retain their ability to target tumor cells, but would no longer cause disease in birds.

SUMMARY OF THE INVENTION

As described below, the present invention features compositions and methods for the treatment of neoplasia.

In one aspect the invention generally provides an attenuated Newcastle disease virus (NDV) having an F protein cleavage site of NDV LaSota strain or glycoprotein B (gB) of cytomegalovirus (CMV) (S116). In one embodiment of the invention the modified F protein cleavage sequence (FPCS) has one of the following sequence modifications S116: 111H-N-R-T-K-S/F117 (SEQ ID NO: 1); S116K: 111H-N-K-T-K-S/F117 (SEQ ID NO: 2); S116M: 111H-N-R-M-K-S/F117 (SEQ ID NO: 3); S116KM: 111H-N-K-M-K-S/F-I118 (SEQ ID NO: 4); or R116: 111H-N-R-T-K-R/F-I118 (SEQ ID NO: 5). In another embodiment the attenuated virus strain is a modified 73T strain. In yet another embodiment the attenuated NDV virus is r73T-R116 virus. In further embodiments the virus has an increased HN-L intergenic region. In yet other embodiments the HN-L intergenic region is a non-coding sequence between at least about 50-300 amino nucleotides in length. In further embodiments the non-coding sequence is derived from a paramyxoviruses type-1 (APMV-1), a respiratory syncytial virus (RSV) or a random sequence. In yet another embodiment the HN and L intergenic non-coding sequence is 60, 102, 144, 198, or 318 nt in length. In additional embodiments the virus has one or more heterologous polynucleotide sequences inserted at the P-M junction and/or the HN-L junction. In further embodiments the virus has two or more heterologous polynucleotide sequences, wherein at least one heterologous polynucleotide sequence is inserted at the P-M junction and at least one is inserted at the HN-L junction. In other embodiments the heterologous polynucleotide sequence is a transgene encoding a polypeptide that enhances the oncolytic properties of the virus. In yet another embodiment the transgene encodes a cytokine, cell surface ligand, and/or chemokine. In other embodiments the cytokine is selected from the group consisting of GM-CSF, IL-2, IL-21, IL-15, IL-12, and IL-12p70. In particular embodiments the cytokine is human GM-CSF. In other embodiments the heterologous polynucleotide sequence is a transgene encoding a detectable moiety. In certain embodiments the expression level of the detectable moiety correlates with virus replication. In yet another embodiment the F and HN genes of NDV are replaced by corresponding extracellular domains of canine Parainfluenza virus 5 (PIV 5) or pigeon paramyxovirus type 1 (PPMV-1). In another particular embodiment the virus is 73T-R116i-hGM-CSF. In other embodiments the attenuated virus has a Mean death time in eggs (MDT) of greater than 90 hr or about 90-156 hours. In another embodiment the attenuated virus has an intracerebral pathogenicity index between about 0-0.7. In additional embodiments the attenuated virus has an intracerebral pathogenicity index of about 0. In yet another embodiment the attenuated virus has less than about 15% cytotoxicity in HT1080 cells. In further embodiments the attenuated virus selectively kills tumor cells with killing efficiency at least 10 or 15%. In another embodiment the tumor cell killing efficiency in between about 75%-100%.

Another aspect of the invention generally features a method of selectively killing tumor cells, involving contacting a tumor cell with the attenuated Newcastle disease virus described herein. In another embodiment of the invention the tumor cell is a cell of a cancer of bladder, ovarian, brain, pancreas, prostate, sarcoma, lung, breast, cervical, liver, head and neck, gastric, kidney, melanoma, lymphoma, leukemia, thyroid, colon, and melanoma cancer cells. In yet another embodiment the method involves administering to the subject an effective amount of an attenuated Newcastle disease virus described herein. In yet another embodiment the attenuated Newcastle disease virus is delivered systemically, intraperitoneally, or intratumorally. In further embodiments virus is administered at a dose of about $10^7$ pfu to about $10^9$ pfu. In additional embodiments the virus is administered intravenously at a dose of about $10^9$ pfu to about $10^{11}$ pfu. In further embodiments the subject has a cancer selected from the group consisting of bladder, ovarian, brain, pancreas, prostate, sarcoma, lung, breast, cervical, liver, head and neck, gastric, kidney, melanoma, lymphoma, leukemia, thyroid, colon, and melanoma cancer.

In yet another aspect the invention generally features a method of treating a neoplasia in a subject that has developed an anti-NDV immune response, the method involving administering to the subject an effective amount of an attenuated chimeric Newcastle disease virus described herein, wherein the virus is a chimeric virus comprising a F and/or HN gene of a canine Parainfluenza virus 5 (PIV 5) or Pigeon paramyxovirus type 1 (PPMV-1), wherein the chimeric Newcastle disease virus is antigenically distinct from NDV. In an embodiment of the invention the method increases the level of oncolytic viruses present in the subject relative to the level of oncolytic viruses present in a control subject that has developed an anti-NDV immune response, but that is not receiving a chimeric Newcastle disease virus.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "attenuated Newcastle disease virus" is meant a Newcastle disease virus that selectively kills tumor cells but that does not pose a threat to poultry. In one embodiment, an attenuated Newcastle disease virus has an ICPI less than about 0.4 or 0.7. In other embodiments, attenuated Newcastle disease virus has an ICPI of between about 0 and 0.1.

By "heterologous polynucleotide sequence" is meant a recombinant polynucleotide that is not present in the wild-type condition.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "agent" is meant any small molecule chemical compound, antibody, nucleic acid molecule, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions, or variable chain polypeptides, of each light/heavy chain pair form an antibody binding site.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "biologic sample" is meant a sample obtained from a subject including a sample of biological tissue or fluid origin, obtained or collected in vivo or in situ. In particular embodiments, a biological sample includes any cell, tissue, fluid, or other material derived from an organism.

By "capture reagent" is meant a reagent that specifically binds a nucleic acid molecule or polypeptide to select or isolate the nucleic acid molecule or polypeptide.

By "clinical aggressiveness" is meant the severity of the neoplasia. Aggressive neoplasia are more likely to metastasize than less aggressive neoplasia. While conservative methods of treatment are appropriate for less aggressive neoplasia, more aggressive neoplasia require more aggressive therapeutic regimens.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The term "reduce" or "increase" is meant to alter negatively or positively, respectively. An alteration may be by 5%, 10%, 25%, 30%, 50%, 75%, or even by 100%.

By "reference" is meant a standard of comparison.

By "periodic" is meant at regular intervals. Periodic patient monitoring includes, for example, a schedule of tests that are administered daily, bi-weekly, bi-monthly, monthly, bi-annually, or annually.

By "severity of neoplasia" is meant the degree of pathology. The severity of a neoplasia increases, for example, as the stage or grade of the neoplasia increases.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 .mu.g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, "substantially pure" means that a species of interest is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the species of interest is purified to essential homogeneity (contaminant species cannot be detected in the composition by conventional detection methods) wherein the composition consists essentially of a single macromolecular species.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. Thus, a successful treatment may prolong the survival of a patient or alleviate an undesirable symptom.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

A dose refers to a single administration of a therapeutic composition. Dosage refers to the amount of a therapeutically active molecule in a dose. A treatment regimen refers to the dosage, schedule, and mode of administration of one or more doses. A cycle refers to a repeatable unit of one or more doses within a treatment regimen. In some treatment regimens dosages are uniform for each dose. In other treatment regimens, the dosages may not be uniform. For example, one or more loading doses may be used to raise the concentration of a therapeutic molecule to a desired level in a patient. Loading doses may be followed by one or more maintenance doses, generally comprising lower dosages (for example one half or less of a loading dose) which are sufficient to maintain a desired concentration of a therapeutic molecule in a patient. One or more tapering doses may be used to gradually reduce the concentration of a therapeutic molecule in a patient.

By "specifically binds" is meant a compound (e.g., antibody) that recognizes and binds a molecule (e.g., polypeptide), but which does not substantially recognize and bind other molecules.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

SEQUENCES

An exemplary nucleotide sequence of full-length NDV virus 73T is:

```
                                                        (SEQ ID NO: 6)
tacgtataatacgactcactatagggaccaaacagagaatccgtaggttacgataaaaggcgaaggagca attgaagttggacgggtagaaggtgtgaatctcgagtgcgagcccgaagcacaaactcgagaaagccttc tgccaacatgtcttccgtatttgacgagtacgaacagctcctcgcgtctcagactcgcccaatggagct catggaggaggggaaaaggggagtaccttaaaagtagacgtcccggtattcactcttaacagtgatgacc cagaagataggtggaactttgcggtattctgcctccggattgctgttagcgaagatgccaacaaaccact caggcaaggtgctctcatatctcttttatgctcccactcacaagtgatgaggaaccatgttgcccttgca gggaaacagaatgaagccacattggccgtgcttgagattgatggctttgccaacggtatgcccagttca acaataggagtggagtgtctgaagagagagcacagagattcgcgatgatagcagggtctctccctcgggc atgcagtaatggcaccccgttcgtcacagccggggccgaagatgatgcaccagaagacatcaccgatacc ctggagaggatcctctctatccaggcccaagtatgggtcacagtagcaaaagccatgactgcgtatgaga ctgcagatgagtcagaaacaagacgaatcaataagtatatgcagcaaggcagggtccaaaagaaatacat cctctaccccgtatgcaggagcacaatccaactcacgatcagacagtctcttgcagtccgcatcttttg gttagcgagctcaagagaggccgcaacacggcaggtggtacctctacttattataacctagtaggggacg tagactcatatatcaggaataccgggcttactgcattcttcctgacactcaagtacggaatcaacaccaa gacatcagcccttgcacttagtagcctctcaggcgacatccagaagatgaagcagctcatgcgtttgtat cggatgaaaggagataatgcgccgtacatgacattgcttggtgatagtgaccagatgagctttgcgcctg ccgagtatgcacaactttactccttcgccatgggtatggcatcagtcctagataaaggtaccgggaaata ccaatttgccagggactttatgagcacatcattctggagacttggagtagagtacgctcaggctcaggga agtagcattaacgaggatatggctgccgagctaaagctaaccccagcagcaaggagaggcctggcagctg ctgcccaacgagtctccgaggagaccagcagcatagacatgcctactcaacaagtcggagtcctcactgg gctcagcgagggggggtcccaagccctacaaggcggatcgaatagatcgcaagggcaaccagaagccggg gatggggagacccaattcctggatctgatgagagcggtagcaaatagcatgagggaagcgccaaactctg cacagggcactccccaatcggggcctcccccaactcctgggccatcccaagataacgacaccgactgggg gtattgattgacaaaacccagcttgcttccacaaaatcatcccaataccctcaccgtagtcgacccctc gatttgcggccctacatgaccacaccctcaaacaaacatcccctcttcctccctcccctgctgtaca actccgcacgccctaggtaccacaggcacaatgcggctcactaacaatcaaaacagagccgaggaaatta gaaaaagtacgggtagaagagggatattcagagaccagggcaagtctcccgagtctctgctctctcctc tacctgatagattaggacaaatatggccacctttacagatgcggagatcgacgagctatttgagacaagt ggaactgtcattgacaacataattacagcccagggtaaaccagcagagactgtgggaaggagtgcaatcc
```

-continued

```
cacatggcaaaaccaaggcgctgagcgcagcatgggagaagcatgggagcatccagccaccagccagtca agacaccctgatcgacaggacagatctgacaaacaaccatccacacccgagcaagcgacccgcatgac agcccgccggccacatccgccgaccagccccccacccaggccacagacgaagccgtcgacacacagctca ggaccggagcaagcaactctctgctgttgatgcttgacaagctcagcaataaatcatccaatgctaaaaa gggcccatggtcgagccccaagaggggaaccaccaacgtccgactcaacagcagggaagtcaacccagc cgcggaaacagtcaggaaagaccacagaaccaagtcaaggccgccctggaaaccagggcacagacgcga acacagcatatcatggacaatggggaggagtcacaactatcagctggtgcaacccctcatgctctccgatc aaggcagagccaagacaataccctgtatctgcggatcatgtccagccacctgtagactttgtgcaagcg atgatgtctatgatggaggcaatatcacagagagtaagtaaggttgactatcagctagatcttgtcttga aacagacatcctccatccctatgatgcggtccgaaatccaacagctgaaaacatctgttgcagtcatgga agccaatttgggaatgatgaagattctggatcccggttgtgccaacgtttcatctctgagtgatctacgg gcagttgcccgatctcacccggttttagtttcaggccctggagacccatctccctatgtgactcaaggag gcgaaatggcacttaataaactttcgcaaccagtgccacatccatctgaattgattaaacccgccactgc atgcgggcctgatataggagtggaaaaggacactgtccgtgcattgatcatgtcacgcccaatgcacccg agttcttcagccaagctcctaagcaagctagatgcagccgggtcgatcgaggaaatcaggaaaatcaagc gccttgcactaaatggctaattaccactgccacacgtagcgggtccccgtccactcggcatcacacggaa tctgcaccgagtcccccccgcagacctaaggtccaactctccaagtggcaatcctctctcgcttcctca gccccactgaatgatcgcgcaaccgtaattaatctagctacattaaggattaagaaaaaatacgggtaga attggaatgccccaattgtgccaagatggactcatctaggacaattgggctgtactttgattctgcccat tcttctagcaacctgttagcatttccgatcgtcctacaagacacaggagatgggaagaagcaaatcgccc cgcaatataggatccagcgccttgactcgtggactgatagtaaagaagactcagtattcatcaccaccta tggattcatctttcaggttgggaatgaagaagccactgtcggcatgatcaatgataatcccaagcgcgag ttactttccgctgcgatgctctgcctaggaagcgtcccaaataccggagaccttgttgagctggcaaggg cctgtctcactatggtagtcacatgcaagaagagtgcaactaatactgagagaatggttttctcagtagt gcaggcaccccgagtgctgcaaagctgtagggctgtggcagacaaatactcatcagcgaatgcagtcaag cacgtgaaagcgccagagaagatccccgggagtggaaccctagaatacaaggtgaactttgtctccttga ctgtggtaccgaagaaggatgtctacaagatcccaactgcagtattgaaggtttctggctcgagtctgta caatcttgcgctcaatgtcactattaatgtggaggtagacccgaggagtcctttggttaaatctctgtct aagtctgacagcggatactatgctgacctcttcttgcatattggacttatgaccaccgtagataggaagg ggaagaaagtgacttttgacaagctagaaaagaagataaggagacttgatctatctgtcgggctcagtga tgtgctcggaccttccgtgctggtaaaagcaagaggtgcacggaccaagcttttggcaccttttcttctct agcagtgggacagcctgctatcccatagcaaatgcctctcccaggtggccaagatactctggagtcaaa ccgcgtgcctgcggagcgttaaaatcattatccaagcaggtacccaacgcgctgtcgcagtgaccgctga ccacgaggttacctctactaagctggagaaggggcacacccttgccaaatacaatccttttaagaaataa gctgcgtttctgagattgcgctccgcccactcacccagagcatcatgacaccaaaaactaatctgtcttg attatttacagttagtttacctgtctatcaaattagaaaaaacacgggtagaagattctggatcccggtt ggcgccttctaggtgcaagatgggccccagaccttctaccaagaacccagcacctatgatgctgactgtc cgggtcgcgctggtactgagttgcatctgtccggcaaactccattgatggcaggcctcttgcggctgcag gaattgtggtaacaggagacaaagcagtcaacatatacacctcatcccagacaggatcaatcatagttaa gctcctcccaaacctgcccaaggataaggaggcatgtgcgaaagccccttggatgcatacaacaggaca ttgaccactttgctcacccccccttggtgactctatccgtaggatacaagagtctgtaactacatctggag
```

-continued

```
ggaggagacagaaacgctttataggcgccattattggcggtgtggctcttggagttgcaactgctgcaca ataacagcggccgcagctctgatacaagccaaacaaaatgctgccaacatcctccgacttaaagagagc attgccgcaaccaatgaggccgtgcatgaggtcactgacggattatcgcaactagcagtggcagttggga agatgcagcagtttgtcaatgaccaatttaataaaacaactcaggaattaggctgcatcagaattgcaca gcaagttggcgtagagctcaacctgtatctaaccgaattgactacagtattcggaccacaaatcacttca cctgccttaaacaagctgactattcaggcactttacaatctagctggtgggaatatggatcacttgttga ctaagttaggtgtagggaacaatcaactcagctcattaatcggtagcggcttaatcaccggcaaccctat tctgtacgactcacagactcaactcttgggtatacaggtaactctaccttcagtcgggaacctaaataat atgcgtgccacctacttggaaaccttatccgtaagcacaaccaggggatttgcctcggcacttgtcccaa aagtggtgacacaggtcggttctgtgatagaagaacttgacacctcatattgtatagaaaccgacttgga tttatattgtacaagaatagtaacattccctatgtccctggtatttattcctgcttgagcggcaataca tcggcctgtatgtactcaaagaccgaaggcgcactcactacgccatacatgactatcaaaggctcagtca tcgctaactgcaagatgacaacatgtagatgtgtaaacccccgggtatcatatcgcaaaactatgggga agccgtgtctctaatagataagcaatcatgcaatgttttatccttagacgggataactttaaggctcagt ggggaattcgatgcaacttatcagaagaatatctcaatacaagattctcaagtaataataacaggcaatc ttgatatctcaactgagcttgggaatgtcaacaactcgatcagtaatgctttgaataagttagaggaaag caacagcaaactagacaaagtcaatgtcaaactgaccagcacatctgctctcattacctatatcgttttg actatcatatctcttgtttttggtatacttagcctggttctagcatgctacctaatgtacaagcaaaagg cgcaacaaaagaccttattatggcttgggaataatacccctagatcagatgagagccactacaaaaatgtg aacacagatgaggaacgaaggtatccctaatagtaatttgtgtgaaagttctggtagtctgtcagttcgg agagtttagaaaaaactaccggttgtagatgaccaaaggacgatatacgggtagaacggtaagagaggcc gccccctcaattgcgagccgggcttcacaacctccgttctaccgcttcaccgacagcagtcctcagtcatg gaccgcgcagttagccaagttgcgttagagaatgatgaaagagaggcaaaaaatacatggcgcttgatat tccggattgcaatcttactcttaacagtagtgaccttagctacatctgtagcctcccttgtatatagcat gggggctagcacacctagcgaccttgtaggcataccgaccaggatttccagggcagaagaaaaaattaca tctgcacttggttccaatcaagatgtagtagataggatatataagcaagtggcccttgagtctccgttgg cattgttaaacactgagatcacaattatgaacgcaataacatctctctcttatcagattaatggagctgc gaacaacagcgggtgggggcacctatccatgacccagattttatcggggggataggcaaagaactcatt gtagatgatgctagtgatgtcacatcattctatccctctgcatttcaagaacatctgaatttttatcccgg cgcctactacaggatcaggttgcactcggttaccttcatttgacatgagtgctacccattactgctacac tcataatgtaatattgtctggatgcagagatcactcacactcacatcagtatttagcacttggtgtgctc cggacatctgcaacagggaggatattctttctactctgcgttccatcaatctggatgacacccaaaatc ggaagtcttgcagtgtgagtgcaactcccttaggttgtgatatgctgtgctcgaaagtcacggagacaga ggaagaagattataactcagctgtccctacgctgatggtacatgggaggttagggttcgacggccaatac cacgaaaaggacctagacgtcacaacattatttgaggactgggtggccaactacccaggagtaggggggtg gatcttttattgacagccgcgtatggttctcagtctacggagggctgaaacccaactcacccagtgacac tgtacaggaagagaaatatgtaatatacaagcgatacaatgacacatgcccagatgagcaagactaccag atccgaatggccaagtcttcgtataagcccgggcggtttggtgggaaacgcatacagcaggctatcttat ctatcaaggtgtcaacatctttgggcgaagacccagtactgactgtaccgcccaacacagtcacactcat ggggggccgaaggcagaattctcacagtagggacatctcatttcttgtatcagcgagggtcatcatacttc
```

-continued

```
tctcccgcgttattatatcctatgacagtcagcaacaaaacagccactcttcatagtccctatacattca atgccttcactcggccaggtagtatcccttgccaggcttcagcaagatgccccaactcgtgtgttactgg agtctatacagatccatatcccctaatcttctataggaaccacaccttgcgaggggtattcgggacaatg cttgatggtgtacaagcaagactcaatcctgcgtctgcagtattcgacagcacatcccgcagtcgcacaa cccgagtgagttcaagcagcaccaaagcagcatacacaacatcaacctgttttaaagttgtcaagaccaa taagacctattgtctcagcattgctgaaatatctaatactctctttggagaattcagaatcgtcccgtta ctagttgagatcctcaaaaatgatggggttagagaagccaggtctggttagttgagtcaactatgaaaga gctggaaagatggcattgtatcacctatcttccgcgacaccaagaatcaaactgaatgccggtgtgagct cgaattccatgtcgccagttgactacaatcagccagtgctcatgcgatcagatcaagtcttgtcaatagt ccctcgattaagaaaaaatgtaagtggcaatgagatacaaggcaaaacagctcatggtaaatagtacggg taggacatggcgagctctggtcctgaaagggcagagcatcagattatcctaccagagtcacacctgtctt caccattggtcaagcacaaactactttattactggaaattaactgggttaccgcttcctgatgaatgtga cttcgaccacctcattctcagcagacaatggaaaaaatacttgaatcggcctctcctgatactgagaga atgataaaactcggaagggcagtacaccaaactctcaaccacaattctagaataaccggagtactccacc ccaggtgtttagaagaactggctagtattgagtcccctgattcaaccaacaaatttcggaagattgagaa gaagatccaaattcacaacacgagatatggagaaatgttcacaaggctgtgtacgcatatagagaagaaa ctgctggggtcatcctggtctaacaatgtcccccggtcagaggagttcaacagcatccgtacggatccgg cattctggtttcactcaaaatggtccacagccaagtttgcatggctccatataaaacagatccagaggca tctgattgtggcagctaggacaagggctgcggccaacaaattggtgatgctaacccataaggtaggccaa gtctttgtcactcctgaacttgtcattgtgacgcatacgaatgagaacaagttcacatgtcttacccagg aacttgtattgatgtatgcagatatgatggagggcagagatatggtcaacataatatcaaccacggcggt gcatctcagaagcttatcagagaaattgatgacattttgcagttaatagacgctctggcaaaagacttg ggtaatcaagtctacgatgttgtatcactaatggagggatttgcatacggagctgtccagctgctcgagc cgtcaggtacatttgcaggagatttcttcgcattcaacctgcaggagcttaaagacattctaatcggcct cctccccaatgatatagcagaatccgtgactcatgcaatagctactgtattctctggtttagaacagaat caagcagctgagatgttgtgcctgttgcgtctgtggggtcacccactgcttgagtcccgtattgcagcaa aggcagtcaggagccaaacgtgcgcaccgaaaatggtggactttgatatgatccttcaggtactgtcttt cttcaagggaacaatcatcaacggatacagaaagaagaatgcaggtgtgtggccgcgagtcaaagtggat acaatatatgggaaggtcattgggcaactacatgcagattcagcagagatttcacacgatatcatgttga gagagtataagagtttatctgcacttgaatttgagccatgtatagaatacgaccctgtcactaacctgag catgttcctaaaagacaaggcaatcgcacaccctaacgataattggcttgcctcgtttaggcggaacctt ctctccgaagaccagaagaaacatgtaaaagaagcaacttcgactaatcgcctcttgatagagttttag agtcaaatgattttgatccatataaagagatggaatatctgacgaccctggagtaccttagagatgacga tgtggcagtatcatactcgctcaaagagaaggaagtgaaagttaatggacggatcttcgctaagctgaca aagaagttaaggaactgtcaggtgatggcggaagggatcctagccgaccagattgcacctttcttcagg gaaatggagtcattcaggatagcatatctttgaccaagagtatgctagcgatgagtcaactgtcttttaa cagcaataagaaacgtatcactgactgtaaagaaagagtatcttcaaaccgcaatcatgatccgaagagc aagaaccgtcggagagttgcaaccttcataacgactgacctgcaaaagtactgtcttaattggagatatc agacaatcaaactgttcgctcatgccatcaaccagttgatgggcctacctcacttcttcgagtggattca cctaagactgatggacactacaatgttcgtaggagacccttcaatcctccaagtgaccctactgactgt gacctctcaagagtccctaatgatgacatatatattgtcagtgccagaggggtatcgaaggattatgtc
```

-continued

```
agaagctatggacaatgatctctattgctgcaatccaacttgctgcagctagatcgcattgtcgcgttgc ctgtatggtacagggtgataatcaagtaatagcagtaacgagagaggtaagatcagacgactctccggag atggtgttgacacagttgcatcaagccagtgataatttcttcaaggaattaattcatgtcaatcatttga ttggccataatttgaaggatcgtgaaaccatcaggtcagacacattcttcatatacagcaaacgaatctt caaagatggagcaatcctcagtcaagtcctcaaaaattcatctaaattagtactagtatcaggtgatctc agtgaaaacaccgtaatgtcctgtgccaacattgcctctactgtagcacggctatgcgagaacgggcttc ccaaggacttctgttactatttaaactatataatgagttgcgtgcagacatactttgactctgagttctc catcaccaacaattcgcacccgatcttaaccagtcgtggattgaggacatctcttttgtgcactctatat gttctgactcctgcccaattagggggacttagtaaccttcaatactcaaggctctacactagaaatatcg gtgacccggggactactgcttttgcagagatcaagcgactagaagcagtgggattactgagtcctaacat tatgactaatatcttaactaggccgcctgggaatggagattgggccagtctttgcaacgacccatactct ttcaattttgagactgttgcaagcccaaacattgttcttaagaaacatacgcaaagagtcctatttgaaa cttgttcaaatcccttattgtctggagtgcacacagaggataatgaggcagaagagaaggcattggctga attcttgcttaatcaagaggtgattcatcccgcgttgcgcatgctatcatggaggcaagctctgtaggt aggagaaagcaaattcaagggcttgttgacacaacaaacaccgtaattaagattgcacttactaggaggc cactaggcatcaagaggctgatgcggatagtcaattattctagcatgcatgcaatgctgtttagagacga tgttttttcctccaatcgatccaaccaccccttagtctcttctaatatgtgttctctgacactggcagac tatgcacggaatagaagctggtcacctttgacgggaggcaggaaaatactgggtgtatctaatcctgata cgatagaactcgtagagggtgagattcttagtgtaagcggagggtgcacaagatgtgacagcggagatga acagtttacttggttccatcttccaagcaatatagaattgaccgatgacaccagcaagaatcctccgatg agagtaccatatctcgggtcaaagacacaggagaggagagctgcctcacttgcgaaaatagctcatatgt cgccacatgtgaaggctgccctaagggcatcatccgtgttgatctgggcttatggggataatgaagtaaa ttggactgctgctcttacgattgcaaaatctcggtgtaatataaacttagagtatcttcggttattgtcc cctttacccacggctgggaatcttcaacatagactagatgacggtataactcagatgacattcacccctg catctctctacagggtgtcaccttacattcacatatccaatgattctcaaaggctattcactgaagaagg agtcaaagaggggaatgtggtttatcaacagatcatgctcttgggtttatctctaatcgaatcgatcttt ccaatgatgacaaccaggacatatgatgagatcacattgcatctacatagtaaatttagttgctgtatca gggaagcacctgttgcggttcctttcgagctacttggggtggcaccggagctaaggacagtgacctcaaa taagtttatgtatgatcctagccctgtatcggagggagacttttgcgagacttgacttagctatcttcaag agttatgagcttaatctggagtcatatcccacgatagagctaatgaacattcttcaatatccagcggga agttgattggccagtctgtggtttcttatgatgaagatacctccataaagaatgacgccataatagtgta tgacaatacccgaaattggatcagtgaagctcagaattcagatgtggtccgcttatttgaatatgcagca cttgaagtgctcctcgactgttcttaccaactctattatctgagagtaagaggcctagacaatattgtct tatatatgggtgatttatacaagaatatgccaggaattctactttccaacattgcagccacaatatctca tcccgtcattcattcaaggttacatgcagtgggcctggtcaaccatgacggatcacaccaacttgcagat acggattttatcgaaatgtctgcaaaactgttagtatcttgcactcgacgtgtgatctccggcttatatt cagggaataagtatgatctgctgttcccatctgtcttagatgataacctgaatgagaagatgcttcagct gatatcccggttatgctgtctgtacacggtactctttgctacaacaagagaaatcccgaaaataagaggc ttatctgcagaagagaaatgttcagtacttactgagtatctactgtcggatgctgtgaaaccattactta gccctgatcaggtgagctctatcatgtctcctaacataattacattcccagctaatctgtactacatgtc
```

-continued

```
tcggaagagcctcaatttgatcagggaaagggaggacagggatactatcctggcgttgttgttcccccaa
gagccattattagagttcccttctgtgcaagatattggtgctcgagtgaaagatccattcacccgacaac
ctgcggcattttttgcaagagttagatttgagtgctccagcaaggtatgacgcattcacacttagtcagat
tcatcctgagctcacatcaccaaatccggaggaagactacttagtacgatacttgttcagaggaataggg
gctgcatcctcctcttggtataaggcatcccatctcctttctgtacccgaggtaagatgtgcaagacacg
ggaactccttatacttagctgaaggaagcggagccatcatgagtcttctcgaactgcatataccacatga
aactatctattacaatacgctcttttcaaatgagatgaacccccgcagcgacatttcgggccgacccca
acccagttttttgaattcggttgtttataggaacctacaggcggaggtaacatgcaaggatggatttgtcc
aagagttccgtccactatggagagaaaatacagaggaaagcgacctgacctcagataaagcagtgggta
tattacatctgcagtgccctacagatctgtatcattgctgcattgtgacattgaaatccctccagggtcc
aatcaaagcttactagatcaactagctatcaatttatctctgattgccatgcattccttaagggagggcg
gggtagtgatcatcaaagtgttgtatgcaatgggatactactttcatctactcatgaacttgttcgctcc
gtgttccacaaaaggatacattctctctaatggttatgcatgtagaggggatatggagtgttacctggta
tttgtcatgggttacctgggcgggcctacatttgtacacgaggtggtgaggatggcaaaaactctggtgc
agcggcacggtacgcttttgtccaaatcagatgagatcacactgaccaggttattcacctcacagcggca
gcgtgtgacagacatcctatccagtccttaccaagattaataaagtacttgagaaagaatattgacact
gcgctgattgaagctggggacagcccgtccgtccattctgtgcagagagtttggtgagcacgctagcgg
acataactcagataacccagatcattgctagtcacattgacacagtcatccggtctgtgatatatgga
agctgagggtgatctcgctgacacagttttctatttaccccttacaatctctctactgacgggaaaaag
agaacatcacttaaacagtgcacgagacagatcctagaggttacaatactgggtcttagagtcgaagatc
tcaataaaataggcgatgtaatcagcctagtgcttaaaggcatgatctccatggaggaccttatcccact
aaggacatacttgaagcatagtacctgccctaaatatttgaaggctgtcctaggtattaccaaacttaaa
gaaatgtttacagacacctctgtattgtacttgactcgtgctcaacaaaaattctacatgaaaactatag
gcaatgcagtcaaaggatattacagtaactgtgactcttaacgaaaatcacatattaataggctcttttt
ctggccaattgtatccttggtgatttaattatactatgttagaaaaaagttgaactctgactccttagag
ctcgaattcgaactcaaataaatgtcttaaaaaaaggttgcgcacaattttttcttgagtgtagtcttgtc
attcaccaaatctttgtttggtggccggcatggtcccagcctcctcgctggcgccggctgggcaacattc
cgagggaccgtcccctcggtaatggcgaatgggacgtcgacagctaacaaagcccgaaggaagtgagtt
gctgctgccaccgttgagcaataactagcataaccccttggggcctctaaacgggtcttgaggggttttt
tgctgaaaggagtcgtggagacgttgtttaaac
```

An exemplary nucleotide sequence of wt F protein is, wherein the underlined sequence denotes the nucleotide sequence of the F protein cleavage site:

(SEQ ID NO: 7)

```
atgggcccagaccttctaccaagaacccagcacctatgatgctgactgt
ccgggtcgcgctggtactgagttgcatctgtccggcaaactccattgatg
gcaggcctcttgcggctgcaggaattgtggtaacaggagacaaagcagtc
aacatatacacctcatcccagacaggatcaatcatagttaagctcctccc
aaacctgcccaaggataaggaggcatgtgcgaaagccccccttggatgcat
acaacaggacattgaccactttgctcacccccttggtgactctatccgt
aggatacaagagtctgtaactacatctggagggaggagacagaaacgctt
tataggcgccattattggcggtgtggctcttggagttgcaactgctgcac
aaataacagcggccgcagctctgatacaagccaaacaaaatgctgccaac
atcctccgacttaaagagagcattgccgcaaccaatgaggccgtgcatga
ggtcactgacggattatcgcaactagcagtggcagttgggaagatgcagc
agtttgtcaatgaccaatttaataaaacaactcaggaattaggctgcatc
agaattgcacagcaagttggcgtagagctcaacctgtatctaaccgaatt
gactacagtattcggaccacaaatcacttcacctgccttaaacaagctga
ctattcaggcactttacaatctagctggtgggaatatggatcacttgttg
actaagttaggtgtagggaacaatcaactcagctcattaatcggtagcgg
```

-continued

```
cttaatcaccggcaaccctattctgtacgactcacagactcaactcttgg gtatacaggtaactctaccttcagtcgggaacctaaataatatgcgtgcc acctacttggaaaccttatccgtaagcacaaccaggggatttgcctcggc acttgtcccaaaagtggtgacacaggtcggttctgtgatagaagaacttg acacctcatattgtatagaaaccgacttggatttatattgtacaagaata gtaacattccctatgtccctggtatttattcctgcttgagcggcaatac atcggcctgtatgtactcaaagaccgaaggcgcactcactacgccataca tgactatcaaaggctcagtcatcgctaactgcaagatgacaacatgtaga tgtgtaaaccccccgggtatcatatcgcaaaactatggggaagccgtgtc tctaatagataagcaatcatgcaatgttttatccttagacgggataactt taaggctcagtggggaattcgatgcaacttatcagaagaatatctcaata caagattctcaagtaataataacaggcaatcttgatatctcaactgagct tgggaatgtcaacaactcgatcagtaatgctttgaataagttagaggaaa gcaacagcaaactagacaaagtcaatgtcaaactgaccagcacatctgct ctcattacctatatcgttttgactatcatatctcttgttttggtatact tagcctggttctagcatgctacctaatgtacaagcaaaaggcgcaacaaa agaccttattatggcttgggaataataccctagatcagatgagagccact acaaaaatgtga
```

An exemplary amino acid sequence of wild type F protein wherein the underlined sequence denotes the amino acid sequence of the F protein cleavage site:

(SEQ ID NO: 8)
```
mgprpstknpapmmltvrvalvlscicpansidgrplaaagivvtgdkav niytssqtgsiivkllpnlpkdkeacakapldaynrtltttlltplgdsir riqesvttsggrrqkrfigaiiggvalgvataaqitaaaaliqakqnaan ilrlkesiaatneavhevtdglsqlavavgkmqqfvndqfnkttqelgci riaqqvgvelnlylltelttvfgpqitspalnkltiqalynlaggnmdhll tklgvgnnqlssligsglitgnpilydsqtqllgiqvtlpsvgnlnnmra tyletlsvsttrgfasalvpkvvtqvgsvieeldtsycietdldlyctri vtfpmspgiyscsgntsacmysktegalttpymtikgsvianckmttcr cvnppgiisqnygeavslidkqscnvlsldgitlrlsgefdatyqknisi qdsqviitgnldistelgnvnnsisnalnkleesnskldkvnvkltstsa lityivltiislvfgilslvlacylmykqkaqqktllwlgnntldqmrat tkm
```

An exemplary nucleotide sequence of mouse GM-CSF is:

(SEQ ID NO: 9)
```
Atgtggctgcagaacctgctgttcctgggcatcgtggtgtacagcctgag cgcccctaccagatcccccatcaccgtgaccagaccctgaaacatgtgg aagccatcaaagaggccctgaatctgctggacgacatgcccgtgaccctg aacgaagaggtggaagtggtgtccaacgagttcagcttcaagaaactgac ctgcgtgcagacccggctgaagatctttgagcagggcctgagaggcaact tcaccaagctgaagggcgctctgaacatgaccgccagctactaccagacc tactgcccccccaccccgagacagattgcgagacacaagtgaccaccta cgccgacttcatcgacagcctgaaaaccttcctgaccgacatccccttcg agtgcaagaaacccggccagaagtga
```

An exemplary amino acid sequence of mouse GM-CSF is:

(SEQ ID NO: 10)
```
mwlqnllflgivvyslsaptrspitvtrpwkhveaikealnllddmpvtl neevevvsnefsfkkltcvqtrlkifeqglrgnftklkgalnmtasyyqt ycpptpetdcetqvttyadfidslktfltdipfeckkpgqk
```

An exemplary nucleotide sequence of human GM-CSF is:

(SEQ ID NO: 11)
```
Atgtggctgcagagcctgctgctgctgggcacagtggcctgtagcatctc tgccctgccagaagccctagccctagcacacagccctgggagcatgtga acgccatccaggaagccagacggctgctgaacctgagcagagacacagcc gccgagatgaacgagacagtggaagtgatctccgagatgttcgatctgca agagcctacctgcctgcagacccggctggaactgtacaagcagggcctga gaggcagcctgaccaagctgaagggacccctgaccatgatggccagccac tacaagcagcactgccccccacacccgagacaagctgtgccacccagat catcaccttcgagagcttcaaagagaacctgaaggacttcctgctcgtga tcccttcgactgctgggagcccgtgcaggaatga
```

An exemplary amino acid sequence of human GM-CSF is:

(SEQ ID NO: 12)
```
mwlqsllllgtvacsisaparspspstqpwehvnaiqearrllnlsrdta aemnetvevisemfdlqeptclqtrlelykqglrgsltklkgpltmmash ykqhcpptpetscatqiitfesfkenlkdfllvipfdcwepvqe
```

BRIEF DESCRIPTION OF THE DRAWINGS

FIG. 1 depicts the construction of NDV 73T antigenomic cDNA strain 73T. NDV sequences in GenBank were aligned to obtain consensus sequences to design DNA oligonucleotides for RT-PCR of the viral RNA. Six subgenomic cDNA fragments generated by high-fidelity RT-PCR were assembled in the pUC19 vector. The full length cDNA of NDV 73T was designated as p73T. The nucleotide and deduced amino acid sequence of the F protein cleavage site (FPCS) in the 73T were modified as that of the NDV LaSota strain (lentogenic, lento) and gB of cytomegalovirus (CMV) (S116). The double slash indicates the site of cleavage of the F protein. In addition, the 73T strain cDNA plasmid (p73T) contains a 27 nucleotide (nt) T7 RNA polymerase promoter at 5'end and a 189 nt containing HDV antigenome ribozyme sequence and a T7 RNA polymerase transcription-termination signal at the 3' end. To generate non-virulent NDV, the sequence encoding the protease cleavage site of the fusion protein was modified by site-directed mutagenesis as those of the non-virulent NDV LaSota strain (lentogenic, lento) or glycoprotein B (gB) of cytomegalovirus (S116). FIG. 1 discloses SEQ ID NOs: 34, 16, 35, 1, 17, and 18, respectively, in order of appearance.

FIGS. 2A and 2B depict insertion of transgene cassette(s) into the NDV 73T genome. FIG. 2A shows the insertion of a transgene at the P-M junction. An AfeI restriction site was introduced at nt 3148 in the subclone plasmid containing SacII-PmlI fragment. cDNAs encoding codon-optimized human or mouse granulocyte-macrophage colony-stimulating factor (GM-CSF) or interleukin 2 (IL-2). The inserted gene cassette contains the gene end (GE; 5'-TTAAGAAAAAA-3') (SEQ ID NO: 13), intergenic nucleotide (T), the gene start sequence (GS; 5'-ACGGG-TAGA-3') (SEQ ID NO: 14) and open reading frame (ORF) of the transgene. In addition, ten nucleotides (5'-cgccgccacc-3') were inserted upstream of the initiation site to introduce a Kozak sequence. FIG. 2A discloses the full-length sequence as SEQ ID NO: 36. The SacII-PmlI fragment from the resulting plasmid was shuffled into plasmid r73T and named as p73T-P1. Additionally, FIG. 2A shows the insertion of a transgene at the HN-L junction between the HN ORF and the gene end signal (GE) sequence of HN, an AfeI restriction site was introduced at nt 8231 in the plasmid containing the AgeI-XbaI fragment. The gene cassette was generated by PCR using a pair of phosphate sense and antisense primers (Table 4) and inserted into AfeI site. The AgI-XbaI fragment from the resulting plasmid was shuffled into plasmid p73T, yielding p73T-HN1. The full length (FL) 73T cDNA containing the transgene at P-M or HN-L junction was designated as p73T-P1 or p73T-HN1, respectively. FIG. 2B shows the insertion of two transcriptional cassettes to the P-M junction. An AfeI site was introduced at the end of the ORF of GM-CSF (nt 3619). The IL-2 ORF was amplified using a pair of phosphate sense and antisense primers containing the GE and GS sequences and inserted at the AfeI site. The SacII-PmlI fragment from the resulting plasmid including GM-CSF and IL-2 transcriptional cassettes was swapped back into plasmid r73T, yielding p73T-P2. FIG. 2B discloses SEQ ID NO: 36 and 37, respectively, in order of appearance.

FIGS. 3A-3C show the recovery of infectious recombinant NDV strain 73T (r73T) with modified FPCS and depict F protein cleavage and fusion activity in vitro. FIG. 3A shows how NDV 73T NP, P, L and antigenic cDNA (p73T-lento or p73T-S116) were cloned under the control of the T7 RNA polymerase promoter and terminator. The four plasmids were co-transfected into an RNA polymerase expressing cell line. The recovered viruses were designated as r73T-lento or r73T-S116. The r73T-lento and r73T-S116 were passaged in Vero cells with media with and without trypsin supplement. The growth of r73T-lento is trypsin dependent whereas r73T-S116 can grow in medium without trypsin supplement. To assess the genetic stability of FPCS in r73T-S116 and transgene, r73T-S116 with and without hGM-CSF at P-M junction were further passaged for 10 passages in Vero and human fibrosarcoma HT1080 cells at MOI 0.01 in media without supplement of trypsin. The mutations (R113K and/or Q114M) in the FPCS appeared at passage 7 and the S116R mutation was detected at passages 9. At passage 10, the F, HN and transgene were sequenced and no additional mutations were found. FIGS. 3B and 3C show the effect of F protein cleavage site (FPCS) mutation on cell fusion and F protein cleavage in vitro. For construction of plasmid co-expressing two transgenes, GFP and NDV F or HN genes, the protein open reading frames of NDV F or HN gene were amplified by PCR and cloned into plasmid pVitro2-neo-MCS (Invitrogen) under the control of the cytomegalovirus (CMV) promoter. 293T cells were seeded at $5\times10^5$ cell/well on 6 well plate for transfection the next day. FIG. 3B depicts cells transfected with 2 µg of NDV F plasmid DNA for one day and harvested in protein lysis buffer for Western blot analysis using anti-NDV F specific polyclonal antiserum. The NDV F protein with lentogenic cleavage site and S116 were not cleaved, only F0 was detected. The F proteins of R116 and S116-KM were partially cleaved as indicated by the appearance of the F1 protein band. FIG. 3C shows the cells that were cotransfected with different F plasmid with wt HN plasmid and that were examined for fusion formation by florescent microscope. The wt F protein was most efficient in fusion formation.

FIG. 4 is a table summarizing characteristics of r73T-lento and r73T-S116 derivatives. [a] All viruses contain hGM-CSF at the P-M junction. [b] The amino acids in the FPCS that are different from FPCS-S116 are underlined (SEQ ID NO: 21, 38-40, 4, and 5, respectively, in order of appearance). [c] Plaque formation in Vero cells without trypsin in the overlay after 36 hrs incubation and visualized under ×10 magnification. [d] Mean death time in eggs (MDT). [e] Pathogenicity of NDV in 1-day-old pathogen-free chicks by the intracerebral pathogenicity index (ICPI). The ICPI assay was performed at National Veterinary Service Laboratories (NVSL) (Ames, Iowa). [f] Cytotoxicity effect of the viruses on human fibrosarcoma HT1080 cells after infection at multiplicities of infection (MOI) of 0.01 at 72 hours postinfection. The relative percentage of surviving cells is determined by comparing each sample with untreated cells that were considered 100% viable. Data presented in the table is relative percentage of dead cells. [g] Virus grown in Vero cells after infection with MOI of 0.01 and cultured in OPTI-MEM without trypsin supplement for 3-5 days at 37° C. [h] Virus grown in chicken embryonated eggs. 10-11-day old embryonated eggs were infected with 1,000 pfu of r73T. The amniotic fluid was harvested after incubation at 37° C. for 72 hrs. The infectious virus titer was determined in Vero cells by plaque assay.

FIGS. 5A and 5B depict strategies to attenuate r73T-R116 virus virulence in chicken. FIG. 5A depicts insertion of transgenes at the P-M junction (1) and HN-L junction (2), and extension of the HN-L intergenic region by insertion of non-coding sequence (3). Insertion of the transgene cassette at P-M junction is the same as that shown in FIG. 2A. The 2nd transgene cassette contains the L gene start sequence (GS; 5'-ACGGGTAGA-3') (SEQ ID NO: 14), open reading frame (ORF) of the transgene, sequences from 3' untranslated region of the L gene (in italics) and the L gene end sequence (GE; 5'-TTAAGAAAAAA-3') (SEQ ID NO: 13). The non-coding sequences used for extending the HN-L junction were taken from paramyxoviruses type-1 (APMV-1), respiratory syncytial virus (RSV) or random sequence which does not have sequence identity or homology with known sequences. The insertion sequence can be in the range of 60-318 nt. Insertion of a 2nd transgene at HN-L allows the virus to express two transgenes (e.g., hGM-CSF and GFP). FIG. 5A discloses SEQ ID NOs: 41 and 42, respectively, in order of appearance. FIG. 5B depicts sequences (SEQ ID NO: 43-48, respectively, in order of appearance) that were inserted at the HN-L junction.

FIG. 6A is a table summarizing characteristics of r73T-R116 derivatives. [a] All viruses contain hGM-CSF at the P-M junction. [b] Sequences inserted at the HN-L junction as shown in FIG. 5B. [c] Plaque formation in Vero cells without trypsin in the overlay after 36 hrs incubation and visualized under ×10 magnification. [d] Mean death time in eggs (MDT). [e] Pathogenicity of NDV in 1-day-old pathogen-free chicks by the intracerebral pathogenicity index (ICPI). The ICPI assay was performed at National Veterinary Service Laboratories (NVSL) (Ames, Iowa). [f] Cytotoxicity effect of the viruses on human fibrosarcoma HT1080 cells after infection at multiplicities of infection (MOI) of 0.01 at 72 hours postinfection. The relative percentage of surviving cells is determined by comparing each sample with untreated cells that were considered 100% viable. Data presented in the table is relative percentage of dead cells. [g] Virus grown in Vero cells after infection with MOI of 0.01 and cultured in OPTI-MEM without trypsin supplement for 3-5 days at 37° C. [h] Virus grown in chicken embryonated eggs. 10-11-day old embryonated eggs were infected with 1000 pfu of r73T. The amniotic fluid was harvested after incubation at 37° C. for 72 hrs. The infectious titer was determined in Vero cells by plaque assay.

FIGS. 6B-6E are graphs showing the growth kinetics of recombinant NDV in DF-1 and Vero cells. DF-1 and Vero cells in six-well plates were infected with each indicated virus at a multiplicity of infection (m.o.i.) of 5.0 (single cycle, FIGS. 6B and 6C) or 0.001 (multi cycle, FIGS. 6C and 6D). The infected cell culture supernatants were collected at 10 hour intervals until 50 hours post infection, and virus titers were determined by plaque assay.

FIGS. 6F and 6G show viral RNA and protein synthesis in DF-1 cells. DF-1 cells were infected with each virus as indicated at m.o.i of 5.0, incubated for 20 h, total intracellular RNAs were extracted for Northern blot analysis (FIG. 6F) and a second set of infected cells were examined for protein synthesis by Western blotting (FIG. 6G). The RNAs were separated by electrophoresis in a formaldehyde agarose gel, transferred onto nitrocellulose membranes, and hybridized with biotin labeled RNA probes specific to the HN, NP, P, and L genes. A positive RNA probe in the L gene was used to detect viral genomic RNA. The total proteins were separated on SDS-PAGE and blotted with anti-NP, F, HN and L serum. The total proteins loaded on the gel were detected by an actin-specific antibody. Recombinant NDV R116i with 198 nt insertion between the HN and L intergenic sequence had an overall reduced RNA and protein synthesis in the DF-1 cells.

FIGS. 6H and 6I depict viral RNA and protein synthesis in Vero cells. FIG. 6H shows Northern blot analysis of RNA synthesis. Vero cells were infected with the viruses at m.o.i of 5.0, incubated for 20 h, total intracellular RNAs were extracted. The RNAs were separated by electrophoresis in a formaldehyde agarose gel, transferred onto nitrocellulose membranes, and hybridized with biotin labeled RNA probes specific to the NP and L genes or a positive sense L gene RNA to detect genomic RNA. FIG. 6I depicts Western blot analysis of viral protein synthesis in infected Vero cells. The total proteins were separated on SDS-PAGE, transferred to nitrocellulose membrane and blotted with anti-NP, F, HN and L serum. The total proteins loaded on the gel were detected by an actin-specific antibody. The R116i viruses with 198 nt insertion had reduced genomic RNA, but greatly increased NP mRNA compared to S116 and wt NDV. The L mRNA level was too low to tell the difference. The proteins upstream of the L gene were upregulated but the L protein level was reduced in Vero cells.

FIGS. 6J and 6K show comparison of protein synthesis in infected DF-1 and Vero cells at low multiplicity of infection by Western blot analysis. DF-1 and Vero cells were infected with each virus as indicated at m.o.i of 0.001, incubated for 72 h and harvested in protein lysis buffer. The total proteins were separated on SDS-PAGE, transferred to nitrocellulose membrane and blotted with anti-NP, F, HN and L serum. The proteins loaded on the gel were detected by an antibody against actin. The level of L protein was reduced in both cell lines, however, the proteins upstream of the L gene was down regulated in DF-1 cells but upregulated in Vero cells.

FIG. 6L shows viral protein synthesis in infected human cells compared to DF-1 cells. Human HT1080, Hela cells and DF-1 cells were infected with each virus as indicated at m.o.i of 5.0, incubated for 20 h and harvested in protein lysis buffer. The proteins were separated on SDS-PAGE, transferred to nitrocellulose membrane and blotted with anti-HN and anti-L serum. The HN protein expression of R116i with 198 nt insertion between the HN and L junction is increased in HT1080 and Hela cells, but decreased in DF-1 cells. The L protein was decreased in all three cell lines infected with R116i-198 or 198RSV.

FIG. 7 are graphs depicting the growth kinetics of r73T viruses in embryonated chicken eggs. To determine growth conditions for the r73T viruses, growth kinetic studies were performed in eggs. Chicken embryonated eggs were infected with 100, 1000, 10,000 or 100,000 PFU/egg of indicated viruses and incubated for 2, 3 or 4 days (73T wt, top left; R116, top right; R116i-318, middle left; R116i-198-RSV, middle right; R116i-198-random, bottom left; S116-KM, bottom right). The allantoic fluid was harvested and viral titers were determined by FFA. Inoculation of 100 FFU/egg had low titer on day 1, but reach peak titer on day 2. Overall, most viruses reached peak titers of ~8 logs/mL on Day 2 regardless of the inoculate dose used. R116i-198 has the lowest titer, low inoculum dose generated the highest yield on day 2, indicating that there might be accumulation of defective particles. R116i-318-APMV-insertion also had a lower peak titer of ~7 logs. R116i-198-RSV reached peak titer of 7.5 logs. S116 rederived by reverse genetics had no reduction in virus production in eggs. Therefore, among the R116 derivatives, the virus with RSV-198 nt insertion was a top oncolytic virus candidate in terms of growth properties in eggs.

Figure 8:
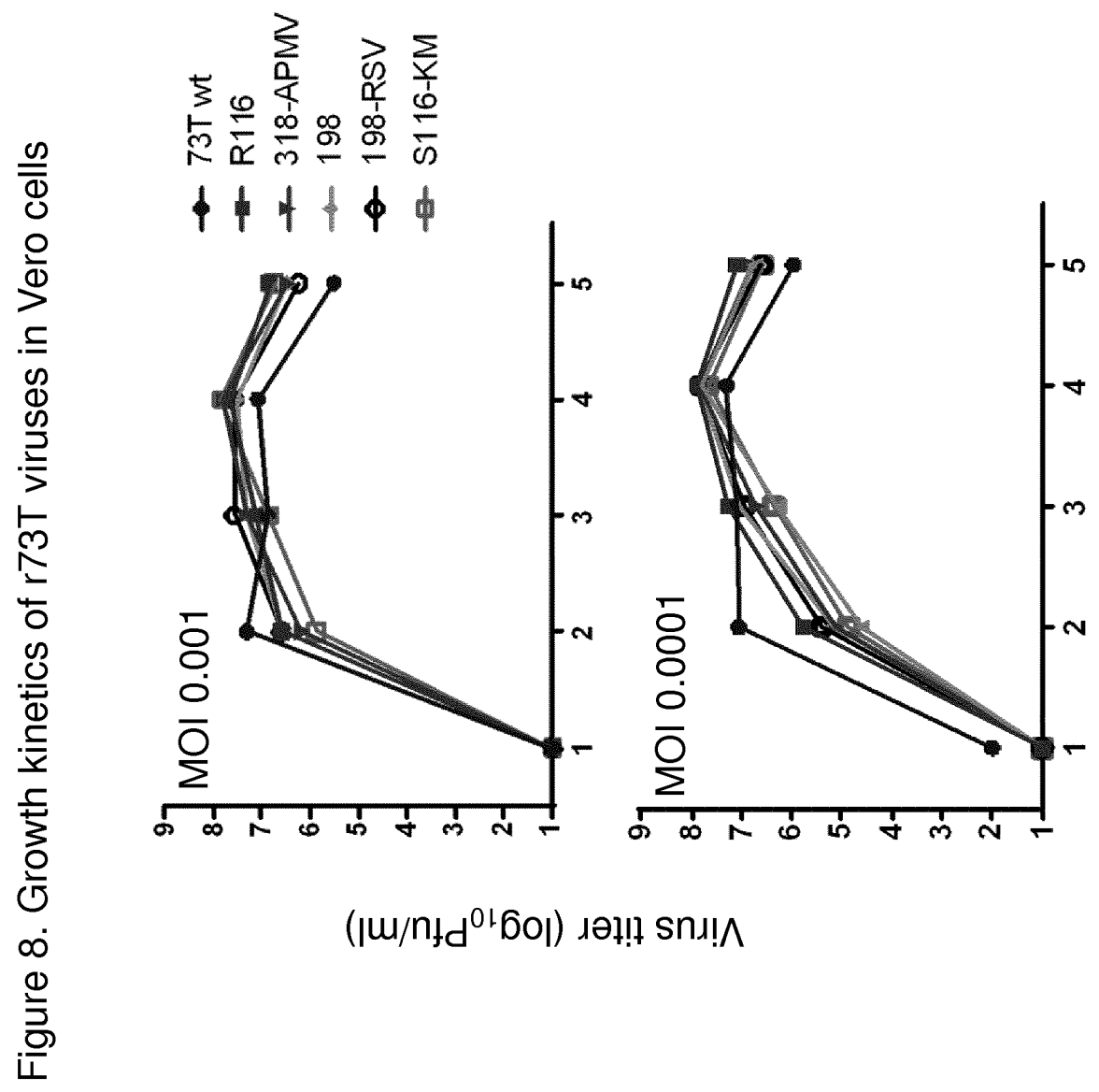

FIG. 8 are graphs depicting the growth kinetics of r73T viruses in Vero cells. The viruses were also evaluated in sero-free Vero cell clone 51D11, a proprietary cell line generated by MedImmune. All the viruses replicated similarly well under both moi conditions (0.001, top; 0.0001, bottom). The modification of 73T FPCS and intergenic insertion in the HN-L junction of R116 did not affect virus growth in Vero cells.

FIGS. 9A-9D show that r73T viruses selectively replicate in tumor cells and have cytotoxicity for tumor cells, compared to non-neoplastic cells. Data were obtained after infection with r73T derivatives at different dose ranging from 1 to 100,000 PFU for 72 hour. FIG. 9A is a graph showing the evaluation of rT3T and its derivatives for cell killing in human fibrosarcoma HT1080 relative to untreated control cells. In HT1080 cancer cells, the virus with lentogenic FPCS had the least killing, S116 at the FPCS was intermediate, and viruses with R116 at FPCS had cell killing as efficient as r73T wt virus. FIG. 9B is a graph showing the evaluation of rT3T and its derivatives for cell killing in normal human skin fibroblast CCD1122Sk cells relative to untreated control cells. In normal CCD1122SK cells, all viruses did not kill the cells as efficiently as the cancer cells, with reduction of killing efficiency of ~100-fold. Regardless of the FPCS sequences, all the viruses had similar killing in normal cells, likely due to a single cycle of replication (no virus spread). FIG. 9C is a table showing the cell killing efficiency in cancer and normal cells, expressed as 50% effective concentration ($EC_{50}$) interpolated from the dose response curve using Prism 6.0. The R116 derivative had a similar $EC_{50}$ value as r73T wt with an $EC_{50}$ of 10 PFU, indicating that the modification of FPCS did not affect virus replication in cancer cells and cell killing efficiency. FIG. 9D is a graph showing replication of the viruses in the HT1080 and CCD1122SK cells at MOI 0.01 at day 3 post infection. All viruses preferentially replicated in cancer cells than in normal cells, with a difference of about 1.5-2.0 logs.

FIGS. 10A and 10B are graphs showing r73T derivatives are effective in tumor regression upon local and systemic administration. To evaluate oncolytic activity in vivo, an HT1080 xenograft model was established by injecting HT1080 cells at a concentration of $5\times10^6$ cells/0.1 ml subcutaneously into Balb/C athymic nude mice at age of 5-6 week old. FIG. 10A is a graph showing the effect of R116i-318-hGM-CSF administered intratumorally (it) or intravenously (iv). The data show that R116i-318-hGM-CSF derivatives had anti-tumor activity in vivo when delivered either systemically or intratumorally to immunodeficient mice carrying human tumor xenografts. Tumor growth rate was compared between the treatment and the control groups. The tumor regressions induced by the two routes of administration were both significantly different from the control group. Mice were randomized into groups (n=10) as indicated when tumor volume reached approximately 65 $mm^3$. Mice received a single dose of either PBS or $2\times10^7$ Pfu of r73T-hGM-CSF-R116i-198 administered intratumorally (IT) or $1\times10^8$ PFU administered intravenously (IV) via tail vein injection. *P<0.05, un-paired student T test. FIG. 10B is a graph comparing the oncolytic activities of r73T derivatives in the HT1080 xenografts by IV injection of $1\times10^8$ PFU. Two doses of r73T derivatives were capable of inducing significant tumor regression with varying degrees of effectiveness. r73T-lento was the least effective in tumor regression whereas r73T wt was the most effective in tumor regression. r73T-lento had a similar effect as the S116 virus, although S116 virus has a 10-fold lower $EC_{50}$ in the in vitro cell killing (see FIG. 9A). r73T-R116i-318 was as potent as 73T wt in inhibition of tumor growth until 9 days post the $2^{nd}$ dose (day 19 post tumor implantation), the tumor grew back in R116i treated mice but not in the 73T wt treated group. Mice were randomized into groups (n=7) when tumor volume reached approximately 180 $mm^3$. Mice received either PBS or $1\times10^8$ PFU of r73T-hGM-CSF-lento (lento) or r73T-hGM-CSF-S116K113M114 (S116 KM) or r73T-hGM-CSF-R116i-318 nt APMV-N(R116i) or r73T-hGM-CSF (r73T wt) administered by IV. Tumor size was measured every 3-4 days. *P<0.05, un-paired student T test. The data show that r73T derivatives had anti-tumor activity in vivo when delivered either systemically or intratumorally to immunodeficient mice carrying human tumor xenografts. The efficient cleavage of the F protein is important for virus replication in vitro and in vivo. The viruses with the R116 at the FPCS were more potent in cell killing in vitro and in vivo.

FIGS. 11A-G depict the tissue biodistribution of r73T derivatives following intravenous delivery and the effect of mouse versus human GM-CSF on tumor growth inhibition. To determine if the oncolytic NDV virus selectively replicates in tumor tissues and viral clearance, virus distribution in different organs was determined. Athymic nude mice bearing subcutaneous HT1080 tumors with size of ~250 $mm^3$ were treated with R116i (r73T-hGM-CSF-R116i-318 nt APMV-N) at a dose of $1\times10^8$ PFU intravenously and sacrificed on day 1, 4 or 8 (n=3 per time point). Serum, lungs, spleen, ovaries and tumor were collected and the presence of virus was quantified. Viral replication in tumor and organs were assessed at days 1, 4 and 8 post infection.

FIG. 11A is a graph depicting quantification of virus in tissues by plaque assay in Vero cells. Virus in organs was only detected on day 1 (virus was not detected in ovary at all time points, data not shown) and virus load in tumor tissues was ~100-fold higher than lungs and spleens. The presence of virus in tumor persisted for at least 8 days, indicating that the virus selectively replicated in tumor tissues.

FIG. 11B is a graph depicting quantification of GM-CSF expressed by virus in tissues by ELISA assay of hGM-CSF transgene expression. Consistent with the viral replication data obtained by plaque assay, the level of hGM-CSF was the highest and lasted more than 8 days in the tumor tissue. These data demonstrated that the NDV virus effectively replicated in tumor tissue and that the transgene was effectively delivered to local tumor tissue.

FIG. 11C depicts graphs showing the effect of mGM-CSF expression on tumor growth inhibition in HT1080 xenograft mouse tumor model. Athymic nude mice at 5-6 weeks old in groups of seven were implanted subcutaneously (s.c.) with $5\times10^6$ HT1080 cells in the right flank. When tumors reached a volume of 110 $mm^3$ (day 6), the tumor were injected with a single dose of $1\times10^8$ pfu rNDV, R116i-198RSV with mGM-CSF or hGM-CSF. The tumor size was measured every 3-4 days. R116i-198RSV with mGM-CSF was less potent in tumor growth inhibition than hGM-CSF transgene. However, no difference in tumor growth inhibition was observed for S116 with either hGM-CSF or mGM-CSF.

FIG. 11D depicts graphs showing the effect of mGM-CSF on virus clearance from tumors in HT1080 xenograft mouse tumor model. Athymic nude mice in groups of three were implanted subcutaneously (s.c.) with $5\times10^6$ HT1080 cells into the right flank. When tumors reached a volume of 180 $mm^3$ (day 10), the mice were intravenously treated with one dose of $1\times10^8$ pfu of R116i-198RSV or S116KM. The tumors were collected on day 4 or 7 and viral titers in the tumor tissue were determined by plaque assay. Both R116i-198RSV and S116KM with either mGM-CSF or hGM-CSF had comparable titer on day 4. On day 7, R116i-198RSV with mGM-CSF was greatly reduced compared to R116i-198RSV with hGM-CSF. In comparison, the titers of S116 mGM-CSF and hGM-CSF were comparable.

FIG. 11E depicts a graph showing the effect of R116i-198RSV or S116KM infection on immune cell infiltration into tumors in HT1080 xenograft mouse tumor model. Athymic nude mice in groups of three were implanted subcutaneously (s.c.) with $5\times10^6$ HT1080 cells into the right flank. When tumors reached a volume of 180 $mm^3$ (day 10), the mice were intravenously treated with one dose of $1\times10^8$ pfu of virus as indicated. The tumors were collected on day 4 and the tissues were processed for neutrophil, NK cells and macrophage staining by FACS analysis. R: R116i-198-RSV, S: S116-KM. R116i-198RSV with mGM-CSF had more immune cell infiltration.

FIG. 11F depicts a table showing that cytokines and chemokines were up-regulated in HT1080 xenograft mouse tumor model. Athymic nude mice in groups of three were implanted subcutaneously (s.c.) with $5\times10^6$ HT1080 cells into the right flank. When the tumors reached a volume of 180 $mm^3$ (day 10), the mice were intravenously treated with one dose of $1\times10^8$ pfu of R116i-198RSV or S116KM with hGM-CSF or mGM-CSF. The tumors were collected on day 4 and the tissues were processed for levels of cytokines and chemokines by Luminex analysis. Virus infection induced cytokines and chemokines production in the local tumor tissues, their levels varied based on virus backbone and human or mouse GM-CSF.

FIG. 11G depicts a graph showing that R116i-198RSV-hGM-CSF and R116i-318APMV-hGM-CSF were comparable in tumor growth inhibition in HT1080 xenograft mouse tumor model. Athymic nude mice in groups of seven were implanted subcutaneously (s.c.) with 5×10⁶ HT1080 cells into the right flank. When tumors reached a volume of approximately 110 mm³ (day 6), a single dose of virus at 1×10⁸ pfu was injected intra-tumorally. The tumor size was measured every 3-4 days and graphed. The insertion length of 198 and 318 nt did not affect R116i oncolytic activity.

FIG. 12A and FIG. 12B depict construction of antigenome cDNA of 73T containing chimeric F and/or HN genes and their characterization and FIG. 12C compares function of RNA polymerase complex activity. Viral surface glycoproteins are important antigens for immunogenicity and virulence in chickens. F and/or HN genes of NDV were replaced by the corresponding extracellular (ecto) domains of other paramyxoviruses which are not virulent in chickens individually or in combination. Parainfluenza virus 5 (PIV 5) is a canine paramyxovirus and does not cause diseases in human, and pigeon paramyxovirus type 1 (PPMV-1) has been show to be nonvirulent in chickens. FIG. 12A shows that F and/or HN glycoprotein ectodomains of the full-length antigenomic NDV 73T cDNAs were replaced with those of PPMV-1 and/or PIV5. NDV, PIV5, and PPMV-1 sequences are indicated with colored boxes as blue, purple or green, respectively. The amino acid lengths of individual proteins or protein domains are indicated. FIG. 12A discloses SEQ ID NOs: 34, 35, and 49, respectively, in order of appearance. FIG. 12B is a table showing characterization of 73T derivatives containing chimeric F and/or HN genes. Plaque formation in Vero, relative HT1080 cell killing and MDT were performed as described previously. Chimeric viruses, except for PVI-5 F-HN, were recovered and grew in the cells in the absence of exogenous trypsin. All three viruses formed good sized plaques and showed efficient cell to cell spreading. PPMV-1 F-HN or F chimeric viruses had MDT value of 79 and 84 hr, respectively, indicating potential virulence in chickens. Both PPMI-1 chimeric virus killed HT1080 cells efficiently at levels of 71 and 61%. PIV5-F chimera did not grow in eggs and was not virulent in chickens, but killed HT1080 cells at 47%. Serum cross reactivity between the NDV and PPMV-1 or PIV5 chimeras was examined by neutralization assay using the serum collected from mice that were IV administrated with 2 doses of $1\times10^8$ PFU of r73T-R116i. r73T virus can be neutralized by the NDV-infected serum (titer 960) whereas the PPMV-1 and PIV5 chimera were not neutralized (titer <4), confirming no cross reactivity between NDV and PPMV-1 or PIV5. The chimeric viruses with distinct antigenicity could be to boost oncolytic viruses in patients for whom anti-NDV immune responses have developed during prior NDV treatment.

FIG. 12C shows the comparison of NDV RNA polymerase activity with other paramyxoviruses by mini-genome assay. The T7 expressing cells were transfected with the three plasmids expressing the NP, P, L proteins of NDV and the plasmid encoding the NDV anti-minigenomic cDNA encoding the GFP gene using Lipofectamine 2000, or the plasmids encoding N, P, L genes of measles virus (MV) or respiratory syncytial virus (RSV) and respective RSV or MV GFP anti-minigenome cDNA plasmid. Two or three days post transfection, minigenome replication as indicated by the expression of GFP proteins was examined under fluorescent microscope. The NDV had the strongest polymerase activity compared to measles virus and RSV.

FIGS. 13 A and B show cancer cell line sensitivity to rNDV variants. Cancer cell lines from various tissues of origin were infected with NDV S116 or NDV R116i at an MOI of 0.1 and cell viability was assessed 72 hrs post infection using Cell Titre Glo. Sensitivity to NDV is defined as greater than 30% cell killing at 72 hrs post infection. FIG. 13A depicts a graph of percentage of NDV sensitive human cancer cell lines across a minimum of 16 broad indications. Numbers of cell lines within each group are indicated numerically and in Table 1. FIG. 13B depicts a graph of sensitivity of 22 cancer cell lines to NDV variants. % cell kill is determined as a percentage of untreated control cells.

FIG. 14 are graphs showing permissivity of cancer cell lines to $recNDV^{GM-CSF}$. Cell killing of R116i-GM-CSF in representative tumor cell lines are presented in FIG. 14. Maximum % kill was determined 3 days following infection of tumor cell lines relative to non-infected control at MOI of 0.1. Although certain cell lines were derived from the same tumor types, such as bladder, gastric, prostate, melanoma, breast, ovarian, pancreatic and lung cancers, they showed different sensitivity to the virus killing. The numbers of cell lines from each tumor indication that can be killed by R116i-GM-CSF at rate of >50% are summarized at Table 1.

FIGS. 15A-F are graphs showing that NDV derivatives inhibit tumor growth in different mouse cancer models. FIGS. 15A and 15B are graphs showing $recNDV^{GM-CSF}$ strains inhibit tumor growth in syngeneic mouse melanoma model (B16F10 AP3). 73T-R116i-hGM-CSF (FIG. 15A left) and R116i-mGM-CSF (FIG. 15A right) were evaluated for their oncolytic effect in the B16 melanoma model in a pilot study. As virus tolerability in the B16 mouse was being evaluated, the group size was small (n=3). Each virus was dosed intravenously (i.v) at $2\times10^7$ pfu twice on days 11 and 14; intraperitoneally (i.p) at $2\times10^7$ pfu twice on days 11 and 14; or intratumorally (i.t) once at $1.1\times10^7$ pfu on day 11. The groups treated with R116-hGM-SCF or mGM-SCF by the three routes of administration had slower rate of tumor growth compared to the untreated group. Tumor inhibition rates were statistically significant from the control group.

FIG. 15B shows an efficacy study in B16F10 syngeneic murine melanoma model with intratumoural administration of $1\times10^8$ pfu of S116 NDV variants. Tumour growth inhibition is shown on the left panel and individual animal measurements are shown on the middle panel and a survival plot is shown on the right.

FIG. 15C shows that NDV has potent anti-tumour activity in immune-competent mouse CT26 colorectal tumour model. In particular, FIG. 15C provides an efficacy study in CT26 syngeneic murine colorectal model with intratumoural administration of $1\times10^8$ pfu of R116 NDV variant encoding human GM-CSF. Tumour growth inhibition is shown on the right panel and IHC analysis of the remaining tumour is shown on the right hand side with H&E and NDV staining. Necrotic areas, evidence of multinucleated syncytia and viable areas of tumours are indicated.

FIGS. 15D-F depict tumor growth inhibition in ovarian xenograft model. Athymic nude mice at were implanted subcutaneously (s.c.) with Ovcar4 cells in the right flank. When tumors reached a volume of 100 $mm^3$ mice were randomized into treatment groups. Established tumors were injected with once weekly with of $2.5\times10^7$ pfu rNDV, R116i-318 with mGM-CSF or hGM-CSF. Tumour growth curves (FIG. 15D) and histological analyses of tumors (FIG. 15E and FIG. 15F) are shown.

FIG. 16 is a table summarizing characteristics of NDV constructs. Plaque formation in Vero cells without trypsin in the overlay after 36 hrs incubation and visualized under ×10 magnification. Cytotoxicity effect of the viruses on human fibrosarcoma HT1080 cells after infection at multiplicities of infection (MOI) of 0.01 at 72 hours postinfection. The relative percentage of surviving cells is determined by comparing each sample with untreated cells that were considered 100% viable. Data presented in the table are relative percentage of dead cells. Pathogenicity of NDV in 1-day-old pathogen-free chicks by the intracerebral pathogenicity index (ICPI). The ICPI assay was performed at National Veterinary Service Laboratories (NVSL) (Ames, Iowa). FIG. 16 discloses SEQ ID NOs: 50-54, 53, and 53, respectively, in order of appearance).

FIG. 17 is a graph showing that NDV produced from eggs and human cell lines exhibited different sensitivity to complement mediated inactivation. Human serum with confirmed complement (C') activity (Sigma, St. Louis, Mo.) was serially diluted with PBS and incubated with 100 pfu of NDV for 1 hour at 37° C. prior to infecting Vero cells for plaque assay. Following incubation at 37° C. for 6 days, the plaques were visualized by crystal violet staining and scored. The virus grown in embryonated chicken eggs was mostly inactivated by serum diluted at 1:10 to 1:40. The 293-grown virus was more resistant to C' than egg-grown virus, approximately 40% infectivity was retained at serum concentration of 1:40. However, the Hela-grown virus was most resistant to C' mediated viral inactivation. Approximately 90% live virus was infectious at serum concentration of 1:40.

FIGS. 18A and 18B are Western blots showing comparisons of RCA protein levels in 293 and Hela cells and in viruses produced from these two cell lines. For FIG. 18A equal amount of 293 and Hela S3 cells were loaded onto the SDS-PAGE for Western blot. Hela cells contained higher levels of hCD46, hCD55 and hCD59 proteins than 293 cells. FIG. 18B shows a Western blot that was performed to examine protein amounts in virus from infected 293 or Hela cells. Uninfected cells (mock) were served as controls. The three CD molecules were detected in viruses from the infected Hela cells at levels higher than those from 293 cells.

FIG. 19 shows evaluation of membrane bound C' regulators (RCA) proteins in C' mediated viral inactivation. The cDNA encoding hCD55, hCD59 and hCD46 was synthesized by Origene (Rockville, Md.) or Genscript (Piscataway, N.J.). Each gene cassette was inserted into the P-N intergenic region of NDV antigenomic cDNA and recombinant viruses were generated by reverse genetics. The recombinant viruses were amplified in eggs and purified by 15-60% sucrose gradient and viral band was pelleted by ultracentrifugation. Expression of each RCA protein by recombinant NDV was confirmed by Western blotting.

FIG. 20 is a graph showing that CD55 is a major RCA protein for preventing C' inactivation of NDV. NDV with hCD46, hCD55 or hCD59 were amplified in eggs, purified by sucrose gradient, incubated with human plasma diluted from 1:10 to 1:40 for 1 hour and viral infectivity was examined by plaque assay in Vero cells. NDV with hCD55 produced in eggs had similar resistance to C' compared to NDV produced in Hela cells, approximately 65% viable viruses at plasma concentration of 1:20 and ~80% viable virus at plasma concentration of 1:40. hCD46 appeared to slightly or marginally improve viral resistance to C' mediated inactivation, approximately 20% more viable virus when incubating with 1:40 diluted human plasma compared to NDV control. No difference was detected at lower plasma dilution.

DETAILED DESCRIPTION OF THE INVENTION

The invention features compositions comprising an attenuated Newcastle disease virus and methods of using that virus for the treatment of neoplasia.

The invention is based, at least in part, on the discovery of an oncolytic NDV with reduced chicken virulence. As reported in more detail below, the NDV 73T strain was derived from NDV MK-107, which is a commercial poultry vaccine (mesogenic) first marketed in 1948. The NDV MK-107 strain was maintained through 73 passages in Ehrlich ascites tumor cells (Cassel et al., Cancer. 1965 July; 18:863-8). NDV MK-107 was used in a series of Ph I and Ph II clinical studies in the 1970's. NDV MK-107 was also used in the 1980's as an immunotherapeutic to treat late stage melanoma patients (Cassel et al., Cancer. 1983 1; 52:856-860; Murray et al., Cancer. 1977. 40:680-686).

In order to generate an oncolytic NDV with reduced chicken virulence, the recombinant NDV 73T strain includes certain genetic modifications. In particular, the F protein cleavage sequence was altered and the length of the HN-L intergenic sequence was increased. Advantageously, the modified virus can be used to express a transgene(s) of interest. In one embodiment, the NDV 73T strain includes a transgene encoding a polypeptide that enhances the oncolytic properties of recombinant NDV. In another embodiment, the NDV 73T strain includes a transgene encoding a biomarker that provides a read-out useful to monitor virus replication. If desired, NDV 73T strain can be modified to incorporate additional genetic information that disrupts the normal transcriptional polarity of the standard genome and is expected to further reduce viral virulence in chickens. Accordingly, the invention provides a recombinant Newcastle Disease Virus (NDV) generated using reverse genetics to reduce its pathogenesis in chickens while maintaining its selective cancer cell killing ability, and methods of producing such a virus. The invention also provides for the construction and use of NDV as a viral vector to deliver and express heterologous gene products for enhanced cancer treatment. The transgenes encoding exemplary therapeutic agents that can be delivered by NDV are described herein below. In working examples described herein below, novel NDV viral constructs expressing granulocyte macrophage-colony stimulating factor (GM-CSF) selectively killed cancer cells, but did not kill normal cells. This selective cancer cell killing effect was observed in a number of cancer cell lines, as well as in vivo when tested in the xerograft HT1080 tumor model. The efficacy and selectivity of the recombinant attenuated Newcastle Disease Virus (NDV) was also demonstrated in a melenoma model where tumor regression was observed. In sum, the invention provides for the insertion of specific transgene(s) into a recombinant attenuated NDV vector and the efficient expression of the encoded protein in a tumor environment.

Newcastle Disease Virus

The Newcastle disease virus (NDV) is an enveloped virus containing a linear, single-strand, nonsegmented, negative sense RNA genome. The negative-sense, single-stranded genome of NDV encodes a RNA-directed RNA polymerase, a fusion (F) protein, a hemagglutinin-neuraminidase (HN) protein, a matrix protein, a phosphoprotein and a nucleoprotein. The genomic RNA contains genes in the following order: 3'-NP-P-M-F-HN-L. The organization of the NDV RNA genome is described in greater detail herein below. The genomic RNA also contains a leader sequence at the 3' end.

The structural elements of the virion include the virus envelope which is a lipid bilayer derived from the cell plasma membrane. The glycoprotein, hemagglutinin-neuraminidase (HN), protrudes from the envelope allowing the virus to contain both hemagglutinin and neuraminidase activities. The fusion glycoprotein (F), which is an integral membrane protein, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome, is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the genomic RNA alone cannot synthesize the required RNA-dependent RNA polymerase. The L, P and NP proteins must enter the cell along with the genome upon infection.

Without being bound to theory, it is hypothesized that most or all of the viral proteins that transcribe NDV mRNA also carry out replication. The mechanism that regulates the alternative uses (i.e., transcription or replication) of the same complement of proteins has not been clearly identified. Directly following penetration of the virus, transcription is initiated by the L protein using the negative-sense RNA in the nucleocapsid as a template. Viral RNA synthesis is regulated such that it produces monocistronic mRNAs during transcription. Following transcription, virus genome replication is the second event that occurs upon infection of a cell by negative-strand RNA viruses. As with other negative-strand RNA viruses, viral genome replication of Newcastle disease virus (NDV) is mediated by virus-specified proteins. The first products of replicative RNA synthesis are complementary copies (i.e., plus-polarity) of NDV genome RNA (cRNA). These plus-stranded copies (antigenomes) differ from the plus-strand mRNA transcripts in the structure of their termini. Unlike mRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of NDV negative-strand viral genomes (vRNAs).

Both the NDV negative strand genomes (vRNAs) and antigenomes (cRNAs) are encapsidated by nucleocapsid proteins; the only unencapsidated RNA species are virus mRNAs. For NDV, the cytoplasm is the site of virus RNA replication, just as it is the site for transcription. Assembly of the viral components likely takes place at the host cell plasma membrane. Mature virus is then released from the cell by budding.

Oncolytic Viruses

Viruses are known to exert oncolytic effects on tumor cells and the use of oncolytic viruses as therapeutic agents has been reported. Some effort has been done to use non-human viruses exhibiting medium to high pathogenicity for their natural hosts in the treatment of cancer patients. The present invention discloses methods for inducing regression of tumors in human subjects, the methods utilize a modified mesogenic strain of Newcastle disease virus (NDV) with modified F protein cleavage site, which is non-pathogenic to poultry (lentogenic), but exhibits oncolytic properties. The disclosed methods provide safe, effective and reliable means to induce regression of a tumor in an individual in need thereof. These methods overcome the drawbacks of using pathogenic strains of viruses for human therapy.

Accordingly in one aspect, the present invention provides a method for inducing regression of a tumor in a subject, the method comprises the step of administering to the subject a pharmaceutical composition comprising a therapeutically effective amount of a lentogenic oncolytic strain of NDV. According to one embodiment, the lentogenic oncolytic strain of NDV is NDV r73T-R116.

Oncolytic viruses are capable of exerting a cytotoxic or killing effect in vitro and in vivo to tumor cells with little or no effect on normal cells. The term “oncolytic activity” refers to the cytotoxic or killing activity of a virus that targets tumor cells. Without wishing to be bound to any mechanism of action, the oncolytic activity exerted by a lentogenic strain of NDV (e.g., r73T-R116), is probably primarily due to cell apoptosis and to a lesser extent to plasma membrane lysis, the latter is accompanied by release of viable progeny into the cell’s milieu that subsequently infect adjacent cells. Without wishing to be bound to a particular theory, it is believed that NDV has direct cytolytic activity on the cancer cells. It is also believed that NDV is capable of specifically differentiating cancer cells from normal, healthy cells. Results have indicated that several oncogenes (H-ras, N-ras, and N-myc) which are known to confer malignant behavior to cancer cells, enhance the susceptibility of cells to killing by NDV. See, Lorence, R. M., Reichard, K. W., Cascino, C. J. et al. (1992) Proc. Am. Assoc. Cancer Res., 33, 398; Reichard, K. W., Lorence, R. M., Cascino, C. J., et al. (1992) Surg. Forum, 43, 603-606. In addition, it has been observed that treatment of cells with retinoic acid (vitamin A) also enhances lysis of cancer cells by NDV. Reichard, K. W., Lorence, R. M., Katubig, B. B., et al. (1993) J. Pediatr. Surg., 28, 1221.

The cytotoxic effects under in vitro or in vivo conditions can be detected by various means as known in the art, for example, by inhibiting cell proliferation, by detecting tumor size using gadolinium enhanced MRI scanning, by radiolabeling of a tumor, and the like.

For clinical studies, it is desirable to obtain a clonal virus so as to ensure virus homogeneity. Clonal virus can be produced according to any method available to the skilled artisan. For example, clonal virus can be produced by limiting dilution or by plaque purification.

NDV Culture

The virus employed in the invention may be prepared by a variety of methods. For example, NDV may be prepared in 8 to 10 day old fertilized chicken eggs (obtained from SPAFAS, Inc., Roanoke, Ill.). Methods of isolating the virus are known in the art and are described, for example, by Weiss, S. R. & Bratt, M. A. (1974) J. Virol, 13, 1220-1230.

This method is further described in Example #1 below. Using this isolation method, NDV may be obtained which is about 90-95% pure.

Alternatively, the virus may be prepared in an in vitro cell culture. Preferably, the cell culture comprises mammalian cells, and more preferably, cells can be used for virus manufacture such as Vero cells. The viruses will be purified by chromatograph or other appropriate methods. The cells may be anchorage-dependent or anchorage-independent.

Cell culture techniques that may be employed in the virus preparation are known in the art and may include use of stationary culture flasks with large surface areas or roller-type flasks. Preferably, the type of culture system selected can support relatively large numbers of cells. To produce large quantity of viruses, a bioreactor process will be deployed whereas the cells are grown in microcarrier beads for virus infection and production.

Cell culture mediums that can be employed in the virus production are known to those skilled in the art. The medium typically includes a nutrient source, antibiotic(s) and albumin or a serum source that contains growth factor(s). It is within the skill in the art to select particular mediums and medium constituents suitable for the cells employed in the culture. In certain embodiments trypsin is included in the growth media. In other embodiments, trypsin is not included.

Culture conditions typically include incubation at a desired temperature (such as 37° C.), as well as selected concentrations of oxygen and carbon dioxide. The particular culture conditions selected can be determined in accordance with the cells employed in the culture, and determination of such conditions is within the skill in the art.

The cells are placed in the culture vessel and allowed to incubate and grow under the selected culture conditions. Preferably, anchorage-dependent cells are allowed to grow to confluence or peak growth. The time required for growth will vary depending upon the size of the initial cell inoculum added to the culture vessel and doubling time of the cell line being employed. Preferably, about $3\times10^3$ to about $3\times10^5$ cells are plated per $cm^2$ and grown for one to five days. For virus inoculation of the cell culture, the medium is removed from the cells (for adherent cells, by aspiration of the culture medium; for cells grown in suspension, by centrifugation of the cell suspension and aspiration of the cell supernatant) and the virus (after reconstitution) is added to the cells in a minimal volume of medium or saline solution (such as Hank's Balanced Salt Solution, Gibco) to prevent dehydration. Preferably, this volume ranges from about 10 to about 2500 microliter per $cm^2$ culture vessel surface area or $10^5$ cells. The preferred dilution of virus inoculum ranges from about 0.001 to about 10 infectious units per cell, the optimal ratio depending on the particular virus and cell line. The virus is then grown from about 1 to 7 days, the length of time being primarily determined by the residual survival of the cell line. For NDV, the optimal time of harvest is 1 to 5 days after virus inoculation.

The virus can then be harvested by either removing the supernatant and replacing it with fresh medium or fresh medium with fresh cells at 12 to 48 hour intervals or freeze-thawing the cells to release virus in the supernatant. The supernatant can then be centrifuged and ultracentrifuged to recover the virus in relatively pure form or by chromatography methods. The purity of the viral preparation may be tested by protein determination and/or by electrophoresis. The virus can then be added to a pharmaceutically-acceptable carrier, described further below.

Therapy

Therapy may be provided wherever cancer therapy is performed: at home, the doctor's office, a clinic, a hospital's outpatient department, or a hospital. In one embodiment, the invention provides for the use of an Newcastle disease virus (NDV) (e.g., r73T-R116).

Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. Cancer growth is uncontrolled and progressive, and occurs under conditions that would not elicit, or would cause cessation of, multiplication of normal cells.

As described above, if desired, treatment with a composition of the invention may be combined with therapies for the treatment of proliferative disease (e.g., radiotherapy, surgery, or chemotherapy).

Formulation of Pharmaceutical Compositions

The administration of a virus of the invention (e.g., NDV r73T-R116) for the treatment of tumors may be by any suitable means that results in a concentration of the therapeutic that, combined with other components, is effective in preventing, ameliorating, or reducing tumors. The agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in a sarcoma (v) formulations that allow for convenient dosing, such that doses are administered, for example, once every one or two weeks; and (vi) formulations that target proliferating neoplastic cells by using carriers or chemical derivatives to deliver the therapeutic agent to a sarcoma cell. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

A composition of the invention, may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic.

Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols. For any of the methods of application described above, a composition of the invention is desirably administered intravenously or is applied to the site of the needed apoptosis event (e.g., by injection).

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for delivering agents include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a composition of the invention is likely to depend on such variables as the type and extent of the disorder, the overall health status of the particular patient, the formulation of the compound excipients, and its route of administration.

Human dosage amounts for any therapy described herein can initially be determined by extrapolating from the amount of compound used in mice, as a skilled artisan recognizes it is routine in the art to modify the dosage for humans compared to animal models. In certain embodiments it is envisioned that the dosage may vary from between about $10^7$ pfu to about $10^{11}$ pfu; or from about $10^8$ pfu to about $10^{10}$ pfu or from about $10^9$ pfu to about $10^{11}$ pfu In other embodiments this dose may be about $10^7$ pfu, $10^8$ pfu, $10^9$ pfu, $10^{10}$ pfu, $10^{11}$ pfu. Of course, a dosage amount may be adjusted upward or downward, as is routinely done in such treatment protocols, depending on the results of the initial clinical trials and the needs of a particular patient.

Selection of a Treatment Method

After a subject is diagnosed as having neoplasia a method of treatment is selected. In neoplasia, for example, a number of standard treatment regimens are available. The marker profile of the neoplasia is used in selecting a treatment method. In one embodiment, neoplasia cells that are responsive to cell killing by NDV (e.g., r73T-R116).

Less aggressive neoplasia are likely to be susceptible to conservative treatment methods. More aggressive neoplasia (e.g., metastatic neoplasia) are less susceptible to conservative treatment methods and are likely to recur. When methods of the invention indicate that a neoplasia is very aggressive, an aggressive method of treatment should be selected. Aggressive therapeutic regimens typically include one or more of the following therapies: surgical resection, radiation therapy, or chemotherapy.

Assays for Measuring Cell Viability

Agents (e.g., NDV) useful in the methods of the invention include those that induce neoplastic cell death and/or reduce neoplastic cell survival, i.e., viability.

Assays for measuring cell viability are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 0.1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Candidate compounds that induce or increase neoplastic cell death (e.g., increase apoptosis, reduce cell survival) are also useful as anti-neoplasm therapeutics. Assays for measuring cell apoptosis are known to the skilled artisan. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Neoplastic cells have a propensity to metastasize, or spread, from their locus of origination to distant points throughout the body. Assays for metastatic potential or invasiveness are known to the skilled artisan. Such assays include in vitro assays for loss of contact inhibition (Kim et al., Proc Natl Acad Sci USA. 101:16251-6, 2004), increased soft agar colony formation in vitro (Zhong et al., Int J Oncol. 24(6):1573-9, 2004), pulmonary metastasis models (Datta et al., In vivo, 16:451-7, 2002) and Matrigel-based cell invasion assays (Hagemann et al. *Carcinogenesis*. 25: 1543-1549, 2004). In vivo screening methods for cell invasiveness are also known in the art, and include, for example, tumorigenicity screening in athymic nude mice. A commonly used in vitro assay to evaluate metastasis is the Matrigel-Based Cell Invasion Assay (BD Bioscience, Franklin Lakes, N.J.).

If desired, candidate compounds selected using any of the screening methods described herein are tested for their efficacy using animal models of neoplasia. In one embodiment, mice are injected with neoplastic human cells. The mice containing the neoplastic cells are then injected (e.g., intraperitoneally) with vehicle (PBS) or candidate compound daily for a period of time to be empirically determined. Mice are then euthanized and the neoplastic tissues are collected and analyzed for levels of NDV, NDV polypeptides, and/or NDV markers (e.g., a transgene encoding a detectable moiety) using methods described herein. Compounds that decrease NDV, NDV polypeptides, or NDV marker levels mRNA or protein expression relative to control levels are expected to be efficacious for the treatment of a neoplasm in a subject (e.g., a human patient). In another embodiment, the effect of a candidate compound on tumor load is analyzed in mice injected with a human neoplastic cell. The neoplastic cell is allowed to grow to form a mass. The mice are then treated with a candidate compound or vehicle (PBS) daily for a period of time to be empirically determined. Mice are euthanized and the neoplastic tissue is collected. The mass of the neoplastic tissue in mice treated with the selected candidate compounds is compared to the mass of neoplastic tissue present in corresponding control mice.

Kits

The invention provides kits for the treatment or prevention of sarcoma. In one embodiment, the kit includes a therapeutic or prophylactic composition containing an effective amount of an NDV (e.g., r73T-R116) in unit dosage form. In a further embodiment, the kit includes a therapeutic or prophylactic composition containing an effective amount of NDV (e.g., r73T-R116) in unit dosage form.

In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an antibody of the invention is provided together with instructions for administering an NDV (e.g., r73T-R116) to a subject having or at risk of developing neoplasia. The instructions will generally include information about the use of the composition for the treatment or prevention of neoplasia. In other embodiments, the instructions include at least one of the following: description of the therapeutic agent; dosage schedule and administration for treatment or prevention of neoplasia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Assembly of Antigenome cDNA of NDV Strain 73T

Six subgenomic cDNA fragments generated by high-fidelity RT-PCR were assembled in the pUC19 vector. The full length cDNA of NDV 73T was designated as p73T. The nucleotide and deduced amino acid sequences of the F protein cleavage site (FPCS) in 73T were modified to that of the NDV LaSota strain (lentogenic, lento) or glycoprotein B (gB) of cytomegalovirus (CMV) (S116) (FIG. 1; double slash indicates the site of cleavage of the F protein). The cDNA was completely sequenced to confirm the viral sequence. F protein cleavage site: Wt: ggg agg aga cag aaa cgc ttt (SEQ ID NO: 16); Lento: ggg ggg aga cag gaa cgc ctt (SEQ ID NO: 17); S116: cat aat aga acg aaa tcc ttt (SEQ ID NO: 18); S116KM: cat aat aaa atg aaa tcc ttt (SEQ ID NO: 19); R116: cat aat aga acg aaa cgc ttt (SEQ ID NO: 20).

Example 2. Transgene Insertion into NDV 73T Genome

Transgenes were inserted into p73T at two locations: at the intergenic sequences between P and M or at the intergenic sequences between the HN and L junctions (FIG. 2A). To insert a single transgene cassette at P-M or HN-L junctions, construction of p73T cDNA containing a transgene at the P-M or HN-L junctions was performed by inserting the transgene cassette into AfeI sites created between the P and M genes (nt 3148) or between the HN and L genes (nt 8231). The inserted gene cassette contains the gene end (GE; 5'-TTAAGAAAAAA-3') (SEQ ID NO: 13), intergenic nucleotide (T), gene start sequence (GS; 5'-ACGGGTAGA-3') (SEQ ID NO: 14), and open reading frame (ORF) of the transgene. In addition, ten nucleotides (5'-cgccgccacc-3') (SEQ ID NO: 15) were inserted upstream of the initiation site to introduce a Kozak sequence. The full length (FL) 73T cDNA containing the transgene at P-M or HN-L junction was designated as p73T-P1 or p73T-HN1, respectively. Full-length cDNA containing two separate transgenes at P-M and HN-L junctions in a single genome were constructed and designated as p73T-P1-HN1 (FIG. 2B). To insert two transgene cassettes at the same junction (e.g., P-M), an AfeI site was introduced at the end of ORF the first transgene (#1) (nt 3169). The 2nd transgene ORF was PCR amplified with primers containing GE and GS sequences and inserted at the AfeI site. The antigenomic cDNA containing two transgene cassettes the P-M junction was designated as p73T-P2.

Example 3. Recovery of Infectious Recombinant NDV Strain 73T (r73T) with Modified FPCS The NDV 73T NP, P, L proteins and antigenic cDNA (p73T-lento or p73T-S116) were cloned under the control of the T7 RNA polymerase promoter and terminator. The four plasmids were co-transfected into an RNA polymerase expressing cell line (FIG. 3A). The recovered viruses were designated as r73T-lento or r73T-S116. The r73T-lento and r73T-S116 were passaged in Vero cells with media with and without trypsin supplement. The growth of r73T-lento is trypsin dependent whereas r73T-S116 can grow in medium without trypsin supplement. F protein cleavage sequences (FPCS) in r73T-S116, with and without hGM-CSF at the P-M junction, were assessed. The 73T-S116 strains were further passaged for 10 passages in Vero and human fibrosarcoma HT1080 cells at MOI 0.01 in media without supplement of trypsin. Mutations in the FPCS (R113K and/or Q114M) appeared at passage 7. The S116R mutation was detected at passage 9. At passage 10, the F, HN and transgene were sequenced and no additional mutations were found.

Example 4. Characterization of the Recombinant 73T Strain with Different F Protein Cleavage Sequences Recombinant 73T strain with novel modified F protein cleavage sequences (FPCS) included the following sequences:

```
Lento:   $^{111}$G-G-R-Q-E-R/L-I$^{118}$    (SEQ ID NO: 21)

S116:    $^{111}$H-N-R-T-K-S/F$^{117}$     (SEQ ID NO: 1)

S116K:   $^{111}$H-N-K-T-K-S/F$^{117}$     (SEQ ID NO: 2)

S116M:   $^{111}$H-N-R-M-K-S/F$^{117}$     (SEQ ID NO: 3)

S116KM:  $^{111}$H-N-K-M-K-S/F$^{118}$     (SEQ ID NO: 4)

R116:    $^{111}$H-N-R-T-K-R/F-I$^{118}$   (SEQ ID NO: 5)
```

The recombinant 73T strains with different FPCS were characterized with regard to MDT, ICPI, relative HT1080 cell killing, replication in Vero cells, and replication in eggs (FIG. 4).

Avian virulence of NDV is mainly determined by the F protein cleavage sequences (FPCS). r73T-lento was engineered to contain the FPCS of the non-virulent strain LaSota. Replication of LaSota virus in the tissue cultures is trypsin dependent, as F protein cannot be cleaved. r73T-lento forms tiny plaques in Vero cells without trypsin supplement, indicating that the F protein is not cleaved and virus cannot spread efficiently from cell-to-cell. r73-lento replicated at a low level in Vero cells ($7.5 \times 10^3$ pfu/ml), but efficiently in eggs with endogenous trypsin-like enzyme ($5.7 \times 10^8$ pfu/ml). r73-lento is not virulent in chickens as demonstrated by the mean death time (MDT) of embryos inoculated with the virus (MDT >156 hr) and by an intracerebral pathogenicity index (ICPI; ICPI=0.00), and has low cytotoxicity in HT1080 cells (13% cell killing).

r73T-S116 can form relatively large plaques, and reaches a titer of $4.4 \times 10^6$ pfu/ml in Vero cells. This was comparable to the titers obtained when r73T-S116 was grown in Vero cells supplemented with trypsin. This data indicated that the fusion protein cleavage site (FPCS) of r73T-S116 can be cleaved without exogenous trypsin in tissue cultures. It was not virulent in chickens and showed 31% cell killing in HT1080 cells. r73T-S116 was examined for its genetic stability by in vitro cell passage.

After 10 passages in Vero or HT1080 cells, amino acid substitutions were found in the FPCS: R113K, Q114M, and/or S116R. To eliminate the possibility that additional sequence change had occurred in the viral genome, recombinant r73T-S116 mutant viruses were constructed by reverse genetics and evaluated. Except for r73T-R116, r73T-S116 and its derivatives were similar to the parental S116 in that these mutant viruses were not virulent in chickens and were capable of similar levels of HT1080 cell killing. HT1080 cell killing was between 29%-31% for the single mutation and 48% for the double mutations.

The plaque size of M114 and K113M114 were significantly larger than S116. The r73T-R116 mutant acquired one amino acid change at residue 116 (S116R) in the FPCS. The R116 next to the cleavage site is known to be important for efficient cleavage of the F protein. r73T-R116 formed large plaques in Vero cells, grew to similar titers with and without trypsin supplement, and efficiently killed HT1080 cells (80%). R116 increased chicken virulence as shown by the MDT assay (72, 80 hrs). Although the ICPI value (0.65) was <0.7 in one test, it is preferable to further reduce its chicken virulence.

Example 5. r73T-R116 Derivatives have Reduced Chicken Virulence

Virus can be engineered to express a transgene at the P-M junction (1) a 2nd transgene at the HN-L junction (2) and an increased HN-L intergenic region that is extended by insertion of non-coding sequence (3) (FIG. 5A). The same design for insertion of a transgene cassette at P-M junction as in FIG. 2A is used here. The 2nd transgene cassette contains the L gene start sequence (GS; 5'-ACGGGTAGA-3') (SEQ ID NO: 14), open reading frame (ORF) of the transgene, sequences from 3' untranslated region of the L gene (highlighted in italics) and the L gene end sequence (GE;

5'-TTAAGAAAAAA-3') (SEQ ID NO: 13). The non-coding sequence used to increase the HN-L junction were taken from paramyxoviruses type-1 (APMV-1), respiratory syncytial virus (RSV) or random sequence which does not have homology with any known sequence. The insertion can be in the range of 60-318 nt. Insertion of a 2nd transgene at HN-L allowed the virus to express two transgenes, such as hGM-CSF and GFP. Inserted sequences at the HN-L junction are listed (FIG. 5B).

Example 6. Modification of r73T-R116 and Characterization of r73T-R116 Derivatives To reduce r73T-R116 virulence in chickens, r73T-R116 virus was modified to increase the HN and L intergenic sequence by insertion of sequences of various lengths. r73T-R116 derivatives were evaluated for infectivity by examining plaque formation and replication in cells and eggs; for avian pathogenicity by examining MDT and ICPI, and for tumor cell killing (FIG. 6A).

Intergenic insertions of 318 nt from APMV, 198 nt from RSV and 198 random sequences indeed reduced virulence in chickens, with MDT >156 hr and ICPI of 0.27, 0.0375 and 0, respectively. A long insertion (random 198 nt) had an increased effect on reducing virulence than a short insertion (random 60 nt). The insertion of 144, 102 and 60 nt had some virulence in chickens, but MDT times were shorter. ICPI values for the insertion of 144, 102 and 60 nt were 0.74, 0.51 and 0.78, respectively. The insertion of non-viral sequence (random 198 nt) more effectively reduced virulence than insertion of viral sequence (RSV-198 nt). The insertion of the $2^{nd}$ transgene cassette (EGFP) at the HN-L junction did not reduce chicken virulence (MDT 86 hr and ICPI of 0.82). All insertions slightly reduced viral replication in eggs by up to 4-fold, but did not effect viral replication in Vero cells (~$10^6$ pfu/ml). Although mutant viruses were more attenuated in chicken, tumor cell killing function was not affected. All r73T-R116 derivatives had tumor cell killing efficiency in the range of 75%-86% on day 3 of infection.

Example 7. Growth Kinetics of r73T Viruses in Eggs and Vero Cells

To determine growth conditions for the r73T viruses, growth kinetic studies were performed in eggs (FIG. 7) and Vero cells (FIG. 8). Chicken embryonated eggs were infected with 100, 1000, 10,000 or 100,000 FFU/egg of indicated viruses and incubated for 2, 3 or 4 days. The allantoic fluid was harvested and viral titers were determined by FFA. As shown in FIG. 7, 100 FFU/egg had low titer on day 1, but reached peak titer on day 2. Overall, most viruses reached peak titers of ~8 logs/mL on Day 2 regardless of the inoculate dose used. R116i-198 had the lowest titer, low inoculum dose generated the highest yield on day 2, indicating that there might be accumulation of defective particles. R116i-318-APMV insertion also had a lower peak titer of ~7 logs. R116i-198-RSV reached a peak titer of 7.5 logs. S116 constructed by reverse genetics had no reduction in virus production in eggs. Therefore, among the R116 derivatives, the virus with RSV-198 nt insertion was a top candidate of oncolytic virus in terms of growth properties in eggs.

The viruses were also evaluated in sero-free Vero cell clone 51D11, a proprietary cell line generated by MedImmune. All the viruses replicated well under both MOI conditions (0.001 and 0.0001) (FIG. 8). The modification of 73T FPCS and intergenic insertion in the HN-L junction of R116 did not affect virus growth in Vero cells.

Example 8. Selective Cell Killing of r73T and Derivatives in Cancer Cells Compared to the Normal Cells rT3T and its derivatives were evaluated for their cell killing in human fibrosarcoma HT1080 compared to normal human skin fibroblast CCD1122Sk cells, relative to untreated control cells (FIGS. 9A and 9B). Data were obtained after infection with r73T derivatives at different doses ranging from 1 to 100,000 PFU for 72 hr. In HT1080 cancer cells, the virus with lentogenic FPCS had the least killing, S116 at the FPCS was intermediate, and virus with R116 at FPCS had cell killing as efficient as r73T wt virus. In normal CCD1122SK cells, cell killing of all viruses was not as efficient as that for cancer cells. The reduction in killing efficiency was ~100-fold. Regardless of the FPCS sequences, all viruses had similar killing efficiency in the normal cells. The cell killing efficiency in cancer and normal cells was expressed as 50% effective concentration ($EC_{50}$) interpolated from the dose response curve using Prism 6.0 (FIG. 9C). R116 derivative had a similar $EC_{50}$ value as r73T wt with $EC_{50}$ of 10 PFU, indicating that the modification of FPCS did not affect virus replication and cell killing efficiency in cancer cells. Replication of these viruses in the HT1080 and CCD1122SK cells at MOI 0.01 was determined on day 3 post infection (FIG. 9D). All viruses preferentially replicated in the cancer cells over normal cells, with a difference of about 1.5-2.0 logs.

Example 9. r73T Derivatives Had Anti-Tumor Activity In Vivo when Delivered Either Systemically or Intratumorally to Immunodeficient Mice Carrying Human Tumor Xenografts To evaluate oncolytic activity in vivo, HT1080 xenograft model was established by injecting the HT1080 cells at a concentration of $5\times10^6$ cells/0.1 ml subcutaneously into Balb/C athymic nude mice at age of 5-6 week old. As hGM-CSF has no cross reactivity in mouse, this study was not geared to assess the transgene effect, but the oncolytic capability of various r73T constructs. R116-318i-hGM-CSF was given intratumorally (it) or intravenously (iv) and tumor growth rate was compared between the treatment and the control groups (FIG. 10A).

Mice were randomized into groups (N=10) as indicated when tumor volume reached approximately 65 $mm^3$. Mice received a single dose of either PBS or $2\times10^7$ Pfu of r73T-hGM-CSF-R116i-198 administered intratumorally (IT) or $1\times10^8$ PFU administered intravenously (IV) via tail vein injection. Tumor size was measured every 3-4 days. As presented in FIG. 10A, r73T-R116i could induce significant tumor regression when it was either administrated by IV or IT. The amount of tumor regression induced by the two routes was comparable, and was significantly different from the control group.

The oncolytic activities of r73T derivatives were compared in the HT1080 xenografts by IT injection of $1\times10^8$ PFU (FIG. 10B). Mice were randomized into groups (n=7) when tumor volume reached approximately 180 $mm^3$. Mice received either PBS or $1\times10^8$ PFU of r73T-hGM-CSF-lento (lento) or r73T-hGM-CSF-S116K113M114 (S116 KM) or r73T-hGM-CSF-R116i-318 nt APMV-N(R116i) or r73T-hGM-CSF (r73T wt). Tumor size was measured every 3-4 days (*$P<0.05$, un-paired student T test). Two doses of r73T derivatives were capable of inducing significant tumor regression albeit differences in effectiveness. r73T-lento was the least effective whereas r73T wt was the most effective in tumor regression. r73T-lento had similar effect as the S116 virus although S116 virus had 10-fold lower $EC_{50}$ for in vitro cell killing (FIG. 9A). r73T-R116i-318 was as potent as 73T wt in inhibition of tumor growth until 9 days post the $2^{nd}$ dose (day 19 post tumor implantation), the tumor grew back in R116i treated mice, but not in the 73T wt treated group. These data showed that r73T derivatives had anti-tumor activity in vivo when delivered either systemically or intratumorally to immunodeficient mice carrying human tumor xenografts. The efficient cleavage of the F protein is important for virus replication in vitro and in vivo. The viruses with the R116 at the FPCS were more potent in cell killing in vitro and in vivo.

Example 10. Tissue Biodistribution of r73T Derivative Following Intravenous Delivery To determine if the oncolytic NDV virus selectively replicates in tumor tissues and viral clearance, virus distribution in different organs was determined. Athymic nude mice bearing subcutaneous HT1080 tumors with size of ~250 $mm^3$ were treated with R116i (r73T-hGM-CSF-R116i-318 nt APMV-N) at a dose of $1\times10^8$ PFU intravenously and sacrificed on day 1, 4, or 8 (n=3 per time point). Serum, lungs, spleen, ovaries and tumor were collected.

The presence of virus was quantified by plaque assay in Vero cells, and hGM-CSF transgene expression was measured by ELISA assay. Virus replication in tumor and organs were assessed on day 1, 4 and 8 post infection. Virus was only detected in organs on day 1 (no virus was detected in ovary at all time points) and virus load in tumor tissues was ~100-fold higher than lungs and spleens (FIG. 11A). The presence of virus in tumor persisted for at least 8 days, indicating that the virus selectively replicated in tumor tissues. Consistent with the viral replication data, the level of hGM-CSF was the highest and lasted more than 8 days (FIG. 11B). These data demonstrated that the NDV virus can effectively replicate in tumor tissue and deliver the transgene to the local tumor tissue effectively.

Example 11. Antigenome cDNA of 73T Containing Chimeric F and/or HN Gene

Viral surface glycoproteins are important antigens for immunogenicity and virulence in chickens. Strategies were explored to replace the F and HN genes of NDV by the corresponding extracellular (ecto) domains of other paramyxoviruses which are not virulent in chickens individually or in combination. Parainfluenza virus 5 (PIV 5) is a canine paramyxovirus and does not cause diseases in human. Pigeon paramyxovirus type 1 (PPMV-1) has been shown to be nonvirulent in chickens with an ICPI of 0.025, as previously reported, and is antigenically distinct from NDV (Dortmans et al, *Veterinary Microbiology,* 2010, vo. 143, pages 139-144.) There exist two genetically closely related pigeon paramyxovirus type 1 (PPMV-1) variants with identical velogenic fusion protein cleavage sites, but with strongly contrasting virulence (Veterinary Microbiology, 2010, 143:139-144). Full-length antigenomic cDNAs of NDV 73T in which the F and/or HN glycoprotein ectodomain were swapped with that of PPMV-1 and/or PIV5 were generated (FIG. 12A). NDV, PIV5 and PPMV-1 sequences are indicated with colored boxes as blue, purple or green, respectively).

The amino acid lengths of individual proteins or protein domains are indicated. Plaque formation in Vero, relative HT1080 cell killing and MDT were performed as described previously (FIG. 12B). Chimeric viruses, except for PIV-5 F-HN, were recovered and were capable of growing in the cells in the absence of exogenous trypsin. All three viruses formed good sized plaques, showing efficient cell-to-cell spread. PPMV-1 F-HN or F chimeric viruses had MDT values of 79 and 84 hr, respectively, indicating potential virulence in chickens. Both PPMI-1 chimera killed HT1080 cells efficiently at levels of 71 and 61%. PIV5-F chimera did not grow in eggs and was not virulent in chickens, and killed HT1080 cells at 47%. Serum cross reactivity between the NDV and PPMV-1 or PIV5 chimeras was examined by neutralization assay using the serum collected from mice that received two intravenous doses of $1\times10^8$ PFU of r73T-R116i. The r73T virus was neutralized with the NDV-infected serum (titer 960) whereas the PPMV-1 and PIV5 chimera were not neutralized (titer <4). This result confirmed that there was no cross reactivity between NDV and PPMV-1 or PIV5. Chimeric viruses with distinct antigenicities have the potential to serve as boosting oncolytic viruses for the patients that have developed anti-NDV immune responses during prior NDV treatment.

A comparison of NDV RNA polymerase activity with other paramyxoviruses by mini-genome assay (FIG. 12C). The T7 expressing cells were transfected with the three plasmids expressing the NP, P, L proteins of NDV and the plasmid encoding the NDV anti-minigenomic cDNA encoding the GFP gene using Lipofectamine 2000, or the plasmids encoding N, P, L genes of measles virus (MV) or respiratory syncytial virus (RSV) and respective RSV or MV GFP anti-minigenome cDNA plasmid. Two or three days post transfection, minigenome replication as indicated by the expression of GFP proteins was examined under fluorescent microscope. The NDV had the strongest polymerase activity compared to measles virus and RSV.

Example 12. Cancer Cells Sensitive to NDV were Identified by Cell Panel Screening In order to understand what tumor types may be sensitive to NDV oncolysis, 180 cancer cell lines covering a broad range of tumor types and indications were tested for sensitivity to recombinant NDV and variants thereof. Cell lines were obtained from American Type Tissue Collection (Manassas, Va.) or the European Collection of cell cultures (ECACC) and were cultured in media and under conditions recommended by the supplier. 10,000 cancer cell lines were seeded in 96 well plates and were infected 6 hours later with a virus. Virus concentrations ranged from MOI 10-0.0001 (or 1 to 100,000 pfu per well). Cell viability was determined 48-96 hrs post infection. Sensitivity was determined using a cut off of >30% cell kill at 72 hrs post infection with virus at an MOI of 0.1. FIGS. 13A and 13B provide an overview of the sensitivity by tumor type. Haematological cancer cell lines (leukemia and lymphoma) were relatively insensitive to NDV oncolysis whereas a majority of the melanoma, ovarian and pancreatic cell lines tested were sensitive to NDV. Approximately 58% of all human cancer cell lines tested were sensitive to NDV R116i at FPCS relative to 4% of cell lines tested were sensitive to the S based virus. This was most likely due to the cleavage of the F protein by proteases. The R116i virus is more likely to be cleaved by ubiquitous furin-like proteases whereas the protease that is likely to cleave the S116 F protein is undefined and is probably less ubiquitously expressed. The re-derived S116-

KM variant yielded larger plaque size and enhanced oncolytic potency relative to the original S116 variant. To test this further a smaller panel of 22 cancer cell lines that had been determined to have a range of sensitivity to NDV R116 virus was infected with GFP expressing variants and cell viability was determined at 72 hr post infection. Using the same sensitivity cut off as described above, 41% of cell lines tested were sensitive to R116i, 4% sensitive to S116 and the rederived S-KM is more potent than the S116 NDV with 27% of cell lines tested being sensitive.

TABLE 1

Summary of cancer cell sensitivity to virus killing by R116-hGM-CSF

| Indication | No. cell lines tested | No. cell lines sensitive to S116 | No. cell lines sensitive to R116i |
|---|---|---|---|
| Bladder | 8 | 0 | 6 |
| Bone | 4 | 0 | 4 |
| Brain | 4 | 0 | 4 |
| Breast | 26 | 2 | 14 |
| Colorectal | 14 | 0 | 3 |
| gastric | 4 | 0 | 3 |
| HNSCC | 9 | 0 | 5 |
| Haem | 28 | 0 | 4 |
| Kidney | 4 | 0 | 4 |
| Liver | 9 | 2 | 7 |
| Lung | 28 | 0 | 20 |
| Melanoma | 8 | 0 | 8 |
| Ovarian | 10 | 0 | 8 |
| Pancreatic | 14 | 0 | 11 |
| Prostate | 6 | 2 | 3 |
| Other | 3 | 1 | 1 |

The cells derived from the indicated cancer tissues were examined for cell killing by recombinant NDV 73T with R116 at the FPCS and human GM-CSF. The number of the cells that showed greater than 50% killing by the virus infection at moi of 0.1 and total cell lines screened are indicated.

Example 13. r73T Derivatives Had Tumor Killing and/or Tumor Growth Inhibiting Activity in Syngeneic Melanoma Model Following tumor model refinement, S116-RD NDV encoding human or murine GM-CSF was tested for efficacy in refined B16F10 syngeneic model (FIGS. 15A and 15B). $1 \times 10^8$ pfu was infected intratumorally for 3 doses and there were a minimum of 8 mice per group. Significant tumor growth inhibition is demonstrated with >80% tumor growth inhibition (FIG. 15B). Short term tumor regression was achieved with repeat intratumoral (i.t.) dosing, which also led to a significant increase in survival time 18 days for control relative to 42 days in treated group. Cessation of treatment after 3 doses was followed by tumor re-growth. A single animal with no evidence of residual tumor in S116-mGM-CSF group at 50 days was re-challenged by implantation of B16F10 tumor cells on the alternate flank. Tumor growth was delayed but not inhibited, suggesting in this model that a full immune memory response was not achieved within this single animal.

In order to assess oncolytic and immune effects on tumor growth, NDV variants R116i and S116 encoding hGM-CF or mGM-CSF respectively were tested for efficacy in the mouse syngeneic immune competent CT26 colorectal tumor model. Each virus was dosed with $1 \times 10^8$ PFU of virus intra-tumorally for 4 doses. Tumors were a minimum of 100 mm³ before dosing commenced. As shown in Table 2 below, all animals treated with virus demonstrated potent anti-tumor activity as a monotherapy. With 11/12 animals tumor free following treatment with R116 encoding human GM-CSF which is a 92% complete response rate. The less lytic re-derived S116-KM virus had a reduced tumor growth inhibition achieving 53% TGI and a complete response rate of 36%. However, in the presence of murine GM-CSF which unlike human GM-CSF will be active in the mouse model this response rate was increased to 54% with a tumor growth inhibition of 75%. Thus, it is likely that arming the S116 virus with GM-CSF may enhance anti-tumor activity.

TABLE 2

| Virus | % TGI | % Complete response (CR) |
|---|---|---|
| R116 hGM-CSF | 83 | 92 |
| R116 mGM-CSF | ND | ND |
| S116 hGM-CSF | 53 | 36 |
| S116 mGM-CSF | 75 | 54 |

Tumors that were remaining were taken for histological analysis and stained by Hematoxylin and eosin stain (H and E) and using immunohistochemistry methods for NDV detection (FIG. 15C). There is clear evidence of NDV expression and this appears to be concentrated around the necrotic areas of the tumor, suggesting that NDV is contributing to tumor cell death and necrosis. There is also clear evidence of immune cell infiltration into the tumor and necrotic areas. In areas that have strong staining for NDV multinucleated cell syncytia formation can also be noted. Additionally, there appears to be very minimal remaining viable tumor, indicating the tumor growth inhibition data may underestimate the activity of NDV within this model.

FIG. 15C shows NDV has potent anti-tumor activity in immune-competent mouse CT26 colorectal tumor model. In order to assess oncolytic and immune effects on tumor growth, NDV variants (R116i and S116 encoding hGM-CF or mGM-CSF respectively were tested for efficacy in the mouse syngeneic immune competent CT26 colorectal tumor model. Each virus was dosed with $1 \times 10^8$ PFU of virus intra-tumorally for 4 doses. Tumors were a minimum of 100 mm³ before dosing commenced. All animals treated with virus demonstrated potent anti-tumor activity as a monotherapy. With 11/12 animals tumor free following treatment with R116 encoding human GM-CSF which is a 92% complete response rate. The less lytic re-derived S116-KM virus had a reduced tumor growth inhibition achieving 53% TGI and a complete response rate of 36%. However, in the presence of murine GM-CSF which unlike human GM-CSF will be active in the mouse model this response rate was increased to 54% with a tumor growth inhibition of 75%. Thus, arming the S116 virus with GM-CSF enhances anti-tumor activity.

FIGS. 15D-F show that multiple dosing with rNDV R116i caused tumor growth inhibition and drove immune cell recruitment into ovarian cancer (OVCAR4) xenograft model. To further evaluate rNDV oncolytic activity in vivo a human ovarian cancer xenograft model (OVCAR4) was utilized. This model is slow growing and has gross pathology reminiscent of human ovarian tumors with a poorly differentiated cell morphology and large ascetic like fluid filled areas. Once tumors had reached 100 mm³ mice were randomized to receive 8 doses of R116i NDV encoding either mouse or human GM-CSF or PBS as a control. Only the product from the murine gene sequence would be bioactive in the mouse model. $2.5 \times 10^7$ pfu were injected intra-tumorally in a volume of less than 50 µl once weekly. Tumor growth curves are shown in FIG. 15D. Long term tumor inhibition achieved in tumor-bearing animals treated with either NDV variant. There was also evidence of viral genome using RT-PCR within the tumor at the end of the study (24 hrs post last dose). Following histological analysis there is clear evidence of immune infiltrate as well as other histological changes in residual tumor (FIGS. 15E and F). Treated tumors are far less de-differentiated than control treated animals and appear to have less ascites fluid filled areas. A high level of inflammatory infiltrate found in number of treated tumors adjacent to remaining tumor and immunohistochemistry (IHC) analysis reveals these immune infiltrates are positive for NDV protein. There is a strong degree of innate immune cells recruitment into the tumors in NDV treated groups. These data demonstrate potent antitumor efficacy in a morphologically relevant ovarian cancer model which may be caused via direct oncolysis and innate immune recruitment and activation.

Example 14. NDV Viruses Induced Tumor Regression

73T-R116i-hGM-CSF and 73T-R116i-mGM-CSF were evaluated for oncolytic effect in the B16 melanoma model. The study evaluated virus tolerability in the B16 mouse. Each virus was dosed at $2 \times 10^7$ pfu twice on days 11 and 14 intravenously (i.v) or intraperitoneally (i.p), or once on Day 11 at $1.1 \times 10^7$ pfu intratumorally (i.t). The groups treated with R116-hGM-SCF or mGM-SCF by three different routes of administration had slower rate of tumor growth compared to the untreated group (FIG. 15A). Each group included 3 mice. The tumor inhibition rates were statistically significant from the control group. Thus, r73T derivatives of the invention had advantageously low avian pathogenicity, high oncolytic activity, and replicated to high titers in chicken eggs. Based on these results, viruses of the invention are useful to induce tumor regression and enhance cancer patient treatment outcomes (FIG. 16).

In addition to GM-CSF, a number of transgenes (Table 3) may be inserted into NDV 73T strain to enhance tumor killing. These transgenes include the following:
(1) Cytokines or engineered variants of cytokines, such as GM-CSF, IL-2, IL-21, IL-15, IL-12 and IL-12p70
(2) Cell surface ligands and chemokines, including OX40L, CD40L, ICOSL, Flt3: B.1 (CD80), CD137L, CXCL10 (IP-10), CCL5, CXCL9. (3) Myc inhibitor: Omomyc. (4) Transgenes for in vivo imaging purposes, such as Sodium iodide symporter (NIS)-mediated radiovirotherapy for radiovirotherapy. (5) Additional modulators of tumor cell survival to enhance tumor killing including, but not limiting to, inhibitors of cell cycle progression, inhibition of anti-apoptotic proteins, enhancement of pro-apoptotoic proteins, inhibition of key oncogenic drivers of malignant transformation. These may include transgenic delivery of proteins following selective NDV replication in tumor cells, the production of selective or broad activity siRNA, the delivery of miRNA or the inhibition of selected miRNA (6) Tumor antigens such as E6, E7, cancer testis antigens, oncofetal antigens, artificial or overexpressed proteins as novel tumor antigens either alone or in combination with other transgenes. (7) Antibodies or recombinant fusion proteins that target immunomodulatory proteins to either block negative regulation or provide an agonistic signal to enhance T-cell function. Example of such antibodies may include but are not limited to; PD-L1, CTLA4, CD-137 (4-1 BB), OX40, GITR, TIM-3, CD73, PD-1, HVEM, and LIGHT. (8) Augmentation of recNDV's pharmacodynamic/pharmacokinetic activity by engineering or expressing recNDV in cells that transfer proteins onto recNDV to reduce clearence by complement or to diminish the adaptive immune response to NDV.

TABLE 3

Transgenes for potential insertion into NDV 73T and their biological activities

| Transgene | Gene Size | MOA (functions relating to immunotherapy) |
|---|---|---|
| Cytokines | | |
| GM-CSF | 0.47 kB | Hematopoietic cell growth factor Stimulates stem cells to differentiate to granulocytes and monocytes (and ultimately APCs, |
| IL-2 | 0.48 kB | Stimulates CD8 T, CD4 T, NK, and B-cells Augments cytokine production Induces T-reg expansion |
| IL-21 | 0.6 kB | Stimulates CD8 T-cells, NK, and B cells Does not induce T-reg expansion |
| IL-15 | 0.5 kB | Similar to IL-2 function Supports survival of CD8 CTLs (in contrast to IL-2 which promotes memory CD8 CTLs) |
| IL-12p70 | | Stimulates CD8 T-cell and NK cells |
| IL-12A | 0.76 kB | Drives Th1 CD-4 T-cells differentiation |
| IL-12B | 0.99 kB | Reduces T-regs Re-polarizes M2 macrophages to M1 macrophages |
| Cell Surface Ligands and Chemokines | | |
| OX40L | 0.55 kB | Binds receptor on activated (not naïve) T-cells delivering activation signal Downstream effects of activation on T-cell: Proliferative and anti-apoptotic Induces cytokines, Ag-spec Ab, memory T-cells |
| CD40L or CD40 | 0.79 kB | Binding to receptor on DCs is critical for T-cell priming (MHC-II, CD86, CD80 upreg) Stimulates IL-12, MIP-1a from DCs driving Th1-diff and migration to inflammatory sites Important for CTL (cross-priming) |
| ICOSL | 0.9 kB | ICOS Receptor expressed on naïve T-cells and upreg. after TCR and CD28 stim. Literature shows evidence of both Th1 and Th2 differentiation through ICOS Provides signal for high affinity Ab production |
| Flt3L | 0.7 kB | Key driver of hematopoietic cell (DCs, NK, and B cells) development and differentiation Ubiquitously expressed (receptor limited to immune cells) |
| B7.1 (CD80) | 0.866 kB | Typically up-regulated on maturing DCs Co-stimulatory molecule for CD4-Naïve T-cell differentiation into T-helper subsets (Th1; IL- |
| CD137L | 0.767 kB | Expressed on DCs, NK cells, activated CD8-T cells Triggers T-cell proliferation, IL-2 secretion, and cytolytic abilities |
| CXCL10 (IP-10) | 0.296 kB | ELR-negative molecule with demonstrated anti-tumor activity Chemoattractant for T-cells, NK cells, monocytes, DCs Attenuates angiogenesis |
| CCL5 (RANTES) | 0.275 kB | Chemoattractant for Eosinophils, Basophils, Mast cells, monocytes, CTLs, CD4-T-cells, Anti-tumor functions thought to be the result of immune cell infiltration |
| CXCL9 (MIG) | 0.367 kB | Chemoattractant for Leukocytes IFN-gamma dependent expression; NOT induced by IFN-alpha/beta myc inhibitor |
| Omomyc | 1.3 kB | Demonstrated efficacy in mouse lung cancer model |
| Image | | |
| NIS | 2 kB | human sodium iodide symporter to concentrate 131-I in caner cells for radiovirotherapy |

Example 15. Cancer Therapy Involving Administration of Oncolytic NDV in Combination with Immune Modulatory mAb NDV oncolytic virus can be administered concurrently or sequentially with therapeutic antibodies or agonistic fusion proteins where appropriate (e.g. anti-PD-L1, anti-CTLA4, anti-OX40, anti-GITR, anti-TIM-3, anti-PD-1 and anti-ICOS). Preclinical data are generated that establish the most effective dose and schedule of molecules that enhance the activity of NDV in tumor models in combination with the novel NDV constructs described herein. Transgenes may be inserted into recombinant NDV for expression either singly or in combination to deliver multiple modes of activity, e.g., to enhance the tumor cell death induced by the novel variants of NDV. Increasing the release of tumor cell antigens combined with an immunomodulatory approach has the potential to increase the adaptive immune response to these liberated tumor antigens.

Example 16. F Protein Cleavage Efficiency and Fusion Activity were Reduced in F Protein with R, S or S-KM Mutation at the F Protein Cleavage Site In order to understand whether the difference in the F protein cleavage site affects F protein cleavage in the infected cells and its impact on the fusion activity, the F protein plasmid was transfected into 293 cells to examine F protein cleavage. In addition, the F and HN plasmids were cotransfected to examine fusion activity in the transient assay as both the F and HN proteins are required for fusion formation (FIGS. 3B and 3C). Wt F protein was cleaved by host protease more efficiently than the F protein with R, S or S-KM mutation at the F protein cleavage site, very little F protein cleavage product (F1) was detected in F with the S cleavage site and no cleavage product was detected in lentogenic F plasmid transfected cells. The F protein of R and S construct has an N-linked glycosylation site (NXT) at the cleavage site resulting in the slower migrating mobility on the SDS-PAGE than lento and S-KM as the KM mutation abolished the glycosylation site. These data demonstrated that the R and S mutations at the F protein cleavage site affected F protein cleavage and S-KN is more efficient than S. Since the F and HN gene each was cloned in the pVitro2-neo-MCS vector encoding an EGFP gene, syncytial formation can be visualized by the fused green cells. Large syncytial formation was observed in wt F and HN plasmid transfected 293 cells. All the F mutants with R, S or S-KM residues in the F protein cleavage sites resulted in greatly reduced syncytial formation.

Example 17. r73T-R116i Virus with 198 nt Insertion Exhibited Slower Growth and Differential RNA and Protein Synthesis Profile in DF-1 Cells Compared to Vero Cells R116i virus with 198 nt inserted between the HN-L junction exhibited slower growth kinetics in chicken DF-1 cells under high moi condition as shown in FIGS. 6B and 6D. The growth difference of R116i with 198 nt insertion was reduced compared to the wt and the R virus that does not have the inergenic insertion at the earlier time points of infection (10-20 h). In Vero cells, the growth difference among these viruses was not very apparent (FIGS. 6C and 6E). To understand if the inergenic insertion in the R116i viruses affected viral RNA transcription and replication, viral RNA and protein synthesis in infected DF-1 cells were examined by Northern and Western blotting analyses, respectively (FIGS. 6F and 6G). The RNA and protein synthesis of R116i with 198 nt insertion were greatly reduced in infected DF-1 cells. In contrast, in infected Vero cells, the upstream gene transcript such as the NP mRNA was greatly increased in R118i-198 or 198RSV infected cells while the genomic RNAs of these two viruses were reduced. The level of the L protein of these two viruses was reduced, but the other viral protein products were increased such as NP, F and HN as shown in FIGS. 6H and I. The data obtained in FIGS. 6F-I were conducted at the high moi condition (moi=5). RNA and protein synthesis were further evaluated under the low moi condition (moi=0.001). Again, R116i-198 or 198RSV had differential RNA and protein synthesis profile in DF-1 and Vero cells. Both RNA and protein synthesis of R116i-198 or 198RSV were reduced in chicken DF-1 cells (FIG. 6J). In contrast, the upper stream RNA and protein were increased in Vero cells but the level of L mRNA and L protein was reduced due to the intergenic insertion of 198 nt sequence (FIG. 6K). Viral RNA and protein synthesis were further compared in human cell lines, human fibrosarcoma HT1080 and Hela cells, and DF-1 cells (FIG. 6L). These data confirmed that R116i-198 or 198RSV had differential expression, the upstream RNA and protein synthesis increased while the L protein expression was down regulated. These data explained why R116i-198 or 198RSV viruses replicated well in the mammalian cell lines such as Vero, human HT1080 and Hela cells but did not grow well in embryonated chicken eggs and chicken DF-1 cells. It also provided basis of reduced chicken pathogenicity of these R116i viruses as demonstrated by their low intra-cerebral pathogenicity index (ICPI) value.

Example 18. Mouse GM-CSF Transgene Expression Had Lower Tumor Growth Inhibition Efficacy than Human GM-CSF Transgene Expression in R116i-198RSV, but not in S116-KM FIG. 11C compared contribution of the mGM-CSF with hGM-CSF transgene expression on oncolytic activity of R116i-198RSV and S116-KM in HT1080 xenograft mouse tumor model. hGM-CSF transgene does not cross react with mGM-CSF and it was therefore used as the control. The mGM-CSF transgene in R116i-198 administered intra-tumorally had lower efficacy in tumor growth inhibition compared to hGM-CSF. Similar tumor growth inhibition of mGM-CSF and hGM-CSF was observed for S116 virus. Viral titers in viral treated tumors were determined by plaque assay (FIG. 11D). On day 4 post tumor injection, similar titer was detected for the R116i-198RSV and S116-KM with mGM-CSF or hGM-CSF pairs. However, on day 7 post injection, R116i-198RSV with mGM-CSF was not detected while R116i-198RSV with hGM-CSF still had viral titer of approximately 4.5 logs/g tissue. There was no difference in viral titers of S116 with hGM-CSF or mGM-CSF. These data indicate that the expression of mGM-CSF by R116i facilitated viral clearance.

Immune cell infiltration in virus infected tumor tissues was examined (FIG. 11E). R116i-198RSV with mGM-CSF had the greatest number of neutrophil, NK and macrophage cells in the treated tumors compared to R116-198RSV with hGM-CSF and the S116 hGM-CSF and mGM-CSF pair. The cytokines and chemokines in virus treated tumor were determined by luminex assay (FIG. 11F). All four viruses stimulated cytokine and chemokine production by many folds compared to the untreated tumor tissues. The expression of mGM-CSF by R116i is about 10-fold higher than S116 (106.7 vs 9.9-fold).

FIG. 11G showed similar tumor growth inhibition activity of R116i with 198 or 318 nt inserted between the HN-L junction containing the same hGM-CSF transgene in the HT1080 xenograft mouse tumor model. The 318 nucleotide insertion in the HN-L junction did not reduce viral oncolytic virus activity.

Example 19. Evaluation of Complement-Mediated NDV Inactivation and Role of Regulatory Proteins in Complement Evasion The complement (C') system is a major defense system against microbial invasion in the host. There are about 30 different glycoproteins in the human complement system, of which 20 act in plasma and 10 are regulators or receptors on cell membranes. Membrane bound C' regulators (RCA) include 4 well characterized molecules: hCD46, hCD55, hCD59 and hCD35. Their main function is to protect human cells against autologous complement attack without affecting the role of C' in eliminating foreign agents. These RCA proteins are host species-specific. NDV used for viral therapy in the past was generally produced in embryonated chicken eggs. It is expected that NDV oncolytic virus administered by intravenous injection to cancer patients might be cleared rapidly, therefore reducing effective viral dosing. Since enveloped viruses produced from human cells incorporate RCA proteins during their egress from the infected cells, it is therefore desirable to produce NDV in human cell culture to reduce C' mediated viral lysis or inactivation.

Sensitivity of NDV to C' mediated inactivation was evaluated by examining NDV produced in embryonated chicken eggs, human 293 and Hela S3 suspension cell lines (FIG. 17). Virus grown in eggs was sensitive to C' inactivation, serum inhibition was abolished by heat treatment (56° C. for 30 min) of the serum. Guinea pig complement had the similar level of viral inactivation effect (data not shown), confirming that viral inactivation was due to C'. In addition, the viruses produced from Hela cells were more resistant to human C' mediated viral inactivation than 293 cells and eggs. Thus, the data suggest that Hela cells are better than 293 cells for NDV oncolytic virus production, which likely resulted in slower viral clearance and thus increased the therapeutic index.

To explain why the NDV produced from the Hela S3 cells is more resistant to C', 293 and Hela S suspension cell lines were evaluated for the levels of the 4 well characterized human RCA proteins, hCD46, hCD55, hCD59 and hCD35. hCD35 was not detected in the 293 and Hela cells by Western analysis and the data are therefore not shown in FIG. 18. hCD46, hCD55, and hCD59 were detected in higher abundance in Hela S3 cells than in 293 cells. Thus, the levels of RCA proteins inversely correlate with viral sensitivity to C'.

In order to determine if all three RCA proteins regulate C' function, hCD55, hCD59 or hCD46 transgene was inserted into NDV genome by reverse genetics and recombinant viruses expressing each of the three RCA proteins were produced. Western blot analysis showed that each of these RCA proteins was expressed by virus and incorporated into virions (FIG. 19). hCD55 was determined to be the major RCA protein conferring to C' inactivation function (FIG. 20). The virus expressing hCD55 produced in eggs with hCD55 incorporated into virions was most resistant to C' mediated inactivation, which is very close to the viruses produced in Hela cells. In comparison, hCD46 had marginal improvement in terms of viral resistant to C' inactivation and hCD59 did not have detectable role in C' regulation.

In conclusion, to reduce viral clearance for oncolytic viral therapy and to improve NDV therapeutic index, Hela cells are considered the cell line of choice for viral production.

The results described herein were obtained using the following materials and methods.

Cells and Viruses.

The following cell lines and corresponding media were used: African green monkey kidney Vero cell line (ATCC) and human fibrosarcoma (HT1080, ATCC), Eagle's minimal essential medium (EMEM, Hyclone) with 10% fetal bovine serum (FBS); Vero clone 51D11 line (MedImmune), serum free media (SFMMegaVir, Hyclone) with 1% glutamine; normal human skin fibroblast cells (CCD1122Sk, ATCC), ATCC formulated Iscove's Modified Dulbecco's medium (IMEM) with 10% FBS. Recombinant Newcastle disease viruses (NDV) were grown in the allantoic cavities of 10-11-day-old specific-pathogen free (SPF) embryonated chicken eggs, Vero, or Vero clone 51D11 cells.

Construction of NDV Antigenomic cDNA and Supporting Plasmids NP, P and L.

Viral RNA of NDV strain 73T was obtained from Dr. Mark Peeples (Nationwide Children's Hospital). NDV sequences (GenBank) were aligned to obtain consensus sequences to design DNA oligonucleotides for RT-PCR of the viral RNA. Six subgenomic cDNA overlapping fragments spanning the entire NDV genome were generated by high-fidelity RT-PCR (FIG. 1). The pUC19 vector was modified to include an 88 nt oligonucleotide linker containing restriction sites introduced between the EcoRI and HindIII sites for sequential assembly of full-length antigenomic cDNA of the NDV 73T strain. In addition, the 73T strain cDNA plasmid (p73T) contains a 27 nucleotide (nt) T7 RNA polymerase promoter at the 5'end and a 189 nt containing HDV antigenome ribozyme sequence and a T7 RNA polymerase transcription-termination signal at the 3' end. To generate non-virulent NDV, the sequence encoding the protease cleavage site of the fusion protein was modified by site-directed mutagenesis to those of the non-virulent NDV LaSota strain (lentogenic, lento) or glycoprotein B (gB) of cytomegalovirus (S116). For construction of NP, P and L expression plasmids, the protein open reading frames (ORF) were amplified by RT-PCR and cloned into plasmid pCITE2a under the control of the T7 RNA polymerase.

Insertion of the Transgene into the NDV.

For insertion of a transgene at the P-M junction, an AfeI restriction site was introduced at nt 3148 in the subclone plasmid containing SacII-PmlI fragment (FIG. 2A). The cDNA encoding human or mouse granulocyte-macrophage colony-stimulating factor (GM-CSF) or interleukin 2 (IL-2) was codon optimized and synthesized by DNA 2.0. A gene cassette contains the gene end (GE) of N, the gene start (GS) of P and the open reading frame (ORF) of the transgene, which was inserted into the AfeI site. The SacII-PmlI fragment from the resulting plasmid was shuffled into plasmid r73T and named as p73T-P1.

To insert a transgene into the HN-L junction between the HN ORF and the gene end signal (GE) sequence of HN, an AfeI restriction site was introduced at nt 8231 in the plasmid containing the AgeI-XbaI fragment (FIG. 2A). The gene cassette was generated by PCR using a pair of phosphate sense and antisense primers (Table 4) and inserted into AfeI site.

TABLE 4

Oligonucleotide primer sequences for insertion of transgene transcriptional cassette.

| Transgene | Sense | SEQ ID NO: | Antisense | SEQ ID NO: |
|---|---|---|---|---|
| hGM-CSF | 5'<u>TTAAGAAAAAAT</u>ACGGGTAGAAcgc cgccacc*ATGTGGCTGCAGAGCCTGCTG* 3' | 22 | 5' *TCATTCCTGCACGGGCTCCCAGCAGTC* 3' | 23 |
| mGM-CSF | 5'<u>TTAAGAAAAAAT</u>ACGGGTAGAAcgc cgccacc*ATGTGGCTGCAGAACCTGCTG TTCCTGG* 3' | 24 | 5'*GTATCACTTCTGGCCGGGTTTCTTGCACTC* 3' | 25 |
| hIL-2 | 5'<u>TTAAGAAAAAAT</u>ACGGGTAGAAcgc cgccacc*ATGTATAGGATGCAACTFCTG TC* 3' | 26 | 5' *GTCAAGTCAGGGTAGAGATAATGCTCTGGC* 3' | 27 |
| mIL-2 | 5'<u>TTAAGAAAAAAT</u>ACGGGTAGAAcgc cgccacc*ATGTATTCAATGCAGCTGGCA TC* 3' | 28 | 5' *GAGTTACTGAGGGGAAGTTGAAATG* 3' | 29 |
| EGFP | 5'<u>TTAAGAAAAAAT</u>ACGGGTAGAAcgc cgccacc*ATGGTGAGCAAGGGCGAGGA GCTG* 3' | 30 | 5'*AATTACTTGTACAGCTCGTCCATGC* 3' | 31 |
| EGFP (HN-L) | 5'<u>ACGGGTAGGAC</u>*ATGGTGAGCAAGG GCGAGG* 3' | 32 | 5' <u>TTTTTTCTAA</u>CATAGTATAATTAAATCACCAA GGATACAATTGGCCAGAAAAAGAGCCTATTAAT ATGTGATTTTCGCGTTACTTGTACAGCTCGTCCA*T* 3' | 33 |

The gene end (GE) and gene start (GS) sequences are underlined.
Kozak sequence is shown in lower case.
The sequences correspond to 5' or 3' sequences of the transgene are shown in italics.
Except for the EGFP (H-N), all other primer pairs can be used for inserting the transgene between G-M or HN-L.
hGM-CSF: human granulocyte-macrophage colony-stimulating factor;
mGM-CSF: mouse GM-CSF;
hIL-2 and mIL-2 correspond to human and mouse interleukin 2 (IL-2), respectively.?

The AgI-XbaI fragment from the resulting plasmid was shuffled into plasmid p73T, yielding p73T-HN1. Another strategy to insert sequence at the HN-L junction was to insert a transgene cassette or sequences from other paramyxoviruses between the gene end signal (GE) of the HN and the gene start signal (GS) of the L (FIG. 4) at AfeI site that was introduced at nt 8359. The FL cDNA plasmid was designated p73T-R116i. Since the NDV genome length has to be in a multiple of 6 nucleotides (rule of 6), the antigenomic cDNA of various constructs were made to follow the rule of 6.

To insert two transcriptional cassettes into the P-M junction, an AfeI site was introduced at the end of the ORF of GM-CSF (nt 3619) (FIG. 2B). The IL-2 ORF was amplified using a pair of phosphate sense and antisense primers containing the GE and GS sequences and inserted at the AfeI site. The SacII-PmlI fragment from the resulting plasmid including GM-CSF and IL-2 transcriptional cassettes was swapped back into plasmid r73T, yielding p73T-P2.

Generation of r73T Chimeric Viruses Containing Ectodomain of Other Paramyxovirus.

The chimeric NDV genomic DNA was produced by replacing the F and HN of NDV with those of pigeon paramyxovirus 1 (PPMV-1). The C-terminal coding sequence for the cytoplasmic tail and transmembrane portion of NDV 73T F (amino acid residues 503 to 553) was joined with the ectodomain F protein coding sequence of PPMV-1 (residues 1 to 502), the N-terminal coding sequences of the NDV HN (amino acid sequence residues 1 to 45) was fused with the HN (residues 46 to 577) by overlapping PCR reactions using GeneArt kit (Invitrogen). The amplified fragment was digested and cloned into PmlI-AgeI digested NDV cDNA. The parainfluenza virus 5 (PIV-5) F or HN were introduced into the NDV 73T antigenomic cDNA by a similar cloning strategy. The PIV5 F (residues 1 to 486) ectodomain was fused with the transmembrane and the cytoplasmic tail of NDV 73T F (residues 503 to 553). The NDV HN (residues 1 to 45) was joined with the PIV5 HN ectodomain (residues 36 to 565). The cDNA fragment was cloned into PmlI-AgeI digested NDV antigenomic cDNA.

Recovery of Recombinant NDV from Transfected cDNA Plasmids.

The mammalian cell line expressing the T7 RNA polymerase such as the BHK-T7 cells were transfected with the three plasmids expressing the NDV NP, P, and L proteins (0.4 µg, 0.4 µg, and 0.2 µg per well of a 6-well dish, respectively) and a plasmid encoding the NDV antigenomic cDNA (1.6 µg) using Lipofectamine 2000. Three days after transfection, the cell culture supernatant was injected into the allantoic cavities of 10 to 11-day-old SPF embryonated chicken eggs or passaged in Vero cells to amplify the rescued virus. Recovery of the virus was confirmed by hemaglutination assay using 1% chicken red blood cells (RBCs). Rescue of viruses can also be performed by electroporation of the NP, P, L, antigenomic cDNA plasmids together with a plasmid expressing the T7 RNA polymerase into Vero cells as previously described (Kaur et al., Optimization of plasmid-only rescue of highly attenuated and temperature-sensitive respiratory syncytial virus (RSV) vaccine candidates for human trials. 2008 J. Virol. Methods 153:196-202). The recovered virus was confirmed by sequencing of RT-PCR amplified cDNA.

In Vitro Passage to Select Virus with Stable F Protein Cleavage Site.

To examine if the F protein cleave sequence (FPCS) was stable and if any stabilizing mutations could be selected after passaging in tissue culture, r73T-S116 were serially passaged for 10 times in Vero and human fibrosarcoma HT1080 cells at MOI of 0.01. After every 2-3 passages, viral RNA was isolated from the culture media, cDNA was amplified by RT-PCR and the F and/or HN genes were sequenced.

Virus Plaque Morphology in Vero Cells and Titer Quantitation by Plaque Assay.

Vero cells on a 6-well plate were infected with serial diluted virus and incubated under 1% methylcellulose overlay at 37° C. for 3 days or 6 days for plaque morphology in the presence of trypsin (TrpyLE™, Invitrogen) for viral titer quantitation. The cell monolayers were fixed with methanol and stained with chicken anti-NDV polyclonal antibody against whole inactivated NDV virus followed by exposure to horseradish peroxidase (HRP)-conjugated anti-chicken antibody (Dako).

Virus Chicken Pathogenicity Test by Egg Mean Death Time (MDT) and Intracerebral Pathogenicity Index (ICPI) Assays.

The pathogenicity of the r73T viruses was determined by the mean death time (MDT) test in 10-day-old SPF embryonated chicken eggs. The ICPI test in 1-day-old SPF chicks was conducted at the USDA's National Veterinary Service Laboratory (NVSL, Ames, Iowa). For the MDT test, 0.1 ml of a series of 10-fold dilution between $10^{-6}$ and $10^{-9}$ was inoculated into the allantoic cavities of 8-10 of 9-10-day-old eggs per dilution and incubated at 37° C. The eggs were examined twice a day for 7 days to record the time of embryo death. The MDT was calculated as the mean time (hr) for the minimum lethal dose of virus to kill all the inoculated embryos. The MDT assay provides a reasonable prediction of virus pathogenicity. The viruses with MDT <60 hr are normally verogenic (virulent) strains; with MDT=60 to 90 hr, mesogenic (intermediate) strains; >90 h as letogenic (avirulent) strains. For the ICPI test, 0.05 ml of a 1:10 dilution of fresh infective allantoic fluid for each virus was inoculated into group of 10 1-day-old SPF chicks via the intracerebral route. The birds were observed for clinical symptoms and mortality once every 8 hr for a period of 8 days. At each observation, the birds were scored as follows: 0 if normal, 1 if sick, and 2 if dead. The ICPI is the mean of the score per bird per observation over the 8-day period. The ICPI values ranges from 0.0 to 2.0. The low virulent (LoND): ICPI<0.7; virulent (vND): ICPI≥0.7.

Virus Cell Killing Assessed by Cell Viability Assay.

The cells were plated in 96-well plates at $5\times10^3$ cells/well overnight infected with r73T at various MOI. Cell viability was determined by CellTiter Glo kit (Promega) per manufacture's manual. The relative percent of surviving cells is determined by comparing the ATP level of each testing sample to the untreated sample control of 100% viable. The data presented in the table is relative percent of the killed cells.

The Effect of NDV Tumor Killing Assessed in the Subcutaneous HT1080 Xenograft Model.

Athymic NCR homogenous nude mice (Taconic) were implanted subcutaneously (s.c.) with $5\times10^6$ HT1080 cells (in 100 μL PBS) into one flank. Viral treatment started when tumors reached a volume of 65-300 $mm^3$. Recombinant 73T in 100 n1 was administered at different dose levels either locally by intratumor (i.t) injection or systemically by intratumor (i.t) injection into the tail vein, respectively. The control animals were injected with 100 μL PBS only. Tumor growth was measured using a digital caliper, and tumor volume was calculated as 0.5×(height)×width×length ($mm^3$). Mice were sacrificed when the body weight dropped by 20% of the original body weight or the tumor volume exceeded 2000 $mm^3$.

Viral Biodistribution in the HT1080 Xenograft Mice.

Nine Nude mice bearing HT1080 human fibrosarcoma xenograft subcutaneous tumors were i.v injected with $10^8$ pfu of r73T-R116i-hGM-CSF. Three mice were terminated at 1, 4, and 8 day(s) post-injection. One mouse injected with PBS was terminated on day 8. The tumors, lungs, spleen, ovaries and serum samples were collected. The infectious virus titer in the tissue homogenates was quantified by plaque assay.

Quantitation of the GM-CSF Protein Level by ELISA.

Tumors from NDV infected and PBS injected mice were homogenized in PBS using gentle MACS Dissociator (Miltenyi Biotec) per manufacturer's instruction. The supernatant from homogenized tissues or serum collected from mice were tested for the level of GM-CSF by a Duoset ELISA kit (R&D).

Statistical Analysis

All statistical analyses were performed using the GraphPad Prism 6.0 software. The unpaired t-test was used to assess differences in tumor regression between groups. GraphPad Prism software was also used to calculate the IC50 of rNDV 73T for in vitro cell killing in normal and tumor cells.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, CAS, and accession numbers mentioned in this specification are herein incorporated by reference to the same extent as if each independent patent, publication, and accession number was specifically and individually indicated to be incorporated by reference.

What is claimed is:

1. An attenuated Newcastle disease virus (NDV) 73T strain comprising an F protein cleavage site derived from glycoprotein B (gB) of cytomegalovirus (CMV), wherein the F protein cleavage site comprises a modified F protein cleavage sequence (FPCS) comprising R116: $^{111}$H-N-R-T-K-R/F-I$^{118}$ (SEQ ID NO: 5) and wherein the virus further comprises an increased HN-L intergenic region consisting of a non-coding sequence of 198 or 318 nt in length.

2. The attenuated Newcastle disease virus of claim 1, wherein the non-coding sequence is derived from a paramyxoviruses type-1 (APMV-1), a respiratory syncytial virus (RSV) or a random sequence.

3. The attenuated Newcastle disease virus of claim 1, wherein the virus comprises one or more heterologous polynucleotide sequences inserted at the P-M junction and/or the HN-L junction.

4. The attenuated Newcastle disease virus of claim 3, wherein the heterologous polynucleotide sequence is a transgene encoding a polypeptide that enhances the oncolytic properties of the virus.

5. The attenuated Newcastle disease virus of claim 4, wherein the transgene encodes a cytokine, cell surface ligand, and/or chemokine.

6. The attenuated Newcastle disease virus of claim 5, wherein the cytokine is selected from the group consisting of GM-CSF, IL-2, IL-21, IL-15, IL-12, and IL-12p70.

7. The attenuated Newcastle disease virus of claim 6, wherein the cytokine is human GM-CSF.

8. A method of selectively killing tumor cells, the method comprising contacting a tumor cell with the attenuated Newcastle disease virus of claim 1.

9. A method of inducing tumor regression in a subject, the method comprising contacting a tumor cell with the attenuated Newcastle disease virus of claim 1.

10. A method of reducing tumor cell survival or proliferation, the method comprising contacting a tumor cell with the attenuated Newcastle disease virus of claim 1.

11. A method of treating a neoplasia in a subject, the method comprising administering to the subject an effective amount of an attenuated Newcastle disease virus of claim 1.

12. A nucleic acid comprising the full length cDNA of 73T, wherein the nucleic acid encodes a modified F protein cleavage sequence selected from the group consisting of:

S116: $^{111}$H-N-R-T-K-S/F$^{117}$ (SEQ ID NO: 1);
S116K: $^{111}$H-N-K-T-K-S/F$^{117}$ (SEQ ID NO: 2);
S116M: $^{111}$H-N-R-M-K-S/F$^{117}$ (SEQ ID NO: 3);
S116KM: $^{111}$H-N-K-M-K-S/F-I$^{118}$ (SEQ ID NO: 4); and
R116: $^{111}$H-N-R-T-K-R/F-I$^{118}$ (SEQ ID NO: 5).

13. A vector comprising full length cDNA of 73T, wherein the vector encodes a modified F protein cleavage sequence selected from the group consisting of:

S116: $^{111}$H-N-R-T-K-S/F$^{117}$ (SEQ ID NO: 1);
S116K: $^{111}$H-N-K-T-K-S/F$^{117}$ (SEQ ID NO: 2);
S116M: $^{111}$H-N-R-M-K-S/F$^{117}$ (SEQ ID NO: 3);
S116KM: $^{111}$H-N-K-M-K-S/F-I$^{118}$ (SEQ ID NO: 4); and
R116: $^{111}$H-N-R-T-K-R/F-I$^{118}$ (SEQ ID NO: 5).

14. A virulent particle comprising the nucleic acid of claim 12.

15. A host cell infected with the attenuated Newcastle disease virus of claim 1.

16. A host cell comprising the nucleic acid of claim 12.

17. The attenuated Newcastle disease virus of claim 7, wherein the increased HN-L intergenic region non-coding sequence is 198 nt in length.

18. The attenuated Newcastle disease virus of claim 7, wherein the increased HN-L intergenic region non-coding sequence is 318 nt in length.

19. The attenuated Newcastle disease virus of claim 6, wherein the cytokine is IL-12.

20. The attenuated Newcastle disease virus of claim 19, wherein the increased HN-L intergenic region non-coding sequence is 198 nt in length.

* * * * *

SEQUENCE LISTING

```
<160> NUMBER OF SEQ ID NOS: 54

<210> SEQ ID NO 1
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 1

His Asn Arg Thr Lys Ser Phe
1               5

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

His Asn Lys Thr Lys Ser Phe
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

His Asn Arg Met Lys Ser Phe
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

His Asn Lys Met Lys Ser Phe Ile
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

His Asn Arg Thr Lys Arg Phe Ile
1               5

<210> SEQ ID NO 6
<211> LENGTH: 30866
<212> TYPE: DNA
<213> ORGANISM: Newcastle disease virus

<400> SEQUENCE: 6
tacgtataat acgactcact atagggacca aacagagaat

```
cgaaggagca attgaagttg gacgggtaga aggtgtgaat ctcgagtgcg agcccgaagc      120
acaaactcga gaaagccttc tgccaacatg tcttccgtat ttgacgagta cgaacagctc      180
ctcgcgtctc agactcgccc caatggagct catggaggag gggaaaaggg gagtaccttta     240 aaagtagacg tcccggtatt cactcttaac agtgatgacc cagaagatag gtggaacttt     300
gcggtattct gcctccggat tgctgttagc gaagatgcca acaaaccact caggcaaggt     360
gctctcatat ctcttttatg ctcccactca caagtgatga ggaaccatgt tgcccttgca     420
gggaaacaga atgaagccac attggccgtg cttgagattg atggctttgc caacggtatg     480
ccccagttca acaataggag tggagtgtct gaagagagag cacagagatt cgcgatgata     540
gcagggtctc tccctcgggc atgcagtaat ggcaccccgt tcgtcacagc cggggccgaa     600
gatgatgcac cagaagacat caccgatacc tggagaggga tcctctctat ccaggcccaa     660
gtatgggtca cagtagcaaa agccatgact gcgtatgaga ctgcagatga gtcagaaaca     720
agacgaatca ataagtatat gcagcaaggc agggtccaaa agaaatacat cctctacccc     780
gtatgcagga gcacaatcca actcacgatc agacagtctc ttgcagtccg catcttttttg    840 gttagcgagc tcaagagagg ccgcaacacg gcaggtggta cctctactta ttataaccta     900
gtaggggacg tagactcata tatcaggaat accgggctta ctgcattctt cctgacactc     960
aagtacggaa tcaacaccaa gacatcagcc cttgcactta gtagcctctc aggcgacatc     1020
cagaagatga agcagctcat gcgtttgtat cggatgaaag gagataatgc gccgtacatg    1080
acattgcttg gtgatagtga ccagatgagc tttgcgcctg ccgagtatgc acaactttac    1140
tccttcgcca tgggtatggc atcagtccta gataaaggta ccgggaaata ccaatttgcc    1200 agggactttta tgagcacatc attctggaga cttggagtag agtacgctca ggctcaggga   1260
agtagcatta acgaggatat ggctgccgag ctaaagctaa ccccagcagc aaggagaggc    1320
ctggcagctg ctgcccaacg agtctccgag gagaccagca gcatagacat gcctactcaa    1380
caagtcggag tcctcactgg gctcagcgag ggggggtccc aagccctaca aggcggatcg    1440
aatagatcgc aagggcaacc agaagccggg gatggggaga cccaattcct ggatctgatg    1500
agagcggtag caaatagcat gagggaagcg ccaaactctg cacagggcac tccccaatcg    1560
gggcctcccc caactcctgg gccatcccaa gataacgaca ccgactgggg gtattgattg    1620
acaaaaccca gcttgcttcc acaaaatcat cccaataccc tcacccgtag tcgacccctc    1680
gatttgcggc cctacatgac cacaccctca aacaaacatc cccctctttc ctccctcccc    1740
ctgctgtaca actccgcacg ccctaggtac cacaggcaca atgcggctca ctaacaatca    1800
aaacagagcc gaggaaatta gaaaaagta cgggtagaag agggatattc agagaccagg     1860
gcaagtctcc cgagtctctg ctctctcctc tacctgatag attaggacaa atatggccac    1920
ctttacagat gcggagatcg acgagctatt tgagacaagt ggaactgtca ttgacaacat    1980
aattacagcc cagggtaaac cagcagagac tgtgggaagg agtgcaatcc cacatggcaa    2040
aaccaaggcg ctgagcgcag catgggagaa gcatgggagc atccagccac cagccagtca    2100
agacacccct gatcgacagg acagatctga caaacaacca tccacacccg agcaagcgac    2160
cccgcatgac agcccgccgg ccacatccgc cgaccagccc cccacccagg ccacagacga    2220
agccgtcgac acacagctca ggaccggagc aagcaactct ctgctgttga tgcttgacaa    2280
gctcagcaat aaatcatcca atgctaaaaa gggcccatgg tcgagccccc aagagggggaa   2340 ccaccaacgt ccgactcaac agcagggaag tcaacccagc cgcggaaaca gtcaggaaag    2400
```

```
accacagaac caagtcaagg ccgcccctgg aaaccagggc acagacgcga acacagcata    2460
tcatggacaa tgggaggagt cacaactatc agctggtgca accoctcatg ctctccgatc    2520 aaggcagagc caagacaata cccttgtatc tgcggatcat gtccagccac ctgtagactt    2580
tgtgcaagcg atgatgtcta tgatggaggc aatatcacag agagtaagta aggttgacta    2640
tcagctagat cttgtcttga aacagacatc ctccatccct atgatgcggt ccgaaatcca    2700
acagctgaaa acatctgttg cagtcatgga agccaatttg gaatgatga agattctgga    2760 tcccggttgt gccaacgttt catctctgag tgatctacgg gcagttgccc gatctcaccc    2820
ggttttagtt tcaggccctg agacccatc tccctatgtg actcaaggag gcgaaatggc    2880
acttaataaa ctttcgcaac cagtgccaca tccatctgaa ttgattaaac ccgccactgc    2940
atgcgggcct gatataggag tggaaaagga cactgtccgt gcattgatca tgtcacgccc    3000
aatgcacccg agttcttcag ccaagctcct aagcaagcta gatgcagccg ggtcgatcga    3060
ggaaatcagg aaaatcaagc gccttgcact aaatggctaa ttaccactgc cacacgtagc    3120
gggtccccgt ccactcggca tcacacggaa tctgcaccga gtcccccccc gcagacctaa    3180
ggtccaactc tccaagtggc aatcctctct cgcttcctca gccccactga atgatcgcgc    3240
aaccgtaatt aatctagcta cattaaggat taagaaaaaa tacgggtaga attggaatgc    3300
cccaattgtg ccaagatgga ctcatctagg acaattgggc tgtactttga ttctgcccat    3360
tcttctagca acctgttagc atttccgatc gtcctacaag acacaggaga tgggaagaag    3420
caaatcgccc cgcaatatag gatccagcgc cttgactcgt ggactgatag taaagaagac    3480
tcagtattca tcaccaccta tggattcatc tttcaggttg ggaatgaaga agccactgtc    3540
ggcatgatca atgataatcc caagcgcgag ttactttccg ctgcgatgct ctgcctagga    3600
agcgtcccaa ataccggaga ccttgttgag ctggcaaggg cctgtctcac tatggtagtc    3660
acatgcaaga agagtgcaac taatactgag agaatggttt tctcagtagt gcaggcaccc    3720
cgagtgctgc aaagctgtag ggctgtggca gacaaatact catcagcgaa tgcagtcaag    3780
cacgtgaaag cgccagagaa gatccccggg agtggaaccc tagaatacaa ggtgaacttt    3840
gtctccttga ctgtggtacc gaagaaggat gtctacaaga tcccaactgc agtattgaag    3900
gtttctggct cgagtctgta caatcttgcg ctcaatgtca ctattaatgt ggaggtagac    3960
ccgaggagtc ctttggttaa atctctgtct aagtctgaca gcggatacta tgctgacctc    4020
ttcttgcata ttggacttat gaccaccgta gataggaagg ggaagaaagt gacttttgac    4080
aagctagaaa agaagataag gagacttgat ctatctgtcg ggctcagtga tgtgctcgga    4140
ccttccgtgc tggtaaaagc aagaggtgca cggaccaagc ttttggcacc tttcttctct    4200
agcagtggga cagcctgcta tcccatagca aatgcctctc cccaggtggc caagatactc    4260
tggagtcaaa ccgcgtgcct gcggagcgtt aaaatcatta tccaagcagg tacccaacgc    4320
gctgtcgcag tgaccgctga ccacgaggtt acctctacta agctggagaa ggggcacacc    4380
cttgccaaat acaatccttt taagaaataa gctgcgtttc tgagattgcg ctccgcccac    4440
tcacccagag catcatgaca ccaaaaacta atctgtcttg attatttaca gttagtttac    4500
ctgtctatca aattagaaaa aacacgggta gaagattctg gatcccggtt ggcgccttct    4560
aggtgcaaga tgggcccag accttctacc aagaacccag cacctatgat gctgactgtc    4620
cgggtcgcgc tggtactgag ttgcatctgt ccggcaaact ccattgatgg caggcctctt    4680
gcggctgcag gaattgtggt aacaggagac aaagcagtca acatatacac ctcatcccag    4740
acaggatcaa tcatagttaa gctcctccca aacctgccca aggataagga ggcatgtgcg    4800
```

```
aaagcccct  tggatgcata  caacaggaca  ttgaccactt  tgctcacccc  ccttggtgac    4860
tctatccgta  ggatacaaga  gtctgtaact  acatctggag  ggaggagaca  gaaacgcttt    4920
ataggcgcca  ttattggcgg  tgtggctctt  ggagttgcaa  ctgctgcaca  aataacagcg    4980
gccgcagctc  tgatacaagc  caaacaaaat  gctgccaaca  tcctccgact  taaagagagc    5040
attgccgcaa  ccaatgaggc  cgtgcatgag  gtcactgacg  gattatcgca  actagcagtg    5100
gcagttggga  agatgcagca  gtttgtcaat  gaccaattta  taaaacaac   tcaggaatta    5160 ggctgcatca  gaattgcaca  gcaagttggc  gtagagctca  acctgtatct  aaccgaattg    5220
actacagtat  tcggaccaca  aatcacttca  cctgccttaa  acaagctgac  tattcaggca    5280
ctttacaatc  tagctggtgg  gaatatggat  cacttgttga  ctaagttagg  tgtagggaac    5340
aatcaactca  gctcattaat  cggtagcggc  ttaatcaccg  gcaaccctat  tctgtacgac    5400
tcacagactc  aactcttggg  tatacaggta  actctacctt  cagtcgggaa  cctaaataat    5460
atgcgtgcca  cctacttgga  aaccttatcc  gtaagcacaa  ccaggggatt  tgcctcggca    5520
cttgtcccaa  aagtggtgac  acaggtcggt  tctgtgatag  aagaacttga  cacctcatat    5580
tgtatagaaa  ccgacttgga  tttatattgt  acaagaatag  taacattccc  tatgtcccct    5640
ggtatttatt  cctgcttgag  cggcaataca  tcggcctgta  tgtactcaaa  gaccgaaggc    5700
gcactcacta  cgccatacat  gactatcaaa  ggctcagtca  tcgctaactg  caagatgaca    5760
acatgtagat  gtgtaaaccc  cccgggtatc  atatcgcaaa  actatgggga  agccgtgtct    5820
ctaatagata  agcaatcatg  caatgtttta  tccttagacg  ggataacttt  aaggctcagt    5880
ggggaattcg  atgcaactta  tcagaagaat  atctcaatac  aagattctca  agtaataata    5940
acaggcaatc  ttgatatctc  aactgagctt  gggaatgtca  caactcgat   cagtaatgct    6000 ttgaataagt  tagaggaaag  caacagcaaa  ctagacaaag  tcaatgtcaa  actgaccagc    6060
acatctgctc  tcattaccta  tatcgttttg  actatcatat  ctcttgtttt  tggtatactt    6120
agcctggttc  tagcatgcta  cctaatgtac  aagcaaaagg  cgcaacaaaa  gaccttatta    6180
tggcttggga  ataatacccct  agatcagatg  agagccacta  caaaaatgtg  aacacagatg    6240
aggaacgaag  gtatccctaa  tagtaatttg  tgtgaaagtt  ctggtagtct  gtcagttcgg    6300
agagtttaga  aaaaactacc  ggttgtagat  gaccaaagga  cgatatacgg  gtagaacggt    6360
aagagaggcc  gccctcaat   tgcgagccgg  gcttcacaac  ctccgttcta  ccgcttcacc    6420
gacagcagtc  ctcagtcatg  gaccgcgcag  ttagccaagt  tgcgttagag  aatgatgaaa    6480
gagaggcaaa  aaatacatgg  cgcttgtat   tccggattgc  aatcttactc  ttaacagtag    6540
tgaccttagc  tacatctgta  gcctcccttg  tatatagcat  ggggggctagc  acacctagcg    6600 accttgtagg  cataccgacc  aggatttcca  gggcagaaga  aaaaattaca  tctgcacttg    6660
gttccaatca  agatgtagta  gataggatat  ataagcaagt  ggcccttgag  tctccgttgg    6720
cattgttaaa  cactgagatc  acaattatga  acgcaataac  atctctctct  tatcagatta    6780
atggagctgc  gaacaacagc  gggtgggggg  cacctatcca  tgacccagat  tttatcgggg    6840
ggataggcaa  agaactcatt  gtagatgatg  ctagtgatgt  cacatcattc  tatccctctg    6900
catttcaaga  acatctgaat  tttatcccgg  cgcctactac  aggatcaggt  tgcactcggt    6960
taccttcatt  tgacatgagt  gctacccatt  actgctacac  tcataatgta  atattgtctg    7020
gatgcagaga  tcactcacac  tcacatcagt  atttagcact  tggtgtgctc  cggacatctg    7080
caacagggag  gatattcttt  tctactctgc  gttccatcaa  tctggatgac  acccaaaatc    7140
```

```
ggaagtcttg cagtgtgagt gcaactccct taggttgtga tatgctgtgc tcgaaagtca    7200
cggagacaga ggaagaagat tataactcag ctgtccctac gctgatggta catgggaggt    7260
tagggttcga cggccaatac cacgaaaagg acctagacgt cacaacatta tttgaggact    7320
gggtggccaa ctacccagga gtaggggtg gatcttttat tgacagccgc gtatggttct    7380
cagtctacgg agggctgaaa cccaactcac ccagtgacac tgtacaggaa gagaaatatg    7440
taatatacaa gcgatacaat gacacatgcc cagatgagca agactaccag atccgaatgg    7500
ccaagtcttc gtataagccc gggcggtttg gtgggaaacg catacagcag gctatcttat    7560
ctatcaaggt gtcaacatct tgggcgaag acccagtact gactgtaccg cccaacacag    7620
tcacactcat gggggccgaa ggcagaattc tcacagtagg gacatctcat ttcttgtatc    7680
agcgagggtc atcatacttc tctcccgcgt tattatatcc tatgacagtc agcaacaaaa    7740
cagccactct tcatagtccc tatacattca atgccttcac tcggccaggt agtatcccctt   7800 gccaggcttc agcaagatgc cccaactcgt gtgttactgg agtctataca gatccatatc    7860
ccctaatctt ctataggaac cacaccttgc gaggggtatt cggacaatg cttgatggtg     7920 tacaagcaag actcaatcct gcgtctgcag tattcgacag cacatcccgc agtcgcacaa    7980
cccgagtgag ttcaagcagc accaaagcag catacacaac atcaacctgt tttaaagttg    8040
tcaagaccaa taagacctat tgtctcagca ttgctgaaat atctaatact ctctttggag    8100
aattcagaat cgtcccgtta ctagttgaga tcctcaaaaa tgatgggtt agagaagcca     8160 ggtctggtta gttgagtcaa ctatgaaaga gctggaaaga tggcattgta tcacctatct    8220
tccgcgacac caagaatcaa actgaatgcc ggtgtgagct cgaattccat gtcgccagtt    8280
gactacaatc agccagtgct catgcgatca gatcaagtct tgtcaatagt ccctcgatta    8340
agaaaaaatg taagtggcaa tgagatacaa ggcaaaacag ctcatggtaa atagtacggg    8400
taggacatgg cgagctctgg tcctgaaagg gcagagcatc agattatcct accagagtca    8460
cacctgtctt caccattggt caagcacaaa ctactttatt actggaaatt aactgggtta    8520
ccgcttcctg atgaatgtga cttcgaccac ctcattctca gcagacaatg gaaaaaaata    8580
cttgaatcgg cctctcctga tactgagaga atgataaaac tcggaagggc agtacaccaa    8640
actctcaacc acaattctag aataaccgga gtactccacc ccaggtgttt agaagaactg    8700
gctagtattg aggtccctga ttcaaccaac aaatttcgga agattgagaa gaagatccaa    8760
attcacaaca cgagatatgg agaaatgttc acaaggctgt gtacgcatat agagaagaaa    8820
ctgctggggt catcctggtc taacaatgtc ccccggtcag aggagttcaa cagcatccgt    8880
acggatccgg cattctggtt tcactcaaaa tggtccacag ccaagtttgc atggctccat    8940
ataaaacaga tccagaggca tctgattgtg gcagctagga caagggctgc ggccaacaaa    9000
ttggtgatgc taacccataa ggtaggccaa gtctttgtca ctcctgaact tgtcattgtg    9060
acgcatacga atgagaacaa gttcacatgt cttacccagg aacttgtatt gatgtatgca    9120
gatatgatgg agggcagaga tatggtcaac ataatatcaa ccacggcggt gcatctcaga    9180
agcttatcag agaaaattga tgacatttg cagttaatag acgctctggc aaaagacttg    9240
ggtaatcaag tctacgatgt tgtatcacta atggagggat ttgcatacgg agctgtccag    9300
ctgctcgagc cgtcaggtac atttgcagga gatttcttcg cattcaacct gcaggagctt    9360
aaagacattc taatcggcct cctccccaat gatatagcag aatccgtgac tcatgcaata    9420
gctactgtat tctctggttt agaacagaat caagcagctg atatgttgtg cctgttcgct    9480
ctgtggggtc acccactgct tgagtcccgt attgcagcaa aggcagtcag gagccaaacg    9540
```

```
tgcgcaccga aaatggtgga ctttgatatg atccttcagg tactgtcttt cttcaaggga   9600
acaatcatca acggatacag aaagaagaat gcaggtgtgt ggccgcgagt caaagtggat   9660
acaatatatg ggaaggtcat tgggcaacta catgcagatt cagcagagat ttcacacgat   9720
atcatgttga gagagtataa gagtttatct gcacttgaat ttgagccatg tatagaatac   9780
gaccctgtca ctaacctgag catgttccta aaagacaagg caatcgcaca ccctaacgat   9840
aattggcttg cctcgtttag gcggaacctt ctctccgaag accagaagaa acatgtaaaa   9900
gaagcaactt cgactaatcg cctcttgata gagttttttag agtcaaatga ttttgatcca   9960
tataaagaga tggaatatct gacgaccctg gagtaccttaa gagatgacga tgtggcagta  10020
tcatactcgc tcaaagagaa ggaagtgaaa gttaatggac ggatcttcgc taagctgaca  10080
aagaagttaa ggaactgtca ggtgatggcg aagggatcc tagccgacca gattgcacct  10140
ttctttcagg gaatggagt cattcaggat agcatatctt tgaccaagag tatgctagcg  10200
atgagtcaac tgtcttttaa cagcaataag aaacgtatca ctgactgtaa agaaagagta  10260
tcttcaaacc gcaatcatga tccgaagagc aagaaccgtc ggagagttgc aaccttcata  10320
acgactgacc tgcaaaagta ctgtcttaat tggagatatc agacaatcaa actgttcgct  10380
catgccatca accagttgat gggcctacct cacttcttcg agtggattca cctaagactg  10440
atggacacta caatgttcgt aggagaccct ttcaatcctc caagtgaccc tactgactgt  10500
gacctctcaa gagtccctaa tgatgacata tatattgtca gtgccagagg gggtatcgaa  10560
ggattatgtc agaagctatg gacaatgatc tctattgctg caatccaact tgctgcagct  10620
agatcgcatt gtcgcgttgc ctgtatggta cagggtgata atcaagtaat agcagtaacg  10680
agagaggtaa gatcagacga ctctccggag atggtgttga cacagttgca tcaagccagt  10740
gataatttct tcaaggaatt aattcatgtc aatcatttga ttggccataa tttgaaggat  10800
cgtgaaacca tcaggtcaga cacattcttc atatacagca aacgaatctt caaagatgga  10860
gcaatcctca gtcaagtcct caaaaattca tctaaattag tactagtatc aggtgatctc  10920
agtgaaaaca ccgtaatgtc ctgtgccaac attgcctcta ctgtagcacg gctatgcgag  10980
aacgggcttc ccaaggactt ctgttactat ttaaactata taatgagttg cgtgcagaca  11040
tactttgact ctgagttctc catcaccaac aattcgcacc ccgatcttaa ccagtcgtgg  11100
attgaggaca tctcttttgt gcactcatat gttctgactc ctgcccaatt aggggactt   11160
agtaaccttc aatactcaag gctctacact agaaatatcg gtgacccggg gactactgct  11220
tttgcagaga tcaagcgact agaagcagtg ggattactga gtcctaacat tatgactaat  11280
atcttaacta ggccgcctgg gaatggagat tgggccagtc tttgcaacga cccatactct  11340
ttcaattttg agactgttgc aagcccaaac attgttctta agaaacatac gcaaagagtc  11400
ctatttgaaa cttgttcaaa tccttattg tctggagtgc acacagagga taatgaggca  11460
gaagagaagg cattggctga attcttgctt aatcaagagg tgattcatcc ccgcgttgcg  11520
catgctatca tggaggcaag ctctgtaggt aggagaaagc aaattcaagg cttgttgac   11580
acaacaaaca ccgtaattaa gattgcactt actaggaggc cactaggcat caagaggctg  11640
atgcggatag tcaattattc tagcatgcat gcaatgctgt ttagagacga tgttttttcc  11700
tccaatcgat ccaaccaccc cttagtctct ctaatatgt gttctctgac actggcagac  11760
tatgcacgga atagaagctg gtcacctttg acgggaggca ggaaaatact gggtgtatct  11820
aatcctgata cgatagaact cgtagagggt gagattctta gtgtaagcgg agggtgcaca  11880
```

```
agatgtgaca gcggagatga acagtttact tggttccatc ttccaagcaa tatagaattg   11940
accgatgaca ccagcaagaa tcctccgatg agagtaccat atctcgggtc aaagacacag   12000
gagaggagag ctgcctcact tgcgaaaata gctcatatgt cgccacatgt gaaggctgcc   12060
ctaagggcat catccgtgtt gatctgggct tatggggata atgaagtaaa ttggactgct   12120
gctcttacga ttgcaaaatc tcggtgtaat ataaacttag agtatcttcg gttattgtcc   12180
cctttaccca cggctgggaa tcttcaacat agactagatg acggtataac tcagatgaca   12240
ttcacccctg catctctcta cagggtgtca ccttacattc acatatccaa tgattctcaa   12300
aggctattca ctgaagaagg agtcaaagag gggaatgtgg tttatcaaca gatcatgctc   12360
ttgggtttat ctctaatcga atcgatcttt ccaatgatga caaccaggac atatgatgag   12420
atcacattgc atctacatag taaatttagt tgctgtatca gggaagcacc tgttgcggtt   12480
cctttcgagc tacttggggt ggcaccggag ctaaggacag tgacctcaaa taagtttatg   12540
tatgatccta gccctgtatc ggagggagac tttgcgagac ttgacttagc tatcttcaag   12600
agttatgagc ttaatctgga gtcatatccc acgatagagc taatgaacat tctttcaata   12660
tccagcggga agttgattgg ccagtctgtg gtttcttatg atgaagatac ctccataaag   12720
aatgacgcca taatagtgta tgacaatacc cgaaattgga tcagtgaagc tcagaattca   12780
gatgtggtcc gcttatttga atatgcagca cttgaagtgc tcctcgactg ttcttaccaa   12840
ctctattatc tgagagtaag aggcctagac aatattgtct tatatatggg tgatttatac   12900
aagaatatgc caggaattct actttccaac attgcagcca caatatctca tcccgtcatt   12960
cattcaaggt tacatgcagt gggcctggtc aaccatgacg gatcacacca acttgcagat   13020
acggatttta tcgaaatgtc tgcaaaactg ttagtatctt gcactcgacg tgtgatctcc   13080
ggcttatatt cagggaataa gtatgatctg ctgttcccat ctgtcttaga tgataacctg   13140
aatgagaaga tgcttcagct gatatcccgg ttatgctgtc tgtacacggt actctttgct   13200
acaacaagag aaatcccgaa aataagaggc ttatctgcag aagagaaatg ttcagtactt   13260
actgagtatc tactgtcgga tgctgtgaaa ccattactta gccctgatca ggtgagctct   13320
atcatgtctc ctaacataat tacattccca gctaatctgt actacatgtc tcggaagagc   13380
ctcaatttga tcagggaaag ggaggacagg gatactatcc tggcgttgtt gttcccccaa   13440
gagccattat tagagttccc ttctgtgcaa gatattggtg ctcgagtgaa agatccattc   13500
acccgacaac ctgcggcatt tttgcaagag ttagatttga gtgctccagc aaggtatgac   13560
gcattcacac ttagtcagat tcatcctgag ctcacatcac caaatccgga ggaagactac   13620
ttagtacgat acttgttcag aggaataggg gctgcatcct cctcttggta taaggcatcc   13680
catctccttt ctgtacccga ggtaagatgt gcaagacacg ggaactcctt atacttagct   13740
gaaggaagcg gagccatcat gagtcttctc gaactgcata taccacatga aactatctat   13800
tacaatacgc tctttcaaa tgagatgaac ccccgcagc gacatttcgg gccgacccca   13860
acccagtttt tgaattcggt tgtttatagg aacctacagg cggaggtaac atgcaaggat   13920
ggatttgtcc aagagttccg tccactatgg agagaaaata cagaggaaag cgacctgacc   13980
tcagataaag cagtggggta tattacatct gcagtgccct acagatctgt atcattgctg   14040
cattgtgaca ttgaaatccc tccagggtcc aatcaaagct tactagatca actagctatc   14100
aatttatctc tgattgccat gcattcctta agggagggcg gggtagtgat catcaaagtg   14160
ttgtatgcaa tgggatacta cttttcatcta ctcatgaact tgttcgctcc gtgttccaca   14220
aaaggataca ttctctctaa tggttatgca tgtagagggg atatggagtg ttacctggta   14280
```

```
tttgtcatgg gttacctggg cgggcctaca tttgtacacg aggtggtgag gatggcaaaa   14340
actctggtgc agcggcacgg tacgcttttg tccaaatcag atgagatcac actgaccagg   14400
ttattcacct cacagcggca gcgtgtgaca gacatcctat ccagtccttt accaagatta   14460
ataaagtact tgagaaagaa tattgacact gcgctgattg aagctggggg acagcccgtc   14520
cgtccattct gtgcagagag tttggtgagc acgctagcgg acataactca gataacccag   14580
atcattgcta gtcacattga cacagtcatc cggtctgtga tatatatgga agctgagggt   14640
gatctcgctg acacagtttt tctatttacc ccttacaatc tctctactga cgggaaaaag   14700
agaacatcac ttaaacagtg cacgagacag atcctagagg ttacaatact gggtcttaga   14760
gtcgaagatc tcaataaaat aggcgatgta atcagcctag tgcttaaagg catgatctcc   14820
atggaggacc ttatcccact aaggacatac ttgaagcata gtacctgccc taaatatttg   14880
aaggctgtcc taggtattac caaacttaaa gaaatgttta cagacacctc tgtattgtac   14940
ttgactcgtg ctcaacaaaa attctacatg aaaactatag gcaatgcagt caaaggatat   15000
tacagtaact gtgactctta acgaaaatca catattaata ggctcttttt ctggccaatt   15060
gtatccttgg tgatttaatt atactatgtt agaaaaaagt tgaactctga ctccttagag   15120
ctcgaattcg aactcaaata aatgtcttaa aaaaaggttg cgcacaattt ttcttgagtg   15180
tagtcttgtc attcaccaaa tctttgtttg gtggccggca tggtcccagc ctcctcgctg   15240
gcgccggctg ggcaacattc cgaggggacc gtcccctcgg taatggcgaa tgggacgtcg   15300
acagctaaca aagcccgaag gaagtgagtt gctgctgcca ccgttgagca ataactagca   15360
taacccctgg gggcctctaa acgggtcttg agggtttttt tgctgaaagg agtcgtggag   15420
acgttgttta aactacgtat aatacgactc actataggga ccaaacagag aatccgtagg   15480
ttacgataaa aggcgaagga gcaattgaag ttggacgggt agaaggtgtg aatctcgagt   15540
gcgagcccga agcacaaact cgagaaagcc ttctgccaac atgtcttccg tatttgacga   15600
gtacgaacag ctcctcgcgt ctcagactcg ccccaatgga gctcatggag gagggggaaaa   15660 ggggagtacc ttaaaagtag acgtcccggt attcactctt aacagtgatg acccagaaga   15720
taggtggaac tttgcggtat tctgcctccg gattgctgtt agcgaagatg ccaacaaacc   15780
actcaggcaa ggtgctctca tatctctttt atgctcccac tcacaagtga tgaggaacca   15840
tgttgccctt gcagggaaac agaatgaagc cacattggcc gtgcttgaga ttgatggctt   15900
tgccaacggt atgccccagt tcaacaatag gagtggagtg tctgaagaga gagcacagag   15960
attgcgatat atagcagggt ctctccctcg ggcatgcagt aatggcaccc cgttcgtcac   16020
agccggggcc gaagatgatg caccagaaga catcaccgat accctggaga ggatcctctc   16080
tatccaggcc caagtatggg tcacagtagc aaaagccatg actgcgtatg agactgcaga   16140
tgagtcagaa acaagacgaa tcaataagta tatgcagcaa ggcagggtcc aaaagaaata   16200
catcctctac cccgtatgca ggagcacaat ccaactcacg atcagacagt ctcttgcagt   16260
ccgcatcttt ttggttagcg agctcaagag aggccgcaac acggcaggtg gtacctctac   16320
ttattataac ctagtagggg acgtagactc atatatcagg aataccgggc ttactgcatt   16380
cttcctgaca ctcaagtacg gaatcaacac caagacatca gcccttgcac ttagtagcct   16440
ctcaggcgac atccagaaga tgaagcagct catgcgtttg tatcggatga aggagataa   16500 tgcgccgtac atgacattgc ttggtgatag tgaccagatg agctttgcgc ctgccgagta   16560
tgcacaactt tactccttcg ccatgggtat ggcatcagtc ctagataaag gtaccgggaa   16620
```

```
ataccaattt gccagggact ttatgagcac atcattctgg agacttggag tagagtacgc    16680
tcaggctcag ggaagtagca ttaacgagga tatggctgcc gagctaaagc taacccccagc   16740
agcaaggaga ggcctggcag ctgctgccca acgagtctcc gaggagacca gcagcataga    16800
catgcctact caacaagtcg gagtcctcac tgggctcagc gagggggggt cccaagccct    16860
acaaggcgga tcgaatagat cgcaagggca accagaagcc ggggatgggg agacccaatt    16920
cctggatctg atgagagcgg tagcaaatag catgagggaa gcgccaaact ctgcacaggg    16980
cactccccaa tcggggcctc ccccaactcc tgggccatcc aagataacg acaccgactg     17040
ggggtattga ttgacaaaac ccagcttgct tccacaaaat catcccaata ccctcacccg    17100
tagtcgaccc ctcgatttgc ggccctacat gaccacaccc tcaaacaaac atcccctct    17160
ttcctccctc cccctgctgt acaactccgc acgccctagg taccacaggc acaatgcggc    17220
tcactaacaa tcaaaacaga gccgaggaaa ttagaaaaaa gtacgggtag aagagggata    17280
ttcagagacc agggcaagtc tcccgagtct ctgctctctc ctctacctga tagattagga    17340
caaatatggc cacctttaca gatgcggaga tcgacgagct atttgagaca agtggaactg    17400
tcattgacaa cataattaca gcccagggta aaccagcaga gactgtggga aggagtgcaa    17460
tcccacatgg caaaaccaag gcgctgagcg cagcatggga gaagcatggg agcatccagc    17520
caccagccag tcaagacacc cctgatcgac aggacagatc tgacaaacaa ccatccacac    17580
ccgagcaagc gaccccgcat gacagcccgc cggccacatc cgccgaccag ccccccaccc    17640
aggccacaga cgaagccgtc gacacacagc tcaggaccgg agcaagcaac tctctgctgt    17700
tgatgcttga caagctcagc aataaatcat ccaatgctaa aaagggccca tggtcgagcc    17760
cccaagaggg gaaccaccaa cgtccgactc aacagcaggg aagtcaaccc agccgcggaa    17820
acagtcagga aagaccacag aaccaagtca aggccgcccc tggaaaccag ggcacagacg    17880
cgaacacagc atatcatgga caatgggagg agtcacaact atcagctggt gcaaccctc     17940
atgctctccg atcaaggcag agccaagaca ataccttgt atctgcggat catgtccagc     18000
cacctgtaga cttgtgcaa gcgatgatgt ctatgatgga ggcaatatca cagagagtaa     18060
gtaaggttga ctatcagcta gatcttgtct tgaaacagac atcctccatc cctatgatgc    18120
ggtccgaaat ccaacagctg aaaacatctg ttgcagtcat ggaagccaat ttgggaatga    18180
tgaagattct ggatcccggt tgtgccaacg tttcatctct gagtgatcta cgggcagttg    18240
cccgatctca cccggtttta gtttcaggcc ctggagaccc atctccctat gtgactcaag    18300
gaggcgaaat ggcacttaat aaactttcgc aaccagtgcc acatccatct gaattgatta    18360
aacccgccac tgcatgcggg cctgatatag gagtggaaaa ggacactgtc cgtgcattga    18420
tcatgtcacg cccaatgcac ccgagttctt cagccaagct cctaagcaag ctagatgcag    18480
ccgggtcgat cgaggaaatc aggaaaatca agcgccttgc actaaatggc taattaccac    18540
tgccacacgt agcgggtccc cgtccactcg gcatcacacg gaatctgcac cgagtccccc    18600
cccgcagacc taaggtccaa ctctccaagt ggcaatcctc tctcgcttcc tcagcccac    18660
tgaatgatcg cgcaaccgta attaatctag ctacattaag gattaagaaa aaatacgggt    18720
agaattggaa tgccccaatt gtgccaagat ggactcatct aggacaattg gctgtactt    18780
tgattctgcc cattcttcta gcaacctgtt agcatttccg atcgtcctac aagacacagg    18840
agatgggaag aagcaaatcg ccccgcaata taggatccag cgccttgact cgtggactga    18900
tagtaaagaa gactcagtat tcatcaccac ctatggattc atctttcagg ttgggaatga    18960
agaagccact gtcggcatga tcaatgataa tcccaagcgc gagttacttt ccgctgcgat    19020
```

```
gctctgccta ggaagcgtcc caaataccgg agaccttgtt gagctggcaa gggcctgtct   19080
cactatggta gtcacatgca agaagagtgc aactaatact gagagaatgg ttttctcagt   19140
agtgcaggca ccccgagtgc tgcaaagctg tagggctgtg gcagacaaat actcatcagc   19200
gaatgcagtc aagcacgtga aagcgccaga gaagatcccc gggagtggaa ccctagaata   19260
caaggtgaac tttgtctcct tgactgtggt accgaagaag gatgtctaca agatcccaac   19320
tgcagtattg aaggtttctg gctcgagtct gtacaatctt gcgctcaatg tcactattaa   19380
tgtggaggta gacccgagga gtcctttggt taaatctctg tctaagtctg acagcggata   19440
ctatgctgac ctcttcttgc atattggact tatgaccacc gtagatagga agggaagaa    19500
agtgactttt gacaagctag aaaagaagat aaggagactt gatctatctg tcgggctcag   19560
tgatgtgctc ggaccttccg tgctggtaaa agcaagaggt gcacggacca gcttttggc    19620
acctttcttc tctagcagtg ggacagcctg ctatcccata gcaaatgcct ctccccaggt   19680
ggccaagata ctctggagtc aaaccgcgtg cctgcggagc gttaaaatca ttatccaagc   19740
aggtacccaa cgcgctgtcg cagtgaccgc tgaccacgag gttacctcta ctaagctgga   19800
gaaggggcac acccttgcca aatacaatcc ttttaagaaa taagctgcgt ttctgagatt   19860
gcgctccgcc cactcaccca gagcatcatg acaccaaaaa ctaatctgtc ttgattattt   19920
acagttagtt tacctgtcta tcaaattaga aaaaacacgg gtagaagatt ctggatcccg   19980
gttggcgcct tctaggtgca agatgggccc cagaccttct accaagaacc cagcacctat   20040
gatgctgact gtccgggtcg cgctggtact gagttgcatc tgtccggcaa actccattga   20100
tggcaggcct cttgcggctg caggaattgt ggtaacagga gacaaagcag tcaacatata   20160
cacctcatcc cagacaggat caatcatagt taagctcctc ccaaacctgc ccaaggataa   20220
ggaggcatgt gcgaaagccc ccttggatgc atacaacagg acattgacca ctttgctcac   20280
ccccctgggt gactctatcc gtaggataca agagtctgta actacatctg gagggaggag   20340
acagaaacgc tttataggcg ccattattgg cggtgtggct cttggagttg caactgctgc   20400
acaaataaca gcggccgcag ctctgataca agccaaacaa aatgctgcca acatcctccg   20460
acttaaagag agcattgccg caaccaatga ggccgtgcat gaggtcactg acggattatc   20520
gcaactagca gtggcagttg ggaagatgca gcagtttgtc aatgaccaat ttaataaaac   20580
aactcaggaa ttaggctgca tcagaattgc acagcaagtt ggcgtagagc tcaacctgta   20640
tctaaccgaa ttgactacag tattcggacc acaaatcact tcacctgcct taaacaagct   20700
gactattcag gcactttaca atctagctgg tgggaatatg gatcacttgt tgactaagtt   20760
aggtgtaggg aacaatcaac tcagctcatt aatcggtagc ggcttaatca ccggcaaccc   20820
tattctgtac gactcacaga ctcaactctt gggtatacag gtaactctac cttcagtcgg   20880
gaacctaaat aatatgcgtg ccacctactt ggaaaaccttа tccgtaagca caaccagggg   20940
atttgcctcg gcacttgtcc caaaagtggt gacacaggtc ggttctgtga tagaagaact   21000
tgacacctca tattgtatag aaaccgactt ggatttatat tgtacaagaa tagtaacatt   21060
ccctatgtcc cctggtattt attcctgctt gagcggcaat acatcggcct gtatgtactc   21120
aaagaccgaa ggcgcactca ctacgccata catgactatc aaaggctcag tcatcgctaa   21180
ctgcaagatg acaacatgta gatgtgtaaa ccccccgggt atcatatcgc aaaactatgg   21240
ggaagccgtg tctctaatag ataagcaatc atgcaatgtt ttatccttag acgggataac   21300
tttaaggctc agtgggggaat tcgatgcaac ttatcagaag aatatctcaa tacaagattc   21360
```

```
tcaagtaata ataacaggca atcttgatat ctcaactgag cttgggaatg tcaacaactc   21420
gatcagtaat gctttgaata agttagagga aagcaacagc aaactagaca aagtcaatgt   21480
caaactgacc agcacatctg ctctcattac ctatatcgtt ttgactatca tatctcttgt   21540
ttttggtata cttagcctgg ttctagcatg ctacctaatg tacaagcaaa aggcgcaaca   21600
aaagacctta ttatggcttg ggaataatac cctagatcag atgagagcca ctacaaaaat   21660
gtgaacacag atgaggaacg aaggtatccc taatagtaat ttgtgtgaaa gttctggtag   21720
tctgtcagtt cggagagttt agaaaaaact accggttgta gatgaccaaa ggacgatata   21780
cgggtagaac ggtaagagag gccgcccctc aattgcgagc cgggcttcac aacctccgtt   21840
ctaccgcttc accgacagca gtcctcagtc atggaccgcg cagttagcca agttgcgtta   21900
gagaatgatg aaagagaggc aaaaaataca tggcgcttga tattccggat tgcaatctta   21960
ctcttaacag tagtgacctt agctacatct gtagcctccc ttgtatatag catgggggct   22020
agcacaccta gcgaccttgt aggcataccg accaggattt ccagggcaga agaaaaaatt   22080
acatctgcac ttggttccaa tcaagatgta gtagatagga tatataagca agtggccctt   22140
gagtctccgt tggcattgtt aaacactgag atcacaatta tgaacgcaat aacatctctc   22200
tcttatcaga ttaatggagc tgcgaacaac agcggtgggg gggcacctat ccatgaccca   22260
gattttatcg ggggatagg caaagaactc attgtagatg atgctagtga tgtcacatca   22320
ttctatccct ctgcatttca agaacatctg aattttatcc cggcgcctac tacaggatca   22380
ggttgcactc ggttaccttc atttgacatg agtgctaccc attactgcta cactcataat   22440
gtaatattgt ctggatgcag agatcactca cactcacatc agtatttagc acttggtgtg   22500
ctccggacat ctgcaacagg gaggatattc ttttctactc tgcgttccat caatctggat   22560
gacacccaaa atcggaagtc ttgcagtgtg agtgcaactc ccttaggttg tgatatgctg   22620
tgctcgaaag tcacggagac agaggaagaa gattataact cagctgtccc tacgctgatg   22680
gtacatggga ggttagggtt cgacggccaa taccacgaaa aggacctaga cgtcacaaca   22740
ttatttgagg actgggtggc caactaccca ggagtagggg gtggatcttt tattgacagc   22800
cgcgtatggt tctcagtcta cggagggctg aaacccaact cacccagtga cactgtacag   22860
gaagagaaat atgtaatata caagcgatac aatgacacat gcccagatga gcaagactac   22920
cagatccgaa tggccaagtc ttcgtataag cccgggcggt ttggtgggaa acgcatacag   22980
caggctatct tatctatcaa ggtgtcaaca tctttgggcg aagacccagt actgactgta   23040
ccgcccaaca cagtcacact catgggggcc gaaggcagaa ttctcacagt agggacatct   23100
catttcttgt atcagcgagg gtcatcatac ttctctcccg cgttattata tcctatgaca   23160
gtcagcaaca aaacagccac tcttcatagt ccctatacat tcaatgcctt cactcggcca   23220
ggtagtatcc cttgccaggc ttcagcaaga tgccccaact cgtgtgttac tggagtctat   23280
acagatccat atcccctaat cttctatagg aaccacacct tgcgaggggt attcgggaca   23340
atgcttgatg gtgtgtacaa gc aagactcaat cctgcgtctg cagtattcga cagcacatcc   23400
cgcagtcgca aacccgagt gagttcaagc agcaccaaag cagcatacac aacatcaacc   23460
tgttttaaag ttgtcaagac caataagacc tattgtctca gcattgctga atatctaat   23520 actctctttg gagaattcag aatcgtcccg ttactagttg agatcctcaa aaatgatggg   23580
gttagagaag ccaggtctgg ttagttgagt caactatgaa agagctggaa agatggcatt   23640
gtatcaccta tcttccgcga caccaagaat caaaactgaat gccggtgtga gctcgaattc   23700
catgtcgcca gttgactaca atcagccagt gctcatgcga tcagatcaag tcttgtcaat   23760
```

```
agtccctcga ttaagaaaaa atgtaagtgg caatgagata caaggcaaaa cagctcatgg   23820
taaatagtac gggtaggaca tggcgagctc tggtcctgaa agggcagagc atcagattat   23880
cctaccagag tcacacctgt cttcaccatt ggtcaagcac aaactacttt attactggaa   23940
attaactggg ttaccgcttc ctgatgaatg tgacttcgac cacctcattc tcagcagaca   24000
atggaaaaaa atacttgaat cggcctctcc tgatactgag agaatgataa aactcggaag   24060
ggcagtacac caaactctca accacaattc tagaataacc ggagtactcc accccaggtg   24120
tttagaagaa ctggctagta ttgaggtccc tgattcaacc aacaaatttc ggaagattga   24180
gaagaagatc caaattcaca acacgagata tggagaaatg ttcacaaggc tgtgtacgca   24240
tatagagaag aaactgctgg ggtcatcctg gtctaacaat gtcccccggt cagaggagtt   24300
caacagcatc cgtacggatc cggcattctg gtttcactca aaatggtcca cagccaagtt   24360
tgcatggctc catataaaac agatccagag gcatctgatt gtggcagcta ggacaagggc   24420
tgcggccaac aaattggtga tgctaaccca taaggtaggc caagtctttg tcactcctga   24480
acttgtcatt gtgacgcata cgaatgagaa caagttcaca tgtcttaccc aggaacttgt   24540
attgatgtat gcagatatga tggagggcag agatatggtc aacataatat caaccacggc   24600
ggtgcatctc agaagcttat cagagaaaat tgatgacatt ttgcagttaa tagacgctct   24660
ggcaaaagac ttgggtaatc aagtctacga tgttgtatca ctaatggagg gatttgcata   24720
cggagctgtc cagctgctcg agccgtcagg tacatttgca ggagatttct tcgcattcaa   24780
cctgcaggag cttaaagaca ttctaatcgg cctcctcccc aatgatatag cagaatccgt   24840
gactcatgca atagctactg tattctctgg tttagaacag aatcaagcag ctgagatgtt   24900
gtgcctgttg cgtctgtggg gtcacccact gcttgagtcc cgtattgcag caaaggcagt   24960
caggagccaa acgtgcgcac cgaaaatggt ggactttgat atgatccttc aggtactgtc   25020
tttcttcaag ggaacaatca tcaacggata cagaaagaag aatgcaggtg tgtggccgcg   25080
agtcaaagtg gatacaatat atgggaaggt cattgggcaa ctacatgcag attcagcaga   25140
gatttcacac gatatcatgt tgagagagta taagagttta tctgcacttg aatttgagcc   25200
atgtatagaa tacgaccctg tcactaacct gagcatgttc ctaaaagaca aggcaatcgc   25260 acacccctaac gataattggc ttgcctcgtt taggcggaac cttctctccg aagaccagaa   25320
gaaacatgta aaagaagcaa cttcgactaa tcgcctcttg atagagtttt tagagtcaaa   25380
tgattttgat ccatataaag agatggaata tctgacgacc ctggagtacc ttagagatga   25440
cgatgtggca gtatcatact cgctcaaaga gaaggaagtg aaagttaatg gacggatctt   25500
cgctaagctg acaaagaagt taaggaactg tcaggtgatg gcggaaggga tcctagccga   25560
ccagattgca ccttttctttc agggaaatgg agtcattcag gatagcatat ctttgaccaa   25620
gagtatgcta gcgatgagtc aactgtcttt taacagcaat aagaaacgta tcactgactg   25680
taaagaaaga gtatcttcaa accgcaatca tgatccgaag agcaagaacc gtcggagagt   25740
tgcaaccttc ataacgactg acctgcaaaa gtactgtctt aattggagat atcagacaat   25800
caaactgttc gctcatgcca tcaaccagtt gatgggccta cctcacttct tcgagtggat   25860
tcacctaaga ctgatggaca ctacaatgtt cgtaggagac cctttcaatc ctccaagtga   25920
ccctactgac tgtgacctct caagagtccc taatgatgac atatatattg tcagtgccag   25980
agggggtatc gaaggattat gtcagaagct atggacaatg atctctattg ctgcaatcca   26040
acttgctgca gctagatcgc attgtcgcgt tgcctgtatg gtacagggtg ataatcaagt   26100
```

```
aatagcagta acgagagagg taagatcaga cgactctccg gagatggtgt tgacacagtt    26160
gcatcaagcc agtgataatt tcttcaagga attaattcat gtcaatcatt tgattggcca    26220
taatttgaag gatcgtgaaa ccatcaggtc agacacattc ttcatataca gcaaacgaat    26280
cttcaaagat ggagcaatcc tcagtcaagt cctcaaaaat tcatctaaat tagtactagt    26340
atcaggtgat ctcagtgaaa acaccgtaat gtcctgtgcc aacattgcct ctactgtagc    26400
acggctatgc gagaacgggc ttcccaagga cttctgttac tatttaaact atataatgag    26460
ttgcgtgcag acatactttg actctgagtt ctccatcacc aacaattcgc ccccgatct     26520
taaccagtcg tggattgagg acatctcttt tgtgcactca tatgttctga ctcctgccca    26580
attaggggga cttagtaacc ttcaatactc aaggctctac actagaaata tcggtgaccc    26640
ggggactact gcttttgcag agatcaagcg actagaagca gtgggattac tgagtcctaa    26700
cattatgact aatatcttaa ctaggccgcc tgggaatgga gattgggcca gtctttgcaa    26760
cgacccatac tctttcaatt ttgagactgt tgcaagccca acattgttc ttaagaaaca     26820
tacgcaaaga gtcctatttg aaacttgttc aaatccctta ttgtctggag tgcacacaga    26880
ggataatgag gcagaagaga aggcattggc tgaattcttg cttaatcaag aggtgattca    26940
tccccgcgtt gcgcatgcta tcatggaggc aagctctgta ggtaggagaa agcaaattca    27000
agggcttgtt gacacaacaa acaccgtaat taagattgca cttactagga ggccactagg    27060
catcaagagg ctgatgcgga tagtcaatta ttctagcatg catgcaatgc tgtttagaga    27120
cgatgttttt tcctccaatc gatccaacca cccctagtc tcttctaata tgtgttctct      27180
gacactggca gactatgcac ggaatagaag ctggtcacct ttgacgggag gcaggaaaat    27240
actgggtgta tctaatcctg atacgataga actcgtagag ggtgagattc ttagtgtaag    27300
cggagggtgc acaagatgtg acagcggaga tgaacagttt acttggttcc atcttccaag    27360
caatatagaa ttgaccgatg acaccagcaa gaatcctccg atgagagtac catatctcgg    27420
gtcaaagaca caggagagga gagctgcctc acttgcgaaa atagctcata tgtcgccaca    27480
tgtgaaggct gccctaaggg catcatccgt gttgatctgg gcttatgggg ataatgaagt    27540
aaattggact gctgctctta cgattgcaaa atctcggtgt aatataaact tagagtatct    27600
tcggttattg tccccctttac ccacggctgg gaatcttcaa catagactag atgacggtat    27660
aactcagatg acattcaccc ctgcatctct ctacagggtg tcaccttaca ttcacatatc    27720
caatgattct caaaggctat tcactgaaga aggagtcaaa gaggggaatg tggtttatca    27780
acagatcatg ctcttgggtt tatctctaat cgaatcgatc tttccaatga tgacaaccag    27840
gacatatgat gagatcacat tgcatctaca tagtaaattt agttgctgta tcagggaagc    27900
acctgttgcg gttcctttcg agctacttgg ggtggcaccg gagctaagga cagtgacctc    27960
aaataagttt atgtatgatc ctagccctgt atcggaggga gactttgcga gacttgactt    28020
agctatcttc aagagttatg agcttaatct ggagtcatat cccacgatag agctaatgaa    28080
cattctttca atatccagcg ggaagttgat tggccagtct gtggtttctt atgatgaaga    28140
tacctccata aagaatgacg ccataatagt gtatgacaat acccgaaatt ggatcagtga    28200
agctcagaat tcagatgtgg tccgcttatt tgaatatgca gcacttgaag tgctcctcga    28260
ctgttcttac caactctatt atctgagagt aagaggccta gacaatattg tcttatatat    28320
gggtgattta tacaagaata tgccaggaat tctactttcc aacattgcag ccacaatatc    28380
tcatcccgtc attcattcaa ggttacatgc agtgggcctg gtcaaccatg acggatcaca    28440
ccaacttgca gatacggatt ttatcgaaat gtctgcaaaa ctgttagtat cttgcactcg    28500
```

```
acgtgtgatc tccggcttat attcagggaa taagtatgat ctgctgttcc catctgtctt   28560
agatgataac ctgaatgaga agatgcttca gctgatatcc cggttatgct gtctgtacac   28620
ggtactcttt gctacaacaa gagaaatccc gaaaataaga ggcttatctg cagaagagaa   28680
atgttcagta cttactgagt atctactgtc ggatgctgtg aaaccattac ttagccctga   28740
tcaggtgagc tctatcatgt ctcctaacat aattacattc ccagctaatc tgtactacat   28800
gtctcggaag agcctcaatt tgatcaggga aagggaggac agggatacta tcctggcgtt   28860
gttgttcccc caagagccat tattagagtt cccttctgtg caagatattg gtgctcgagt   28920
gaaagatcca ttcacccgac aacctgcggc atttttgcaa gagttagatt tgagtgctcc   28980
agcaaggtat gacgcattca cacttagtca gattcatcct gagctcacat caccaaatcc   29040
ggaggaagac tacttagtac gatacttgtt cagaggaata ggggctgcat cctcctcttg   29100
gtataaggca tcccatctcc tttctgtacc cgaggtaaga tgtgcaagac acgggaactc   29160
cttatactta gctgaaggaa gcggagccat catgagtctt ctcgaactgc atataccaca   29220
tgaaactatc tattacaata cgctcttttc aaatgagatg aaccccccgc agcgacattt   29280
cgggccgacc ccaacccagt ttttgaattc ggttgtttat aggaacctac aggcggaggt   29340
aacatgcaag gatggatttg tccaagagtt ccgtccacta tggagagaaa atacagagga   29400
aagcgacctg acctcagata aagcagtggg gtatattaca tctgcagtgc cctacagatc   29460
tgtatcattg ctgcattgtg acattgaaat ccctccaggg tccaatcaaa gcttactaga   29520
tcaactagct atcaatttat ctctgattgc catgcattcc ttaagggagg gcggggtagt   29580
gatcatcaaa gtgttgtatg caatgggata ctactttcat ctactcatga acttgttcgc   29640
tccgtgttcc acaaaaggat acattctctc taatggttat gcatgtagag gggatatgga   29700
gtgttacctg gtatttgtca tgggttacct gggcgggcct acatttgtac acgaggtggt   29760
gaggatggca aaaactctgg tgcagcggca cggtacgctt ttgtccaaat cagatgagat   29820
cacactgacc aggttattca cctcacagcg gcagcgtgtg acagacatcc tatccagtcc   29880
tttaccaaga ttaataaagt acttgagaaa gaatattgac actgcgctga ttgaagctgg   29940
gggacagccc gtccgtccat tctgtgcaga gagtttggtg agcacgctag cggacataac   30000
tcagataacc cagatcattg ctagtcacat tgacacagtc atccggtctg tgatatatat   30060
ggaagctgag ggtgatctcg ctgacacagt ttttctattt accccttaca atctctctac   30120
tgacgggaaa aagagaacat cacttaaaca gtgcacgaga cagatcctag aggttacaat   30180
actgggtctt agagtcgaag atctcaataa aataggcgat gtaatcagcc tagtgcttaa   30240
aggcatgatc tccatggagg accttatccc actaaggaca tacttgaagc atagtacctg   30300 ccctaaaatat ttgaaggctg tcctaggtat taccaaactt aaagaaatgt ttacagacac   30360
ctctgtattg tacttgactc gtgctcaaca aaaattctac atgaaaacta taggcaatgc   30420
agtcaaagga tattacagta actgtgactc ttaacgaaaa tcacatatta ataggctctt   30480
tttctggcca attgtatcct tggtgattta attatactat gttagaaaaa agttgaactc   30540
tgactcctta gagctcgaat tcgaactcaa ataaatgtct taaaaaaagg ttgcgcacaa   30600
tttttcttga gtgtagtctt gtcattcacc aaatctttgt ttggtggccg gcatggtccc   30660
agcctcctcg ctggcgccgg ctgggcaaca ttccgagggg accgtcccct cggtaatggc   30720
gaatgggacg tcgacagcta acaaagcccg aaggaagtga gttgctgctg ccaccgttga   30780
gcaataacta gcataacccc ttggggcctc taaacgggtc ttgagggggtt ttttgctgaa   30840
```

```
aggagtcgtg gagacgttgt ttaaac                                          30866
```

<210> SEQ ID NO 7
<211> LENGTH: 1662
<212> TYPE: DNA
<213> ORGANISM: Newcastle disease virus

<400> SEQUENCE: 7

```
atgggcccca gaccttctac caagaaccca gcacctatga tgctgactgt ccgggtcgcg     60
ctggtactga gttgcatctg tccggcaaac tccattgatg caggcctct tgcggctgca    120
ggaattgtgg taacaggaga caaagcagtc aacatataca cctcatccca gacaggatca    180
atcatagtta agctcctccc aaacctgccc aaggataagg aggcatgtgc gaaagccccc    240
ttggatgcat acaacaggac attgaccact ttgctcaccc cccttggtga ctctatccgt    300
aggatacaag agtctgtaac tacatctgga gggaggagac agaaacgctt tataggcgcc    360
attattggcg gtgtggctct tggagttgca actgctgcac aaataacagc ggccgcagct    420
ctgatacaag ccaaacaaaa tgctgccaac atcctccgac ttaaagagag cattgccgca    480
accaatgagg ccgtgcatga ggtcactgac ggattatcgc aactagcagt ggcagttggg    540
aagatgcagc agtttgtcaa tgaccaattt aataaaacaa ctcaggaatt aggctgcatc    600
agaattgcac agcaagttgg cgtagagctc aacctgtatc taaccgaatt gactacagta    660
ttcggaccac aaatcacttc acctgcctta acaagctga ctattcaggc actttacaat    720
ctagctggtg ggaatatgga tcacttgttg actaagttag gtgtagggaa caatcaactc    780
agctcattaa tcggtagcgg cttaatcacc ggcaaccta ttctgtacga ctcacagact    840
caactcttgg gtatacaggt aactctacct tcagtcggga acctaaataa tatgcgtgcc    900
acctacttgg aaaccttatc cgtaagcaca accaggggga ttgcctcggc acttgtccca    960
aaagtggtga cacaggtcgg ttctgtgata gaagaacttg acacctcata ttgtatagaa   1020
accgacttgg atttatattg tacaagaata gtaacattcc ctatgtcccc tggtatttat   1080
tcctgcttga gcggcaatac atcggcctgt atgtactcaa agaccgaagg cgcactcact   1140
acgccataca tgactatcaa aggctcagtc atcgctaact gcaagatgac aacatgtaga   1200
tgtgtaaacc ccccgggtat catatcgcaa aactatgggg aagccgtgtc tctaatagat   1260
aagcaatcat gcaatgtttt atccttagac gggataactt taaggctcag tggggaattc   1320
gatgcaactt atcagaagaa tatctcaata caagattctc aagtaataat aacaggcaat   1380
cttgatatct caactgagct tgggaatgtc aacaactcga tcagtaatgc tttgaataag   1440
ttagaggaaa gcaacagcaa actagacaaa gtcaatgtca aactgaccag cacatctgct   1500
ctcattacct atatcgtttt gactatcata tctcttgttt ttggtatact tagcctggtt   1560
ctagcatgct acctaatgta caagcaaaag gcgcaacaaa agaccttatt atggcttggg   1620
aataataccc tagatcagat gagagccact acaaaaatgt ga                      1662
```

<210> SEQ ID NO 8
<211> LENGTH: 553
<212> TYPE: PRT
<213> ORGANISM: Newcastle disease virus

<400> SEQUENCE: 8

```
Met Gly Pro Arg Pro Ser Thr Lys Asn Pro Ala Pro Met Met Leu Thr
1               5                   10                  15

Val Arg Val Ala Leu Val Leu Ser Cys Ile Cys Pro Ala Asn Ser Ile
            20                  25                  30
```

```
Asp Gly Arg Pro Leu Ala Ala Gly Ile Val Val Thr Gly Asp Lys
        35                  40                  45

Ala Val Asn Ile Tyr Thr Ser Ser Gln Thr Gly Ser Ile Ile Val Lys
 50                      55                      60

Leu Leu Pro Asn Leu Pro Lys Asp Lys Glu Ala Cys Ala Lys Ala Pro
 65                  70                  75                  80

Leu Asp Ala Tyr Asn Arg Thr Leu Thr Thr Leu Leu Thr Pro Leu Gly
                 85                  90                  95

Asp Ser Ile Arg Arg Ile Gln Glu Ser Val Thr Thr Ser Gly Gly Arg
            100                 105                 110

Arg Gln Lys Arg Phe Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Thr Gln Glu Leu Gly Cys Ile Arg Ile Ala Gln Gln Val Gly Val
        195                 200                 205

Glu Leu Asn Leu Tyr Leu Thr Glu Leu Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp His Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445
```

Ser Ile Gln Asp Ser Gln Val Ile Ile Thr Gly Asn Leu Asp Ile Ser
    450                 455                 460

Thr Glu Leu Gly Asn Val Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Val Leu Ala Cys Tyr Leu Met Tyr Lys
                515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550

<210> SEQ ID NO 9
<211> LENGTH: 426
<212> TYPE: DNA
<213> ORGANISM: Mus sp.

<400> SEQUENCE: 9
atgtggctgc agaacctgct gttcctgggc atcgtggtgt acagcctgag cgcccctacc      60
agatccccca tcaccgtgac cagaccctgg aaacatgtgg aagccatcaa agaggccctg     120
aatctgctgg acgacatgcc cgtgaccctg aacgagagg tggaagtggt gtccaacgag      180
ttcagcttca gaaactgac ctgcgtgcag accggctga agatctttga gcagggcctg       240
agaggcaact tcaccaagct gaagggcgct ctgaacatga ccgccagcta ctaccagacc     300
tactgccccc ccaccccga gacagattgc gagacacaag tgaccaccta cgccgacttc     360
atcgacagcc tgaaaacctt cctgaccgac atccccttcg agtgcaagaa acccggccag     420
aagtga                                                                426

<210> SEQ ID NO 10
<211> LENGTH: 141
<212> TYPE: PRT
<213> ORGANISM: Mus sp.

<400> SEQUENCE: 10

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140

<210> SEQ ID NO 11
<211> LENGTH: 435
<212> TYPE: DNA
<213> ORGANISM: Homo sapiens

<400> SEQUENCE: 11
atgtggctgc agagcctgct gctgctgggc acagtggcct gtagcatctc tgcccctgcc    60
agaagcccta gcctagcac acagcccctgg gagcatgtga acgccatcca ggaagccaga   120
cggctgctga acctgagcag agacacagcc gccgagatga acgagacagt ggaagtgatc   180
tccgagatgt tcgatctgca agagcctacc tgcctgcaga cccggctgga actgtacaag   240
cagggcctga gaggcagcct gaccaagctg aagggacccc tgaccatgat ggccagccac   300
tacaagcagc actgcccccc cacacccgag acaagctgtg ccacccagat catcaccttc   360
gagagcttca agagaaacct gaaggacttc ctgctcgtga tccccttcga ctgctgggag   420
cccgtgcagg aatga                                                   435

<210> SEQ ID NO 12
<211> LENGTH: 144
<212> TYPE: PRT
<213> ORGANISM: Homo sapiens

<400> SEQUENCE: 12

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 13
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ttaagaaaaa a                                                        11

<210> SEQ ID NO 14
<211> LENGTH: 9
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 14 acgggtaga                                                               9

<210> SEQ ID NO 15
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cgccgccacc                                                             10

<210> SEQ ID NO 16
<211> LENGTH: 21
<212> TYPE: DNA
<213> ORGANISM: Newcastle disease virus
<220> FEATURE:
<221> NAME/KEY: CDS
<222> LOCATION: (1)..(21)

<400> SEQUENCE: 16 ggg agg aga cag aaa cgc ttt                                            21
Gly Arg Arg Gln Lys Arg Phe
1               5

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(21)

<400> SEQUENCE: 17 ggg ggg aga cag gaa cgc ctt                                            21
Gly Gly Arg Gln Glu Arg Leu
1               5

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(21)

<400> SEQUENCE: 18 cat aat aga acg aaa tcc ttt                                            21
His Asn Arg Thr Lys Ser Phe
1               5

<210> SEQ ID NO 19
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
cataataaaa tgaaatcctt t                                              21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
cataatagaa cgaaacgctt t                                              21

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Gly Arg Gln Glu Arg Leu Ile
1               5

<210> SEQ ID NO 22
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ttaagaaaaa atacgggtag aacgccgcca ccatgtggct gcagagcctg ctg           53

<210> SEQ ID NO 23
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tcattcctgc acgggctccc agcagtc                                        27

<210> SEQ ID NO 24
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
```

```
ttaagaaaaa atacgggtag aacgccgcca ccatgtggct gcagaacctg ctgttcctgg    60
```

<210> SEQ ID NO 25
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 25

```
gtatcacttc tggccgggtt tcttgcactc                                     30
```

<210> SEQ ID NO 26
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 26

```
ttaagaaaaa atacgggtag aacgccgcca ccatgtatag gatgcaactt ctgtc         55
```

<210> SEQ ID NO 27
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 27

```
gtcaagtcag ggtagagata atgctctggc                                     30
```

<210> SEQ ID NO 28
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 28

```
ttaagaaaaa atacgggtag aacgccgcca ccatgtattc aatgcagctg gcatc         55
```

<210> SEQ ID NO 29
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 29

```
gagttactga ggggaagttg aaatg                                          25
```

<210> SEQ ID NO 30
<211> LENGTH: 56
<212> TYPE: DNA
<213> ORGANISM: Artificial Sequence
<220> FEATURE:

```
<221> NAME/KEY: source
<223> OTHER INFORMATION: /note="Description of Artificial Sequence: Synthetic primer"

<400> SEQUENCE: 30
ttaagaaaaa atacgggtag aacgccgcca ccatggtgag caagggcgag gagctg 56

<210> SEQ ID NO 31
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 31
aattacttgt acagctcgtc catgc 25

<210> SEQ ID NO 32
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 32
acgggtagga catggtgagc aagggcgagg 30

<210> SEQ ID NO 33
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 33
tttttctaa catagtataa ttaaatcacc aaggatacaa ttggccagaa aaagagccta 60
ttaatatgtg attttcgcgt tacttgtaca gctcgtccat 100

<210> SEQ ID NO 34
<211> LENGTH: 7
<212> TYPE: PRT
<213> ORGANISM: Newcastle disease virus

<400> SEQUENCE: 34

Gly Arg Arg Gln Lys Arg Phe
1 5

<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Gly Gly Arg Gln Glu Arg Leu
1 5

-continued

```
<210> SEQ ID NO 36
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ttaagaaaaa atacgggtag aacgccgcca cc                                    32

<210> SEQ ID NO 37
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
tagcttaaga aaaatacgg gtagaacgcc gccacc                                 36

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

His Asn Arg Thr Lys Ser Phe Ile
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

His Asn Lys Thr Lys Ser Phe Ile
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

His Asn Arg Met Lys Ser Phe Ile
1               5

<210> SEQ ID NO 41
<211> LENGTH: 11
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 41
acgggtagga c                                                          11

<210> SEQ ID NO 42
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cgaaaatcac atattaatag gctcttttc tggccaattg tatccttggt gatttaatta      60
tactatgtta gaaaaaa                                                    77

<210> SEQ ID NO 43
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
aatccttaaa gaatcacagt acacaatcaa aagagatgtg gggacaacca cagctgtcac     60
tccgtcttct ctgcagaggg aagtgtcact cttatgtgga gagatactgt atgccaagca    120
cacagattac tcacatgcag ctgaagtagg aatgcagtac gtgagcacca cactgggagc    180
agagcgtaca cagcagatac taaagaactc aggtagtgag gtgcaggcag tattgaccaa    240
gacatactct cttgggaagg gcaaaaacag caaaggggag gagttgcaaa tgttagacat    300
acatggggtt gaaagaag                                                  318

<210> SEQ ID NO 44
<211> LENGTH: 198
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
acttctgtca tccagcaaat acgccatcca acggagcaca ggagatagta ttgatactcc     60
taattatgat gtgcagaaac acatcaataa gttatgtggc atgttattaa tcacagaaga    120
tgctaatcat aaattcactg ggttaatagg tatgttatat gcgatgtcta ggttaggaag    180
agaagacacc ataaaaat                                                  198

<210> SEQ ID NO 45
<211> LENGTH: 198
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45

```
gctgtgaaag caaaaacatc gtctctccgt tggcccaata ctcatgatcc gccaatgata    60
taaaaaaccg cggcaaggtc gcgcgtcttc gcatcgacac atcgttgata taggcgtgaa   120
gtctcaacat gtggcactcc tggaccagtg ggacaacgaa acgcgcctcc ttagaaggga   180
tacaatgacc ggctgagg                                                 198
```

<210> SEQ ID NO 46
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

```
gctgtgaaag caaaaacatc gtctctccgt tggcccaata ctcatgatcc gccaatgata    60
taaaaaaccg cggcaaggtc gcgcgtcttc gcatcgacac atcgttgata taggcgtgaa   120
gtctcaacat gtggcactcc tgga                                          144
```

<210> SEQ ID NO 47
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
gctgtgaaag caaaaacatc gtctgtctca acatgtggca ctcctggacc agtgggacaa    60
cgaaacgcgc ctccttagaa gggatacaat gaccggctga gg                      102
```

<210> SEQ ID NO 48
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48

```
gctgtgaaag caaaaacatc gtctgcgcct ccttagaagg gatacaatga ccggctgag     59
```

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Arg Arg Arg Arg Arg Phe
1               5

<210> SEQ ID NO 50
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:

```
                          Synthetic peptide"

<400> SEQUENCE: 50

Arg Arg Gln Lys Arg Phe
1               5

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Arg Gln Glu Arg Leu
1               5

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asn Arg Thr Lys Ser Phe
1               5

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Asn Arg Thr Lys Arg Phe
1               5

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asn Lys Met Lys Ser Phe
1               5
```